United States Patent
Austin et al.

(10) Patent No.: US 7,518,502 B2
(45) Date of Patent: Apr. 14, 2009

(54) SYSTEM AND METHOD FOR TRACKING SURGICAL ASSETS

(75) Inventors: Gene Edward Austin, Bartlett, TN (US); Ralph W. Donati, Jr., Collierville, TN (US); Nicholas W. Granville, York (GB); Mark E. Hulen, Collierville, TN (US); Sied W. Janna, Memphis, TN (US); Robert L. Morgan, York (GB); James K. Rains, Cordova, TN (US); Randall Troutman, Jenison, MI (US); Darren J. Wilson, York (GB)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 11/753,406

(22) Filed: May 24, 2007

(65) Prior Publication Data

US 2008/0030345 A1 Feb. 7, 2008

Related U.S. Application Data

(63) Continuation-in-part of application No. 11/275,012, filed on Dec. 1, 2005.

(51) Int. Cl.
*G08B 1/08* (2006.01)
(52) U.S. Cl. ............ 340/539.1; 340/572.1; 340/539.12; 340/539.13
(58) Field of Classification Search ... 340/572.7–572.9, 340/539.1, 539.27, 539.12, 539.13, 573.1, 340/585, 588; 235/385; 700/299
See application file for complete search history.

(56) References Cited

U.S. PATENT DOCUMENTS 3,729,740 A 4/1973 Nakahara et al.

4,818,998 A 4/1989 Apsell et al.
5,014,206 A 5/1991 Scribner et al.
5,129,605 A 7/1992 Burns et al.
5,222,600 A 6/1993 Stoddard et al.

(Continued)

FOREIGN PATENT DOCUMENTS

DE 3917876 A1 6/1989

(Continued)

OTHER PUBLICATIONS

Sands, RFID Technology Manages the Orthopedic Product Life Cycle, Sands, Orthopedic Design & Technology, May/Jun. 2006, pp. 40-44.

(Continued)

*Primary Examiner*—Benjamin C Lee
*Assistant Examiner*—Hoi C Lau
(74) *Attorney, Agent, or Firm*—Kilpatrick Stockton LLP

(57) ABSTRACT

A system and method for identifying, locating, and managing inventory of sterilized medical devices located within a sealed sterilization case in preparation for a surgical procedure. Communication tags, such as radio frequency identification (RFID) and/or Global Positioning System (GPS) tags, are connected to the medical device and communicate information wirelessly. Information is obtained from the communication tags and sent to the database where it is compared with the information in the database. The results may be displayed on the interface thereby providing the user with information about the medical instruments contained in the sealed sterilization case without breaking the seal of the sealed sterilization case.

29 Claims, 30 Drawing Sheets

U.S. PATENT DOCUMENTS

| | | | |
|---|---|---|---|
| 5,415,180 | A | 5/1995 | Horan |
| 5,570,783 | A * | 11/1996 | Thorne et al. ............... 206/366 |
| 5,588,005 | A | 12/1996 | Ali et al. |
| 5,610,811 | A | 3/1997 | Honda |
| 5,618,322 | A | 4/1997 | Mizuno et al. |
| 5,633,875 | A | 5/1997 | Hershey et al. |
| D381,259 | S | 7/1997 | Hayes |
| 5,917,423 | A | 6/1999 | Duvall |
| 5,936,527 | A | 8/1999 | Isaacman et al. |
| 5,975,349 | A | 11/1999 | Menes |
| 5,996,889 | A | 12/1999 | Fuchs et al. |
| 6,010,670 | A | 1/2000 | Berry, Jr. |
| 6,131,067 | A | 10/2000 | Girerd et al. |
| 6,223,137 | B1 | 4/2001 | McCay et al. |
| 6,232,870 | B1 | 5/2001 | Garber et al. |
| 6,324,904 | B1 | 12/2001 | Ishikawa et al. |
| 6,332,098 | B2 | 12/2001 | Ross et al. |
| 6,366,206 | B1 | 4/2002 | Ishikawa et al. |
| 6,555,721 | B2 | 4/2003 | Griffiths et al. |
| 6,714,121 | B1 | 3/2004 | Moore |
| 6,861,954 | B2 | 3/2005 | Levin |
| 7,088,249 | B2 | 8/2006 | Senba et al. |
| 7,102,510 | B2 | 9/2006 | Boling et al. |
| 7,102,525 | B2 | 9/2006 | Cuperus et al. |
| 7,118,029 | B2 | 10/2006 | Nycz et al. |
| 7,123,153 | B2 | 10/2006 | Thorstensen et al. |
| 7,227,469 | B2 | 6/2007 | Varner et al. |
| 7,256,695 | B2 | 8/2007 | Hamel et al. |
| 7,333,013 | B2 | 2/2008 | Berger |
| 2001/0013830 | A1 | 8/2001 | Garber et al. |
| 2001/0041948 | A1 | 11/2001 | Ross et al. |
| 2002/0032435 | A1 | 3/2002 | Levin |
| 2002/0067263 | A1 | 6/2002 | Tafoya et al. |
| 2002/0143320 | A1 | 10/2002 | Levin |
| 2002/0177476 | A1 * | 11/2002 | Chou .......................... 455/574 |
| 2002/0188259 | A1 | 12/2002 | Hickle et al. |
| 2002/0190845 | A1 | 12/2002 | Moore |
| 2003/0050038 | A1 | 3/2003 | Haave et al. |
| 2003/0052788 | A1 | 3/2003 | Chung |
| 2003/0060938 | A1 | 3/2003 | Duvall |
| 2003/0072701 | A1 | 4/2003 | Lin et al. |
| 2003/0117281 | A1 | 6/2003 | Shiharto et al. |
| 2003/0178488 | A1 | 9/2003 | Southard |
| 2004/0008123 | A1 | 1/2004 | Carrender et al. |
| 2004/0024711 | A1 | 2/2004 | Camping et al. |
| 2004/0099744 | A1 | 5/2004 | Cuperus et al. |
| 2004/0113790 | A1 | 6/2004 | Hamel et al. |
| 2004/0174261 | A1 | 9/2004 | Volpi et al. |
| 2004/0183672 | A1 | 9/2004 | Krishan et al. |
| 2004/0186683 | A1 | 9/2004 | Farber et al. |
| 2004/0203850 | A1 | 10/2004 | Oesterling |
| 2005/0026627 | A1 | 2/2005 | Boling et al. |
| 2005/0131397 | A1 | 6/2005 | Levin |
| 2005/0174235 | A1 | 8/2005 | Davis et al. |
| 2005/0177492 | A1 | 8/2005 | Camping |
| 2005/0265272 | A1 | 12/2005 | Thorstensen et al. |
| 2005/0285782 | A1 | 12/2005 | Bennett |
| 2006/0022867 | A1 | 2/2006 | Hessing |
| 2006/0028338 | A1 | 2/2006 | Krishan et al. |
| 2006/0043177 | A1 * | 3/2006 | Nycz et al. ................... 235/385 |
| 2006/0043179 | A1 * | 3/2006 | Nycz et al. ................... 235/385 |
| 2006/0080036 | A1 | 4/2006 | Stefan |
| 2006/0082471 | A1 | 4/2006 | Rockett et al. |
| 2006/0109105 | A1 * | 5/2006 | Varner et al. ........... 340/539.12 |
| 2006/0119481 | A1 * | 6/2006 | Tethrake et al. .......... 340/572.1 |
| 2006/0145871 | A1 | 7/2006 | Donati |
| 2006/0164246 | A1 | 7/2006 | Ghosh |
| 2006/0202817 | A1 | 9/2006 | Mackenzie et al. |
| 2006/0202818 | A1 | 9/2006 | Greenberg |
| 2006/0208881 | A1 * | 9/2006 | Suzuki ................... 340/539.27 |
| 2006/0229085 | A1 | 10/2006 | Lai et al. |
| 2006/0253248 | A1 | 11/2006 | Ames et al. |
| 2006/0256812 | A1 | 11/2006 | Reston et al. |
| 2007/0135866 | A1 * | 6/2007 | Baker et al. ................... 607/60 |

FOREIGN PATENT DOCUMENTS

| | | |
|---|---|---|
| DE | 9001113.9 | 4/1990 |
| DE | 195 14 284 A1 | 4/1995 |
| DE | 195 14 284 C2 | 4/1995 |
| DE | 196 14 719 A1 | 4/1996 |
| DE | 196 14 719 C2 | 4/1996 |
| DE | 200 05 496 U1 | 3/2000 |
| EP | 0747720 A1 | 12/1996 |
| EP | 0748080 A1 | 12/1996 |
| WO | WO 00/57336 | 9/2000 |
| WO | WO 01/97730 A2 | 12/2001 |
| WO | WO 01/97730 A3 | 12/2001 |
| WO | WO 03/060641 A2 | 7/2003 |
| WO | WO 2004/111924 A2 | 12/2004 |
| WO | WO 2004/111924 A3 | 12/2004 |
| WO | WO 2005/007336 A1 | 1/2005 |
| WO | WO 2005/091897 A2 | 10/2005 |

OTHER PUBLICATIONS

Lafontaine, Implementing an Automated RFID Asset Tracking System, Orthopedic Design & Technology, Sep./Oct. 2007, pp. 64-68.

Office Action dated Aug. 22, 2007 in related U.S. Appl. No. 11/275,012.

Office Action dated Feb. 15, 2008 in related U.S. Appl. No. 11/275,012.

* cited by examiner

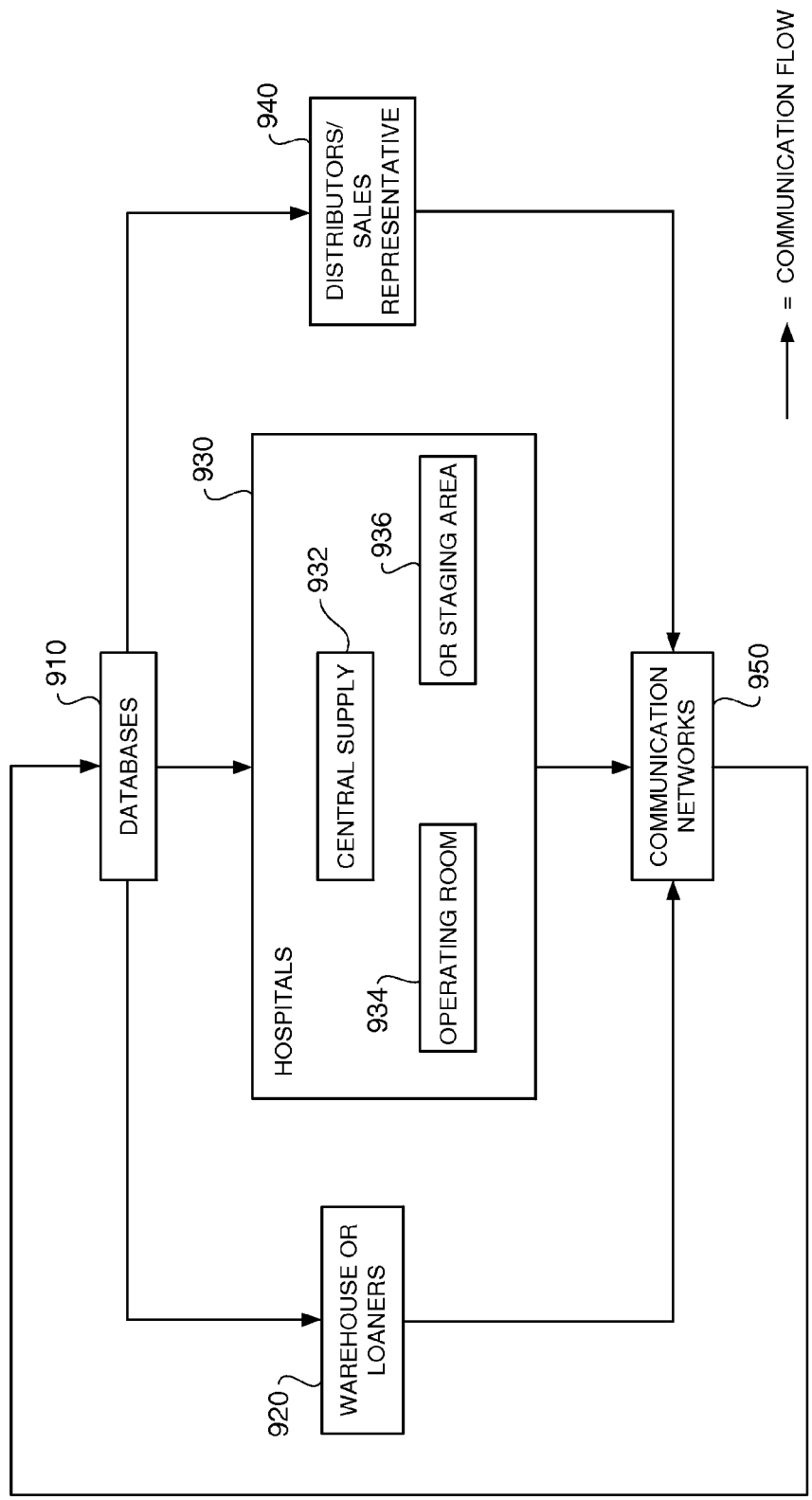

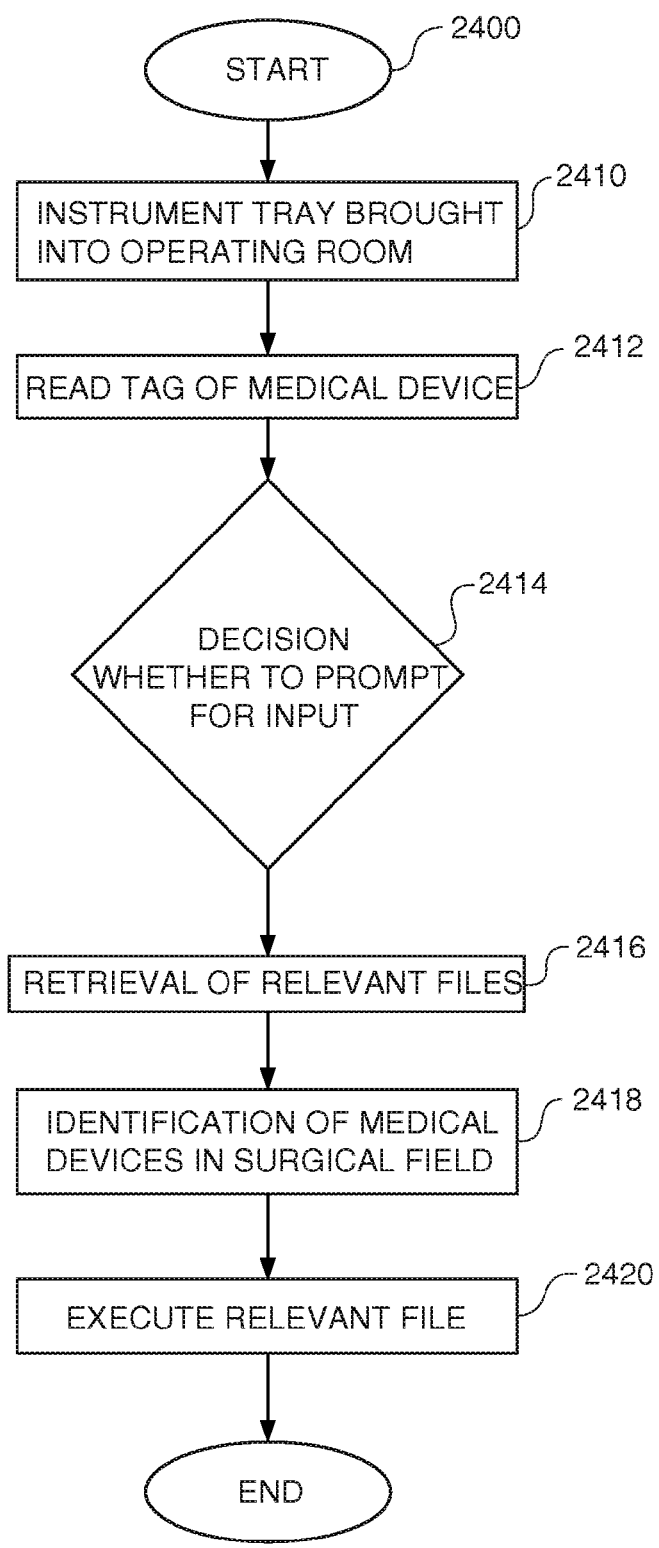

SYSTEM AND METHOD FOR TRACKING SURGICAL ASSETS

CROSS-REFERENCE TO RELATED APPLICATIONS

This application is a continuation-in-part of U.S. patent application Ser. No. 11/275,012 filed on Dec. 1, 2005, which claims priority to U.S. Provisional Patent Application No. 60/632,679 filed on Dec. 2, 2004. The entire contents of each disclosure are hereby incorporated by reference.

BACKGROUND OF THE INVENTION

1. Field of the Invention

This invention relates to systems and methods for identifying, locating, and managing inventory of sterilized medical devices located within a sterilization case that is sealed with a wrap in preparation for a surgical procedure.

2. Related Art

Surgical procedures generally involve various sterilized instruments. Sterilization can occur by known techniques such as autoclaving or those utilizing substances such as ethylene oxide, vapor hydrogen peroxide, or ozone. Before sterilization, the surgical instruments are placed inside a sterilization case that is typically made from steel, aluminum, titanium, or plastic. A sterilization case also may be referred to as an instrument tray or instrument case. The sterilization case is then wrapped in a plastic sheet and sealed. The plastic normally allows particles, condensed water, water vapor, and other substances to leave the sterilization case but prevents foreign contaminants from entering the sterilization case. Upon completing the sterilization process, the sterilization case containing the medical instruments is still within the sealed wrap. Prior to the surgical procedure and in the sterile field of the operating room, the instruments are typically removed from the wrap and sterilization case, placed on a table, and counted to validate that all instruments needed for the particular surgical procedure are on the table.

The tracking and management of surgical instruments in hospitals, instrument management companies, and sterilization companies is important to the efficiency and safety of use of hand held medical or surgical instruments. Inventory tracking is difficult to manage given that the instruments pass through the purview of various parties in the supply chain. Most hospitals in the United States have from 3,000 to 5,000 different types of instruments which are organized into 300 to 600 different types of sets. The content of these sets changes frequently. Moreover, individual devices within these sets become damaged and then require repair or replacement. It is desirable to be able to identify an inventory of the medical instruments to facilitate repair and replacement of these instruments should they become broken or worn. Instruments also can be misplaced, which may remain unknown until the instruments are removed from the sterilization case and the wrap in the sterile field of the operating room prior to surgery. If one or more instruments needed for the surgery are missing, hospital personnel must open another sealed plastic wrap to retrieve the missing instruments or locate a replacement within the hospital. Considerable time is required searching the hospital for a replacement to obtain a complete set of necessary instruments, which often involves opening other sealed cases. In the meantime, a patient is under anesthetic in the operating theatre waiting to be treated at a cost of $100 per minute and can often be delayed by fifteen minutes whilst hospital staff search for missing instruments. Once the instruments are retrieved, the remaining instruments in the opened cases have to be re-sterilized. Many healthcare facilities do not have effective solutions in place for tracking and management of surgical instruments, which is likely to grow as more instruments are purchased from manufactures. However, there is an increasing trend towards healthcare companies providing additional value to hospitals by tracking the hospital's entire inventory and ensuring that instruments are in fact in the instrument tray.

Hospitals, instrument management companies, and sterilization companies often have difficulty tracking and managing surgical instruments as they pass through the purview of various parties in the supply chain. For instance, instruments are sometimes misplaced, which may remain unknown until the instruments are removed from the sterilization case and the wrap in the sterile field of the operating room prior to surgery. If one or more instruments needed for the surgery are missing, personnel must open another sealed plastic wrap to retrieve the missing instruments or locate a replacement within the hospital. Personnel associated with surgical preparation sometimes need to open several sealed cases before they obtain a complete set of necessary instruments or spend time searching the hospital or other facility for a replacement. Furthermore, the remaining instruments in the second sterilization case and those opened thereafter, even if not used in a surgical procedure, always must be sterilized again.

Tracking individual instruments to specific trays is very challenging because each individual instrument needs to be scanned to the tray to form a link between the instrument and the tray, which is a labor intensive process. The techniques used to track surgical instruments include manual counting, color-coding and memory devices, which are discussed in turn below.

Various methods of counting the surgical instruments are known but none are particularly efficient. Manual counting involves a skilled technician physically counting each instrument on the surgical instrument tray and then comparing the count result to an information sheet that provides an inventory list of instruments used in a particular surgery. This count is usually performed close to, but before, the scheduled surgery while the patient is either already on the surgical table or on their way to the surgical room. If there is a discrepancy between the count and inventory list, the person counting or their assistant must quickly determine which instrument is missing and where a suitable replacement may be located before the surgical procedure begins. This tracking technique is unreliable and labor intensive because significant time is required to count the instruments manually, determine if there is a discrepancy between the count and the inventory list, and locate a replacement instrument before the surgical procedure begins. This time is costly to both the instrument company and hospital and could needlessly delay surgery. In addition, there is a likelihood for human error in counting the instruments and comparing the count to the inventory list. Furthermore, the correct instruments for a particular surgical procedure may still be missing during surgery, forcing the surgeon to use a closely related, but incorrect, instrument to perform the procedure. Manually tracking medical instruments also requires that the surgical instruments be removed from the wrap and the sterilization case before they are counted and compared to the inventory list for discrepancies.

A less common approach to instrument tracking includes color-coding techniques to identify different surgical instruments. Others optically mark each instrument and later scan the instruments with a hand-held scanner that is connected to a data terminal to ascertain the history of that instrument. Such a method typically requires that the instrument be removed from the tray on arrival and scanned by humans, a method that is costly and time-consuming. In addition, colors can fade and a significant percentage of the population is color blind.

Other methods to count surgical instruments and compare to an inventory list involve electronic mechanisms. Data carriers such as memory devices are a more expensive alternative method for manually counting surgical instruments and comparing them to an inventory. Memory devices permit the linking of large amounts of data with an object or item. Memory devices typically include a memory and logic in the form of an integrated circuit and a mechanism for transmitting data to and/or from the device.

One such method utilizes an optical scanner, in communication with a computer and database, which reads an encoded optical pattern of a bar code attached to each surgical instrument. Individual surgical instruments may be identified by the encoded optical pattern of the attached bar code. The optical scanner usually converts the encoded optical pattern of a bar code into an electrical signal that represents an identification code associated in the database with a particular surgical instrument. The computer typically contains a memory with database information about each surgical instrument and correlates that information to the identification code. The computer may then be programmed to produce information to a user in a variety of formats useful in an inventory procedure.

An optical tag is one form of memory device, which relies on an optical signal to transmit data to and/or from the tag. The optical scanner converts the encoded optical pattern of a bar code into an electrical signal that represents an identification code associated in the database with a particular surgical instrument. Thus, individual surgical instruments may be identified by the encoded optical pattern of the attached bar code. There are a number of disadvantages to the use of optical tags. First, the size of a bar code is too large for placement on relatively small surgical instruments. Second, the time required to scan and inventory a group of medical instruments can be quite lengthy, which can needlessly delay a surgical procedure. Third, optical scanning techniques require the user to present the optical scanner in close proximity to and in the line of sight of the bar code on each surgical instrument and orient the scanning device appropriately to the bar code. Furthermore, each surgical instrument and attached bar code must be scanned individually. Finally, the optical scanning procedure is prone to human error. If the user does not orient the optical scanner correctly with respect to a bar code on a surgical instrument, the scanner could fail to read that item and it could be deemed missing when it is actually present in the surgical instrument group.

Another method for managing medical instrument locations prior to and during surgery utilizing electronic mechanisms involves attaching certain radio frequency identification (RFID) tags to surgical instruments and a reader that obtains information associated with the particular medical instrument through radio frequency. A second type of memory device is the radio frequency identification (RFID) tag, which typically includes a memory for storing data, an antenna, an RF transmitter and receiver or an RF transceiver to transmit data, and logic for controlling the various components of the memory device. RFID tags can either be passive or active devices. Active devices are self-powered, by a battery for example. Passive devices do not contain a discrete power source but derive their energy from an RF signal used to interrogate the RFID tag. A reader is used to obtain information associated with the particular medical instrument through radio frequency. The reader is in electrical communication with a computer system having a database of information about the inventory. After detecting the radio frequency signal from the RFID tag, the reader causes the computer system to change the data in the database to account for the presence of a particular inventory item. If each instrument was embedded with an RFID tag and the tray in which the instruments are placed is retrofitted with a RFID reader, instruments could be identified and logged the moment they are placed in the tray. RFID tags typically comprise an electronic circuit placed on small substrate materials. The electronic circuits contain encoded data and transmit or respond (actively or passively) with encoded or identifiable data as a radio frequency signal or a signature when an interrogation radio frequency signal causes the electronic circuit to transmit or respond (whether actively or passively). Some RFID tags are able to have their data modified by an encoded radio signal.

A reader is a radio frequency emitter/receiver or interrogator. In accordance with general RFID tag methodology, the reader interrogates RFID tags that are within its range by emitting radio frequency waves at a certain frequency. Each tag may respond to a unique set of interrogation frequencies. An RFID tag typically responds to an interrogation by emitting or responding with coded or identification information as a radio frequency signal or signature and this signal or signature (whether actively or passively) is detected by the reader. The reader is in electrical communication with a computer system having a database of information about the inventory. After detecting the radio frequency signal from the RFID tag, the reader causes the computer system to change the data in the database to account for the presence of a particular inventory item.

An RFID tag system has several advantages over manual counting and optical scanning systems. For instance, the RFID tag reader is not required to be aimed directly at a tag in order to detect a signal. An RFID tag system does not require the user to orient a reader with respect to a particular tag in order to obtain the information as the optical scanning system requires. An additional advantage of an RFID tag system is the capability of quickly performing an inventory of a large group of items by successively reading a tag associated with each item without requiring the user to perform multiple procedural steps. This saves time and expense relative to manual and optical scanning systems.

In theory, RFID tagging is an ideal solution for tagging individual instruments. However, it is also a very challenging proposition given current limitations with RFID technology. Any device attached to a medical device or surgical instrument must be capable of performing despite being attached to various metals. It is difficult to apply and read RFID tags on metallic alloys because they tend to either absorb or reflect RF signals. This is a problem because many surgical instruments and implants are metallic interfering with weak RF signals of either the reader or tag, thus reducing the system's read range. The sterilization case is also metallic preventing electromagnetic energy, such as a radio frequency signal, from entering or leaving the case. Thus, an RFID reader is unable to communicate with the RFID tags located inside the sterilization case and the instruments must be removed from the case, including breaking the sealed wrap, in order for the reader to determine the inventory of a particular group of instruments. If, after reading the removed medical instruments, the medical instrument group does not include an instrument necessary for the particular surgical procedure, hospital or medical instrument company representatives must break another sealed sterilization packet, remove the instruments from the case and read or interrogate the RFID tags of that group to find the instrument necessary to complete the first instrument group. This process includes high costs and time delays in preparing for a surgical procedure.

Tag reliability can be impacted by environmental factors such as humidity, radiation and temperature. Previously, commercial-off-the-shelf RFID tags could not withstand extreme temperatures without a temperature-resistant housing. For that reason, using them for items like surgical instruments which undergo an autoclave or dry heat sterilization cycle is complicated. Costs are presently very high for custom chips, and tags capable of surviving the temperatures in a sterilization cycle would have to pass very close to an RFID-reader.

Known RFID tag systems have been used to manage medical instrument locations prior to and during surgery. For instance, the individual instruments may be scanned prior to the surgery to ensure that all instruments needed for the procedure are present. Prior to completing the surgery, the surgical tray table may be scanned again to ensure that instruments are located on the tray table instead of inside the patient. Some RFID tag systems describe scanning the surgical cavity of the patient to check for the presence of any instruments prior to completing the surgery.

Previous and current RFID tag systems used to manage and inventory medical instruments require that surgical personnel break the sterilization seal of a group of instruments and remove the instruments from the packet before the reader reads medical instruments. This is because instruments are typically contained within a metallic sterilization case and the sterilization case prevents electromagnetic energy, such as a radio frequency signal, from entering or leaving the case. Thus, an RFID reader is unable to communicate with the RFID tags located inside the sterilization case and the instruments must be removed from the case, including breaking the sealed wrap, in order for the reader to determine the inventory of a particular group of instruments. If, after reading the removed medical instruments, the medical instrument group does not include an instrument necessary for the particular surgical procedure, hospital or medical instrument company representatives must break another sealed sterilization packet, remove the instruments from the case and read or interrogate the RFID tags of that group to find the instrument necessary to complete the first instrument group. This process includes high costs and time delays in preparing for a surgical procedure.

A medical instrument inventory and management system that allows personnel to read data regarding the individual medical instruments contained within a sealed sterilization case would decrease the time necessary to locate a particular instrument. In addition, determining the presence of particular medical instruments inside a sealed sterilization case could decrease the time and cost of preparing for a surgical procedure because breaking a second and additional sealed packets requires another cleaning, decontamination, and sterilization process. Furthermore, personnel could read the inventory of several packets and select the one with the correct instrument group for a particular medical procedure.

Further, there is a problem in locating missing instrument trays, implant trays, and devices. For example, a tray may be lost at a hospital and hospital personnel are not able to locate the tray in time for surgery. Another example would be the tray lost in delivery or sent to an incorrect facility.

Sometimes a surgeon does not know how to use an instrument correctly or know what the next step is in a complicated surgical procedure. An example may be a resident using an implant system in the middle of the night and not knowing whether to perform step A or step B in the surgical procedure.

Hospitals face significant costs in managing inventory. Currently, a sales representative must review the inventory and determine if the hospital has an adequate amount of each product. If the sales representative determines that inventory is low, then the sales representative places an order to replenish the stock.

It would be of significant benefit if the instrument trays and surgical instrument inventory could be tracked. Tracking assets, physical inventory, and other objects in a large-scale enterprise is a daunting task. Traditionally, this requires a manual, physical inventory that must be regularly repeated. Further, as assets move from place to place, or out of the control of the enterprise, the conventional process requires a time-intensive paperwork trail to track the movement of the assets.

This already-daunting task is made even more difficult when the assets being tracked are physically similar because in that case every specific serial number must be verified to conclusively identify the specific item.

Recently, for items such as shipping containers, RFID tags have been used to partially automate this process in a real-time location system (RTLS). In the common case, an asset with an attached RFID tag transmits a unique identifier, allowing an RFID tag reader to easily receive the transmitted ID number and thereby identify specific shipping containers.

An entirely different type of asset location is used for locating stolen vehicles. A commonly known system of this type is the "LoJack" system manufactured by the LoJack Corporation of Westwood, Mass., and described in U.S. Pat. Nos. 4,818,998, 4,908,629, 5,917,423, and 6,665,613, all of which are hereby incorporated by reference. In general terms, this type of system uses a remotely activated system to track a vehicle in motion, using transceivers installed in the target vehicle in combination with transceiver/detectors mounted on other vehicles. Typically, a LoJack system is used to track stolen vehicles. When a target vehicle is reported stolen, its transceiver is remotely activated, and thereafter police units that are specially equipped with transceiver/detectors can detect and locate the target vehicle.

LoJack is a form of an asset location system that utilizes a special FCC-allocated radio frequency (173.075 MHz), an older technology, very high frequency (VHF) signal. The LoJack transceiver is passive until activated by police radio towers, and specially equipped police cruisers with receivers must work together to triangulate and locate the target vehicle. LoJack does not utilize global positioning satellites (GPS) for location information.

Another type of long-range vehicle-tracking system uses GPS to identify the current location of a vehicle. In this case, a GPS receiver is mounted in the vehicle to determine the vehicle location, and a separate transmitter is used to send the location data to the person or entity tracking the vehicle. In the common ONSTAR system, cellular telephone technology is used to activate the GPS receiver and to transmit the location data to the ONSTAR service center. ONSTAR is a registered trademark of OnStar Corporation of Troy, Mich.

Goods shipped to a destination from a manufacturing plant, warehouse or port of entry are normally tracked to assure their timely and safe delivery. Tracking has heretofore been accomplished in part by use of various shipping documents and negotiable instruments, some of which travel with the goods and others of which are transmitted by post or courier to a receiving destination. This paper tracking provides a record which is completed only on the safe delivery and acceptance of the goods. However, there sometimes is a need to know the location of the goods prior to delivery or acceptance. Knowledge of the location of goods can be used for inventory control, scheduling and monitoring.

Shippers and/or distributors have provided information on the location of goods by tracking their vehicles and knowing what goods are loaded on those vehicles. Goods are often loaded aboard shipping containers or container trucks, for example, which are in turn loaded aboard railcars. Various devices have been used to track such vehicles. In the case of railcars, passive radio frequency transponders mounted on the cars have been used to facilitate interrogation of each car as it passes a way station and supply the car's identification. This information is then transmitted by a radiated signal or land line to a central station which tracks the locations of cars. This technique, however, is deficient in that whenever a particular railcar remains on a siding for an extended period of time, it does not pass a way station. Moreover, way station installations are expensive, requiting a compromise that results in way stations being installed at varying distances, depending on the track layout. Thus, the precision of location information varies from place to place on the railroad.

Recently, mobile tracking units have been used for tracking various types of vehicles, such as trains. Communication has been provided through the use of cellular mobile telephone or RF radio link. Such mobile tracking units are generally installed aboard the locomotive which provides a ready source of power. However, in the case of shipping containers, container truck trailers and railcars, a similar source of power is not readily available. Mobile tracking units which might be attached to containers and vehicles must be power efficient in order to provide reliable and economical operation. Typically, a mobile tracking unit includes a navigation set, such as a GPS receiver or other suitable navigation set, responsive to navigation signals transmitted by a set of navigation stations which may be either space-based or earth-based. In each case, the navigation set is capable of providing data indicative of the vehicle location based on the navigation signals. In addition, the tracking unit may include a suitable electromagnetic emitter for transmitting to a remote location the vehicle's location data and other data acquired from sensing elements on board the vehicle. Current methods of asset localization require that each item tracked be individually equipped with hardware which determines and reports location to a central station. In this way, a tracked asset is completely "ignorant" of other assets being shipped or their possible relation to itself. In reporting to the central station, such system requires a bandwidth which scales approximately with the number of assets being reported. The aggregate power consumption over an entire such system also scales with the number of assets tracked. Further, because both the navigation set and the emitter are devices which, when energized, generally require a large portion of the overall electrical power consumed by the mobile tracking unit, it is desirable to control the respective rates at which such devices are respectively activated and limit their respective duty cycles so as to minimize the overall power consumption of the mobile tracking unit.

Most present-day asset tracking systems are land-based systems wherein a radio unit on the asset transmits information to wayside stations of a fixed network, such as the public land mobile radio network or a cellular network. These networks do not have ubiquitous coverage, and the asset tracking units are expensive. A satellite-based truck tracking system developed by Qualcomm Inc., known as OMNITRACS, is in operation in the United States and Canada. This system requires a specialized directional antenna and considerable power for operation, while vehicle location, derived from two satellites, is obtained to an accuracy of about one-fourth kilometer. U.S. Pat. No. 5,129,605 to Burns et al., incorporated by reference herein, describes a rail vehicle positioning system for installation on the locomotive of a train and which uses, to provide input signals for generating a location report, a GPS receiver, a wheel tachometer, transponders, and manual inputs from the locomotive engineer.

In an asset tracking system disclosed in U.S. Pat. No. 5,651,800, entitled "Local Communication Network for Power Reduction and Enhanced Reliability in a Multiple Node Tracking System" by Welles et al. and in U.S. Pat. No. 5,588,005 entitled "Protocol and Mechanism for Primary and Mutter Mode Communication for Asset Tracking" by Ali et al., both of which are incorporated herein by reference, a tracking system based on a "mutter" mode local area network is used to generate data that is transmitted to a central station. In this asset tracking system, there are two modes of communication. One mode is communication between the central station and the tracking units, which is usually via satellite. The second mode is a local area network, referred to as the "mutter" mode, between tracking units. One of the tracking units, denoted the master unit, communicates with the central station.

One of the chief challenges in using the first mode of communication is to devise a protocol for the communications that will provide efficient use of the communication facilities and respect the special sensitivities of the reporting scenario. Such protocol should meet the following guidelines:

1. The protocol should be two-way, thereby supporting transmission to and from a central station.

2. The protocol must accommodate a large number of assets and be scalable so that assets can be added and deleted without impacting normal service.

3. The protocol must accommodate variable length messages. The variable length may arise from a number of considerations; for example, the individual asset may have extra sensor data to report in addition to its location.

4. The protocol must have a chatter suppression feature to allow selective turn-off of a specific malfunctioning asset's transmitter.

5. The protocol must function efficiently if used over an extremely long path such as is implied by use of a geostationary satellite.

6. The protocol must allow encryption or a privacy feature to be added later without significantly impacting the capacity.

7. The protocol must be sufficiently robust to allow an asset to enter the system at any time without knowledge that cannot be gleaned following its entry into the system, and must tolerate occasional transmission errors and not be unstable but degrade gracefully under additional load.

8. The protocol must not require the assets to be receiving all the time but accommodate a duty cycle significantly less than 100% for periods of monitoring communication frequencies.

The protocol must be designed to be easily adjusted and nominally reprogrammable to allow presentation of its efficiency as the operational scenario matures.

The term "telematics" is often used to refer to automobile based asset tracking systems that combine GPS satellite tracking and wireless communications for automatic roadside assistance and remote diagnostics.

Referring to FIG. 1, there is shown a block diagram illustrating a general telematics system 100 in accordance with the prior art. Typically, a telematics system 100 includes services 110, platforms 120, networks 130, auto/freight sector clients 140, and positioning technologies 150. The services 110 provided by the telematics system 100 may include automatic roadside assistance, accident notification, traffic information, diagnostics, mobile Internet access, fleet management, and navigation. The platforms 120 on which the telematics system 100 may update may include servers, gateways, and billing and customer-care call centers. The networks 130 by which communications are provided may include voice, short messaging system ("SMS") messaging, and wireless application protocol ("WAP"). The auto/freight sector clients 140 serviced by the telematics system 100 may include passenger vehicles, trucks, freight, public safety applications. Typically, telematics systems 100 perform applications including vehicle or equipment (i.e., asset) location, driver concierge services, fleet management, and navigation/traffic information services.

Typically, an asset tracking device or module is installed in the vehicle to be tracked. The location of the device is determined by the telematics system 100 using a positioning technology 150, such as GPS or time difference of arrival ("TDOA"). The location information is then provided to an application to service a customer.

Briefly, the GPS was developed by the U.S. Department of Defense and gradually placed into service throughout the 1980s. The GPS satellites constantly transmit radio signals in L-Band frequency using spread spectrum techniques. The transmitted radio signals carry pseudorandom sequences which allow users to determine location on the surface of the earth (within approximately 100 feet), velocity (within about 0.1 MPH), and precise time information. GPS is a particularly attractive navigation system to employ, being that the respective orbits of the GPS satellites are chosen so as to provide world-wide coverage and being that such highly-accurate radio signals are provided free of charge to users by the U.S. government. The main problem with current GPS technology is the requirement for an unobstructed view of the sky for communication with GPS satellites. Its advantage is that it can provide a location anywhere in the world without any additional infrastructure on the ground. Improved receiver performance and signal processing and new technologies, like "Enhanced GPS," will provide locations where traditional GPS would fail.

On the other hand, TDOA uses the existing cellular network infrastructure to determine location. Referring to FIG. 2, there is shown a flow diagram illustrating a typical TDOA process 200. The process requires signal timing information from at least three different antenna sites. At step 1, a handset or vehicle places a call (e.g. a 911 call). At step 2, antennae receive the signal from the handset or vehicle and pass it to a carrier's mobile switching office. At step 3, TDOA equipment measures the difference in the time the cellular radio signals arrive at the antenna sites and translate that data into location data (i.e., longitude and latitude data). At step 4, the carrier forwards voice call and location data to a Public Safety Answering Point ("PSAP"). The use of TDOA is typically restricted to areas where coverage from multiple towers is available.

The communications networks 130 for linking tracking devices to platforms 120 to provide services 110 to customers include cellular and telephone networks. With respect to cellular networks, network providers typically make use of the Advanced Mobile Phone System ("AMPS") control channel frequencies for the transfer of small data packets. The use of the cellular network control channel provides more robust communication than cellular voice traffic so that it is possible to communicate with devices located in places where ordinary cell phones have marginal or intermittent voice coverage. Clients of these virtual carriers can make use of a TCP/IP data link to connect their operations centre to the virtual carrier network which then provides continent wide coverage through cellular service providers.

For example, in U.S. Pat. No. 6,131,067, to Girerd, et al, a client-server based system is described in which the location of a tracking device is determined using GPS information. This location is then reported to a user via the Internet. The entire disclosure of U.S. Pat. No. 6,131,067 is hereby incorporated by reference.

It would be of significant benefit if existing telematics systems could be adapted for tracking medical devices and/or sterilization cases. Medical devices may include medical implants, medical instruments, and other components.

There is a need in the art for a system and method for locating missing sterilization cases and/or medical devices. Further, there is a need in the art for a system that provides instruction to medical personnel on how to perform certain procedures or how to use certain medical instruments. Finally, there is a need for continued improvement in the area of hospital inventory management.

SUMMARY OF THE INVENTION

In one aspect of the invention, there is provided a system for tracking one or more surgical assets. As examples, the surgical asset may be a sterilization case, a medical instrument tray, a medical instrument, or a medical implant. The system includes a first receiver, a processor, a first long-range transmitter, a global positioning satellite reader, a medical device readiness sensor, a second long-range transmitter, and a storage device. The first receiver receives a signal from a short-range transmitter. The signal contains localized location information corresponding to the surgical asset. The processor determines if the localized location information corresponding to the surgical asset has been received. The first long-range transmitter requests location information of the surgical asset. The global positioning satellite reader is operatively connected to the surgical asset, and the global positioning satellite reader is adapted to provide localized location information. The medical device readiness sensor is configured to provide readiness data. The second long-range transmitter is operatively connected to the medical device and is electrically connected to the global positioning satellite reader, the second transmitter is configured to transmit localized location information obtained from the global positioning satellite reader. The storage device electronically stores the localized location information and the readiness data.

The short-range transmitter may utilize radio frequency transmission. Similarly, the first long-range transmitter and the second long-range transmitter may utilize microwave transmission.

In one embodiment, at least one of the first long-range transmitter and the second long-range transmitter form a portion of a wireless telephone network.

In one particular embodiment, the surgical asset is a sealed sterilization case adapted to allow radio frequency signals to pass through at least one side of the case. This embodiment includes: at least one radio frequency identification tag; at least one medical instrument contained in the sealed sterilization case and attached to the radio frequency identification tag; and a reader adapted to obtain information, via radio frequency, from said radio frequency identification tag. The sterilization case may have at least one surface that has at least one opening adapted in size or shape to allow radio frequency signals to enter and leave the case. Further, the sterilization case may be composed of a material that is configured to allow radio frequency signals to enter and leave the case. The radio frequency identification tag associated with the instrument may be embedded inside the instrument or attached on the outside surface of the medical instrument. The radio frequency identification tags may be passive or active.

In some embodiments, the reader is electrically connected to a microprocessor and may be in wireless communication with the microprocessor.

In another aspect of the invention, there is provided a method of tracking at least one surgical asset. The method includes the steps of: (a) detecting if localized location information corresponding to the surgical asset has been received, the localized location information corresponding to a location determined from a signal received from a short-range transmitter; (b) if the localized location information has been received, then storing the localized location information; (c) if no localized location information has been received for a predetermined amount of time, then sending a location request; (d) receiving secondary location information corresponding to the surgical asset, the secondary location information corresponding to a location determined from global positioning satellites; (e) detecting if the surgical asset is ready for use; and (f) storing the secondary location information.

In another aspect of the invention, there is provided a system for tracking at least one surgical asset. The system includes an electronic component, a location module, a power module, a communication module, an antenna module, and a medical device readiness module. The electronic component includes a processor module and is operatively connected to the surgical asset. The location module is electrically connected to the processor module and includes a global positioning satellite reader. The power module and the communication module are electrically connected to the processor module. The communication module has a short-range receiver and a long-range receiver. The antenna module and the medical device readiness module are also connected to the power module.

In yet another aspect of the invention, there is provided a method for retrieving surgical information corresponding to a surgical asset. The method includes the steps of: (a) detecting the surgical asset; (b) identifying the surgical asset; (c) retrieving a stored file corresponding to the identified surgical asset; and (d) executing the stored filed.

The advantage of being able to determine if all needed instruments or implants are present in a tray is that it allows the user to perform this task pre-operatively allowing time for the device to be located or replaced before it is needed in surgery. Also, it helps someone who is not intimate with the system know if the missing instrument(s) or implant(s) in the tray is needed for the surgery or not. Often there are spots made available in the set for a rarely used instrument, and a novice user may notice this unfilled space and order a replacement part. This invention eliminates such scenarios by informing the user that as to whether all necessary instruments to perform the surgery are present in the set.

The advantage of being able to track the whereabouts of an instrument, implant, or set within an area such as a hospital is that it prevents surgeries having to be slowed or delayed due to not being able to locate for example a needed instrument. Being able to locate a misplaced instrument helps prevent the user from trying to find a needle in a hay stack, and also cuts down on parts that are unnecessarily re-ordered because an instrument in misplaced.

In one aspect of the invention, there is provided an electronic instrument tray which allows personnel to determine whether there are any individual medical instruments missing within a sealed sterilization case. This is achieved using electrical circuits which are contained within the tray. A method of determining the status of the circuit is displayed either on the outside of the tray or on a hand held device or computer. The tray does not need to be opened for the circuit to work or to discover its status. In the simplest form, the circuit detects whether the tray contains a complete set or not. The solution described herein could accommodate plastic trials and instruments where current flow cannot be achieved with non-conducting materials. The housing may be adapted so that electrical contact is made by adding switches which are activated when the instrument is located in its housing. More complex versions identify which instruments are missing. For example, the system is capable of identifying the individual medical instruments inside a sealed sterilization based on the unique electrical resistance associated with its own particular instrument which may be displayed on a screen. The word 'instrument' could be replaced by the phrase 'implant or implant component', and a similar device could determine whether all components of an implant are present in an implant tray. Powering the electrical circuits can be provided either internally using a sterilizable internal battery or external device inserted into the case when inventory is required.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 20 is a block diagram illustrating data flow of location data;

FIG. 42 is a flow chart illustrating a process for retrieving surgical information.

DETAILED DESCRIPTION OF THE EMBODIMENTS

The following description of the preferred embodiment(s) is merely exemplary in nature and is in no way intended to limit the invention, its application, or uses.

Figure 1:
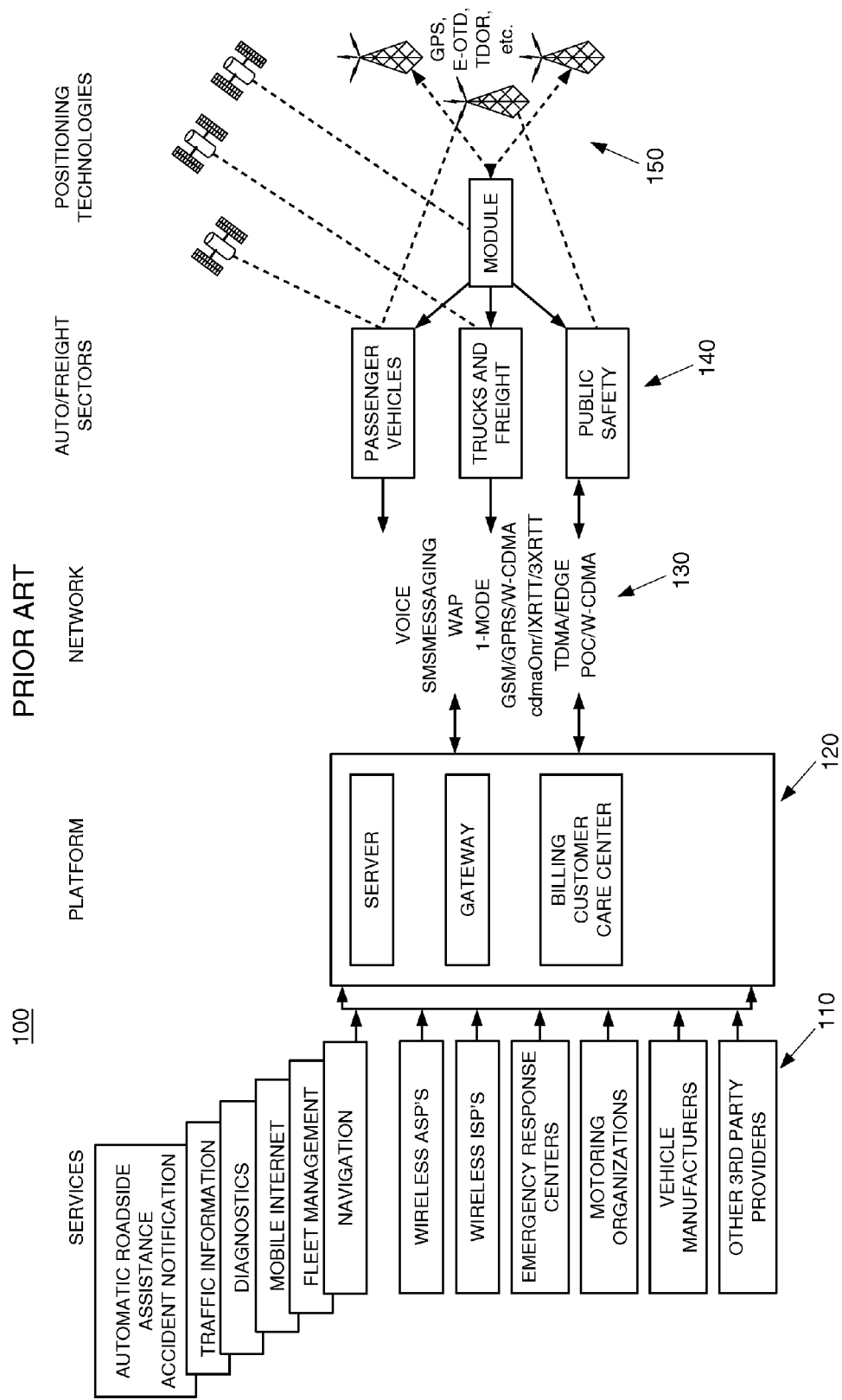
FIG. 1 is a block diagram illustrating a general telematics system in accordance with the prior art.
Figure 2:
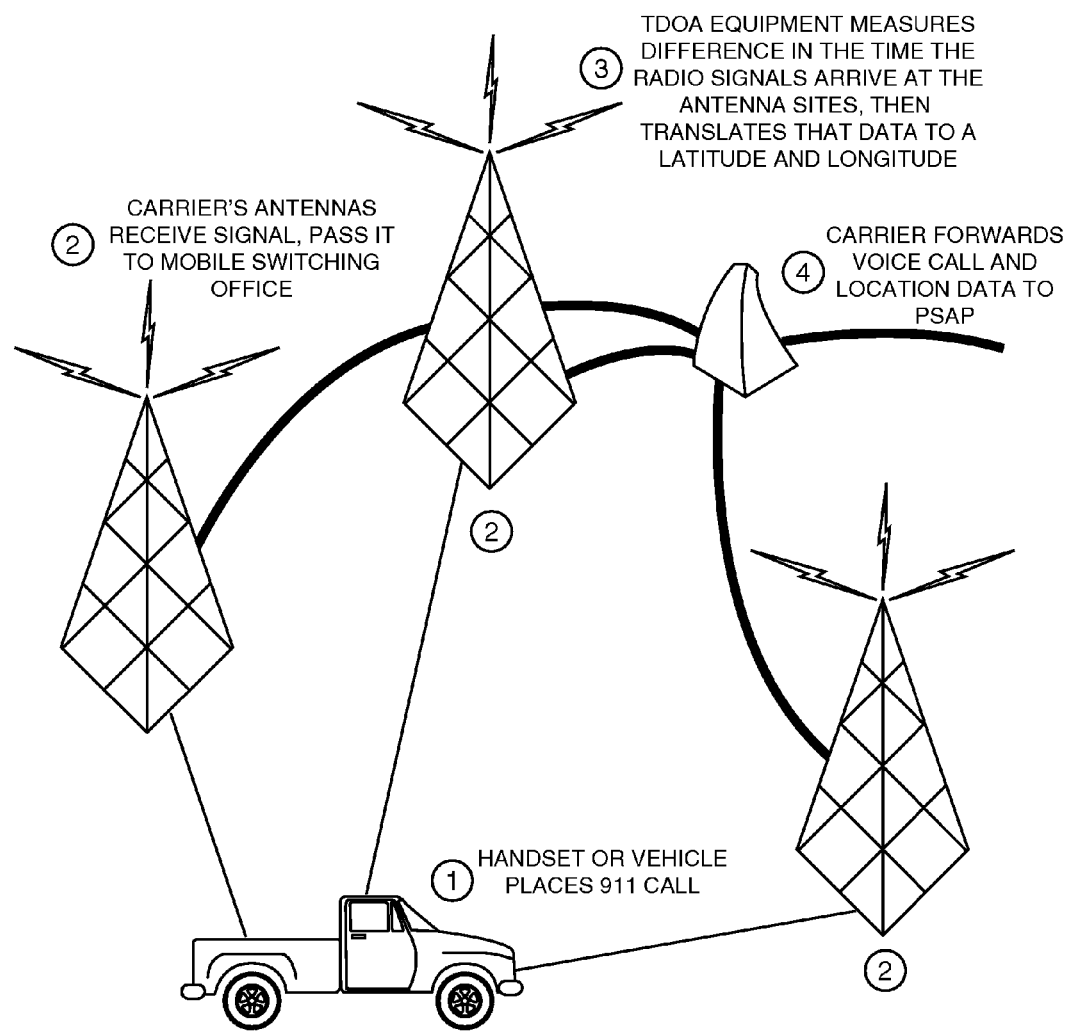
FIG. 2 is a flow chart illustrating the TDOA process in accordance with the prior art.
Figure 3:
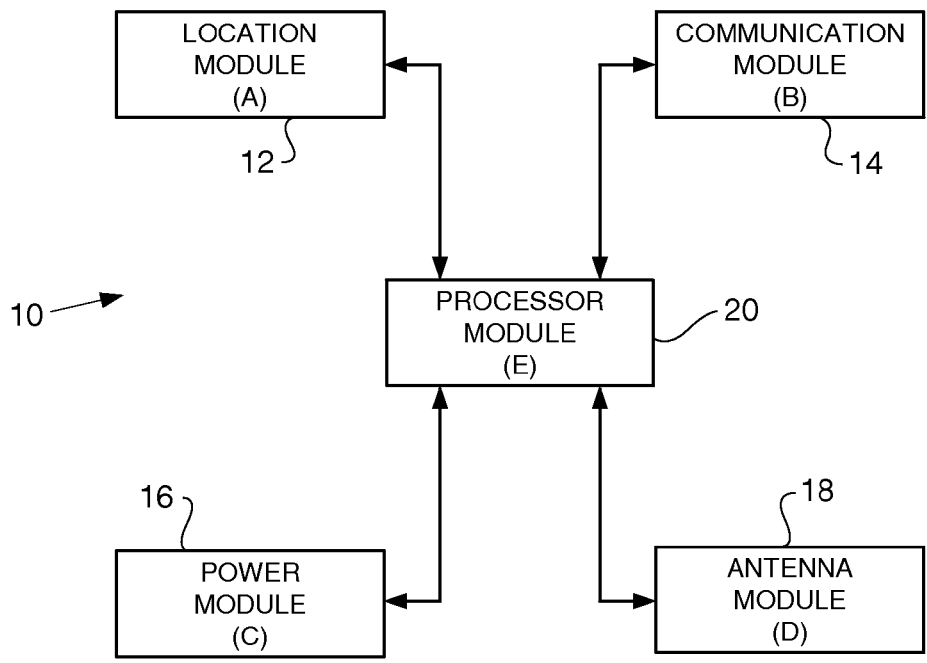
FIG. 3 is a block diagram of a medical device tracking system.

FIG. 3 illustrates a system 10 for tracking one or more surgical assets. As examples, a surgical asset may be a sterilization case, an instrument, or an implant. The system 10 includes five inter-related modules that work together to provide the intended functionality: a location module 12, a communication module 14, a power module 16, an antenna module 18, and a processor module 20. The components and data processing of each module are described below.

FIG. 3 illustrates the framework of system 10. System 10 comprises five inter-related operational modules of which each has a specially designed integrated circuit board handling different functions of system 10. The location module 12 identifies the best available position information and stores the information in its storage component available for retrieval at any time. The current position information is passed to the processor module 20 for interaction with other modules. Communication module 14 detects the most cost-effective, available communication mode and passes such information to processing module 20. At any moment, the communication mode is stored in processor module 20 and communication is established. Power module 16 manages the system's power use and recharging. The current state of the power use is stored in processor module 20. Whenever system 10 is not moving, power module 16 shuts down system 10 and keeps only the necessary sensors up for instruction. Power module 16 also manages the recharging mechanism whenever necessary. Antenna module 18 connects antennas 22, 24, 26 and 28 of a GPS receiver, local RF, cellular networks, and satellites receiver, respectively, with processor module 20 as described in greater detail in FIG. 11. Processor module 20 controls the storage and flow of data throughout system 10. The current parameters are kept and intelligent decisions are made within the processor module 20. The processor module 20 also provides instructions to all other modules 12, 14, 16 and 18 to perform according to the status of system 10.

Location Module

Figure 4:
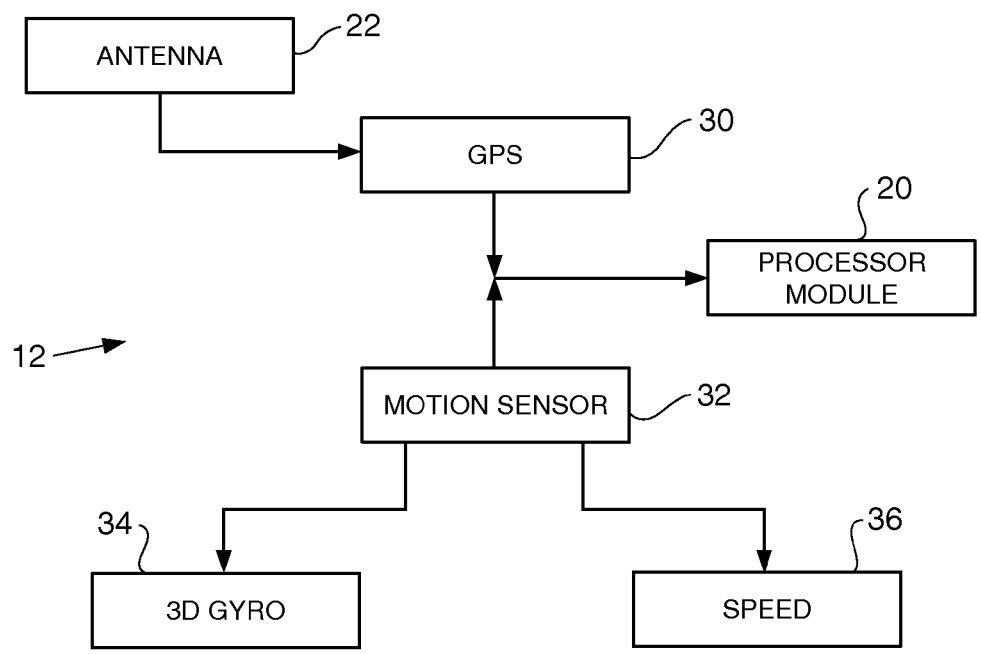
FIG. 4 is a block diagram of a location module.

In FIGS. 3 and 4, location module 12 includes an embedded integrated circuit board including two components: a GPS engine board, or chipset, 30 capable of processing data received from the GPS antenna 22 of antenna module 18, and a dynamic motion sensor 32. As an example, the dynamic motion sensor 32 may include a three-dimensional gyro motion detector 34 and a speed computation processor 36. GPS engine board 30 is useful for both determining the initial location of system 10 and correcting location information during the movement of system 10, whenever valid GPS readings are available. Motion sensor 32 is used to dynamically adjust the location of system 10 based on the internal calculation of the direction and speed of any movement. The accurate location of system 10 is obtained by a combination of three internal processes in the location module, namely location initialization, motion detection, and GPS correction.

Figure 5:
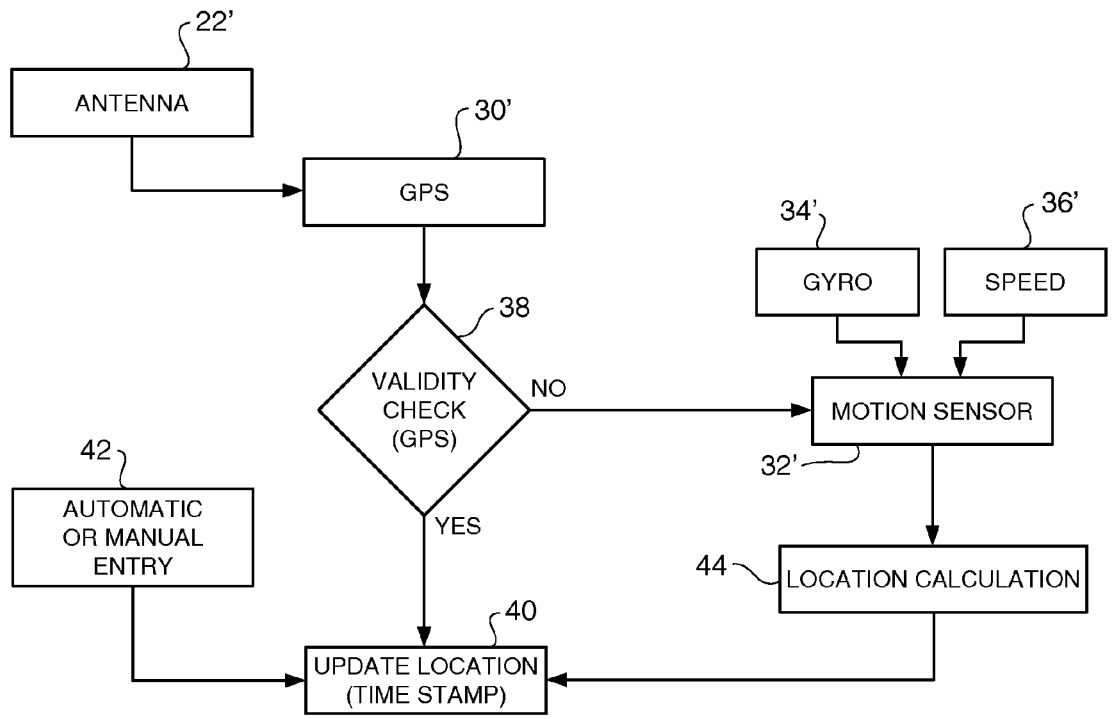
FIG. 5 is a flow chart illustrating the flow of data and control in the location module.

GPS antenna 22 sends the most recent GPS signal to GPS chipset 30, which in turn passes the latest valid position reading to processor module 20. In the depicted embodiment, motion sensor 32 is always active and is connected to gyro 34 and speed calculator 36. The received GPS reading is constantly checked for validity. Motion sensor 32 determines if system 10 needs to "wake up" or can remain in the sleep mode. Gyro 34 derives the motion of system 10 in three dimensions. Speed calculator 36 estimates the acceleration and deceleration at any given moment. The position information derived from gyro 34 and speed calculator 36 is processed internally for position calculation. The data flow in location module 12 is depicted in FIG. 5.

Location Initialization

Internally, the location of system 10 is expressed with the geographical coordinate system in conventional longitude and latitude readings. The initial location of system 10 is set when system 10 is ready to deploy, using either (1) a GPS data entry, (2) a location initialization input device, or (3) a manual position entry. Any one of the three processes is sufficient to initialize the location of system 10.

Consider first GPS entry. The initial location can be set with the built-in GPS engine board 30. One only needs to take system 10 outdoors for a few seconds, and system 10 initializes its GPS position by itself. The GPS position is then stored in the memory. This method is most convenient as it only requires direct exposure to GPS satellites. This is diagrammatically illustrated in FIG. 5 where receipt of GPS data from the satellite location system is symbolically represented by step 22' and the data processed and its earth coordinates generated at step 30'. The validity of the GPS coordinates and data is checked in a conventional manner at step 38 to insure a valid reading and stored in memory at step 40.

Consider now the use of the location input routine. One can initialize the position using a simple data entry device, such as a personal computer, a laptop computer, a handheld computer, a personal data assistant (PDA), or any other device that can send a position signal through a serial port, infrared port, USB port, network connector, or any communication port to allow for automatic or manual entry of position information. This method is most useful when a large number of devices are to be initialized, such as at the manufacturer's site. The longitude and latitude readings are known and stored in a simple utility program. As soon as system 10 is connected to the external data entry device (not shown) at step 42, the location is automatically stored in the memory and the initial position of system 10 is initialized.

In a similar manner, a third way of initializing the location is to enter the longitude and latitude of the current position manually at step 42 using any external device through a serial port, infrared port, USB port, network connector, or any such device to allow for manual entry of the location. This mechanism ensures that system 10 can be used after being dormant for a long period of time and the current location can be re-initialized whenever necessary.

Once initialized, the location information is kept in processor module 20. The initial location will be changed along with the movement of system 10. As soon as system 10 is moved, the current location reading becomes different from the initial location.

Motion Detection

In FIG. 4, the location module 12 is installed with a motion detector 32 including a three dimensional gyro, or direction detector, 34 and a speed detector 36. As shown in FIG. 5 at step 34' the three dimensional gyro 34 calculates the motion of system 10 in three dimensions, typically expressed as x, y, and z, where x represents longitude reading, y represents latitude reading, and z represents altitude reading. The three dimensional gyro 34 is composed of three independent sensors each of which calculates the change in velocity, acceleration or deceleration along an assigned axis. Speed detector 36 calculates at step 36' the movement of system 10 along the three dimensions and converts such motion into a new position of system 10. The initial location of system 10 is altered according to the motion of system 10. The calculation is made inside system 10 at step 32' and no GPS reading is required for such calculation. Motion detection is automatically activated whenever system 10 is moving while there is no valid GPS reading as determined at step 38.

GPS antenna 22 always passes the GPS signals to the GPS chipset 30. Each GPS signal is evaluated for validity at step 38. If the latest GPS reading is valid, both the updated current position and the time stamp when the signal is received are passed to processor module 20 at step 40 for storage and real-time retrieval. If the latest GPS is not valid, a position calculation based on the motion sensor is activated at step 32'.

On the right-hand side of FIG. 5, motion sensor 32 determines at step 32' if system 10 is moving. If system 10 is not moving, no position calculation is needed and the current position is maintained. If system 10 is moving, gyro 34 and speed calculator 36 pass their latest quantities to the motion sensor 32 for position calculation at step 44. The calculated result is used to update the current position of system 10 at step 40.

GPS Correction

Using a motion detector to dynamically adjust location information is subject to errors at different steps of the computation. In general, the errors are small and random for each computation. Thus, over a long period of time, the individual errors may balance out among themselves or the cumulative error may accumulate over time. In any case, it is always helpful to correct the location reading whenever a GPS reading becomes available. When system 10 is inside a building, tunnel, parking structure, or a narrow valley, for example, a valid GPS may not be available. In this case, the current position of system 10 is adjusted though the motion detector. Whenever a valid GPS reading becomes available, the current location is automatically corrected at step 44.

GPS correction may take place even when system 10 is not directly exposed to GPS satellites. When GPS antenna 22 is in the direct line of sight of GPS satellites, the signals are most reliable and accurate. An additional mechanism is automatically activated when no direct GPS readings are available. The indirect GPS reading may be obtained from either reflected or re-radiated satellite signals. Although the reflected or re-radiated GPS signals do not provide the same level of positional accuracy as direct line readings, they nonetheless provide enough accuracy within a 20-meter range. In the future, a major public structure may be installed with a GPS receiver that re-radiates GPS signals to the neighborhood. Additionally, some structures, such as a hospital, may re-radiate the signal internally. System 10 will then be able to detect such re-radiated GPS signals and correct the position automatically.

Another way of correcting GPS position is through an RF connection wherever localized position information is broadcast from a station. Different modes of position information can be transmitted for short-range communication applications. As an example, designated short-range wireless communication frequencies, such as such as ZIGBEE™ or BLUETOOTH™, may be used for broadcasting localized position information within a hospital or other healthcare facility. ZigBee is a published specification set of high level communication protocols designed for wireless personal area networks (WPANs). The ZIGBEE trademark is owned by ZigBee Alliance Corp., 2400 Camino Ramon, Suite 375, San Ramon, Calif., U.S.A. 94583. Bluetooth is a technical industry standard that facilitates short range communication between wireless devices. The BLUETOOTH trademark is owned by Bluetooth Sig, Inc., 500 108th Avenue NE, Suite 250, Bellevue Wash., U.S.A. 98004. Another possible implementation in the future is the use of RF among public agencies to continuously broadcast position information to any mobile receivers capable of interpreting the code. When either a Bluetooth-based network or a local RF network is implemented for position information, and the designated frequency and interpretation code are made available to the public, system 10 is able to correct its GPS position accordingly. Because the accuracy of such local position information is not as accurate as GPS, GPS data will always override any position calculation based on reflected GPS, re-radiated GPS, or localized position information through Bluetooth or other localized RF systems.

Communication Module

Communication module 14 is designed to manage communication continuously and uninterruptedly between system 10 and a known central facility at a remote site, and to ensure that the current location of system 10 is always available at the central facility. Given that no existing terrestrial communication network provides global coverage, module 14 must be built on a scalable, multi-platform architecture to ensure uninterrupted global communication.

Figure 6:
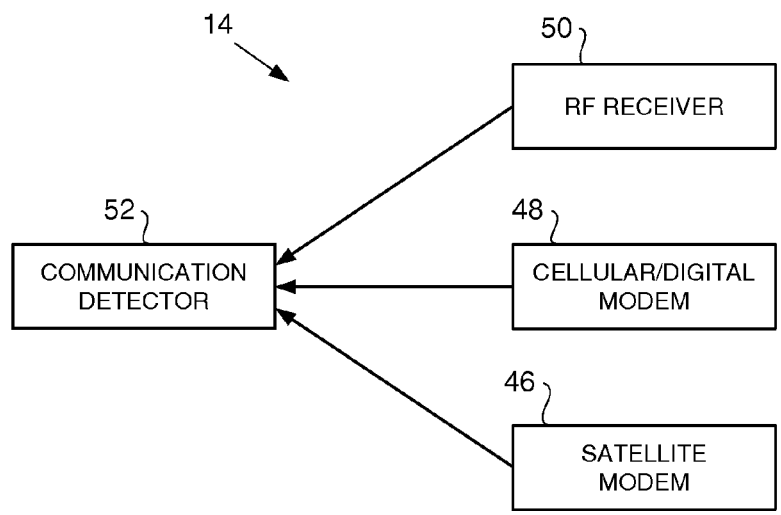
FIG. 6 is a block diagram of a communication module.

Communication module 14 comprises three components as shown diagrammatically in FIG. 6, including a scalable receiver 50 for communications through radio frequency signals (RF), a multi-band radio modem 48 for common cellular communications or wireless digital communications, and a dedicated modem 46 for satellite communications. The operation of receiver 50 and modems 48 and 46 are coordinated and controlled through communication detector 52, which may comprise a printed circuit board designed to compare incoming signals from each communication network with their corresponding protocols. Communication module 14 has a subprogram that evaluates the validity of each communication system and determines the most cost-effective mode available, and automatically switches the communication to that mode.

Communication module 14 detects the availability of a wireless communication mode and establishes the connection whenever needed through the use of communication detector 52. It always checks the availability of any local RF as this is the least expensive mode. If a local RF connection cannot be made, it opens the digital cellular channels and detects from the list of priority any existing channel for communications.

Figure 7:
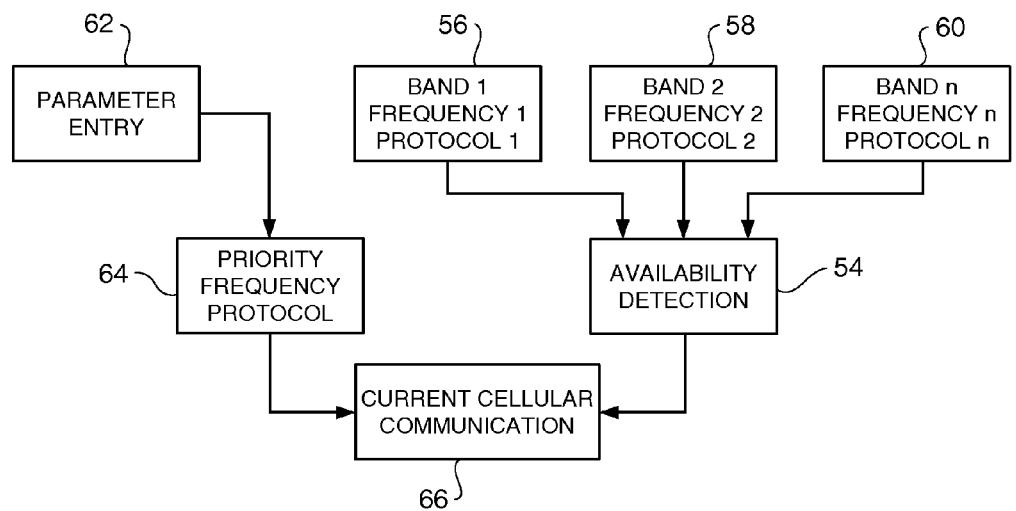
FIG. 7 is a block diagram of a multi-band cellular communication system.

The processing taking place in communication module 14 is to establish a multi-band, digital cellular connection as depicted in FIG. 7. If none of the registered digital cellular networks are available, the satellite communication is established at step 54 only when needed. Communication module 14 is capable of establishing the wireless communication through a plurality of commercial or public digital cellular networks, symbolically depicted as occurring in steps 56, 58 and 60. Because different networks vary in both frequency ranges and protocols, each network has to be registered so that its code can be correctly interpreted. The frequency range and protocol of each available network must be entered into a system registry in system 10 and a priority level is assigned. The assignment of priority levels at step 62 is based on several factors: coverage, signal strength, signal reliability, and cost. The multiple bands are evaluated at step 54 whenever system 10 requests a cellular connection. The frequency range is adjusted to receive signals within the network under evaluation. From the network of highest priority down as determined at step 64, when a network is received with sufficiently strong signals, the connection is established at step 66 and the appropriate protocol is deployed for the communication.

Local RF Communication

If a surgical asset, such as an instrument tray or surgical instrument, is to be transported within a predefined geographical area and a local RF communication network is available within the area, such as tracking the instrument tray within a hospital or other healthcare facility, communication through the local RF network might be most effective and least expensive. System 10 allows the user to take advantage of the available RF communications for the most cost-effective tracking. Due to the fact that local RF networks vary in frequency, system 10 uses a scalable RF modem so that the communication can be adjusted whenever necessary. In some embodiments, this mode, if available, is the first choice of communication for system 10. The localized RF network is activated only when system 10 is to be tracked within a specific geographical region.

The RF capability serves another important function in receiving GPS location through a transporter, instead of directly from the GPS satellites. This is possible when system 10 is attached to a container on a ship, located inside a building, stored in a warehouse, located within a vehicle or in any other enclosed structure where directly receiving GPS signals is not possible. If the vehicle, ship, building, warehouse, or other enclosed structure has an external GPS receiver and the receiver broadcasts the GPS location through an RF channel, the position information is received and the current location is updated accordingly. This introduces an additional mechanism to ensure the accuracy of location information.

For medical device tracking, the same idea applies in the situation where the vehicle is already installed with a GPS antenna mounted on the exterior. System 10 detects the GPS signals transmitted through a short-range local area network component and receives the position information directly. In this case, system 10 can be a portable device by itself or attached to any device, such as a PDA or a mobile data computer.

Alternatively, the vehicle is equipped with an external GPS antenna that receives GPS signals, and the system 10 is electrically connected to the external antenna.

Figure 8:
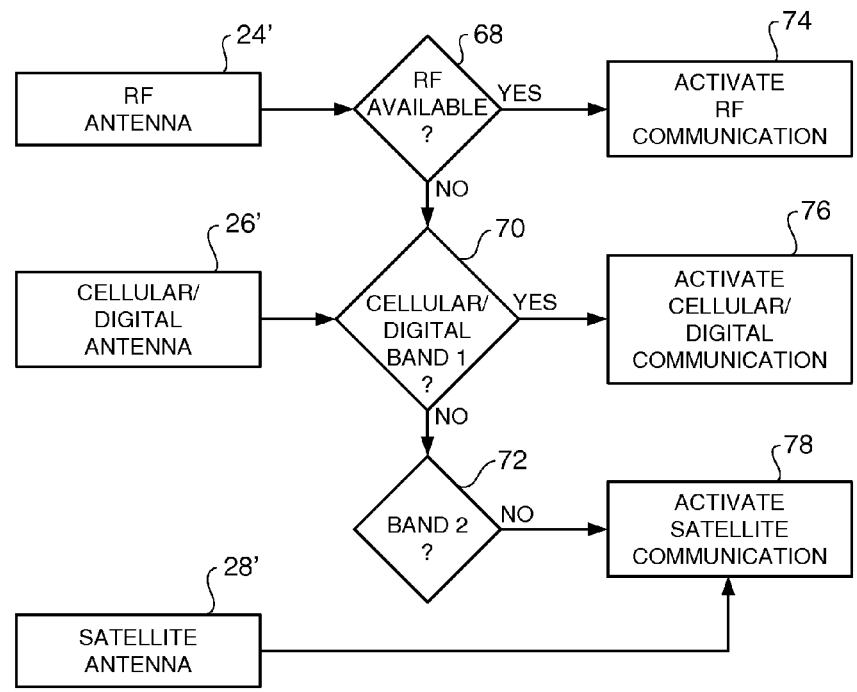
FIG. 8 is a flow chart illustrating the flow of data and control in the communication module.

In FIG. 8, communication module 14 processes data in the following manner. If a local RF network is received and connected at step 24', the communication is set at this mode and no other communication is needed as determined at step 68. RF communication is activated at step 74. If no local RF network can be connected, the multi-band cellular connection at step 26' is attempted. According to the priority level, each registered network is tested and the one with highest priority and availability is connected at step 70. The cellular/digital communication is then activated at step 76. If after all the registered cellular networks have been exhausted and no connection is made as determined at step 72, the satellite connection is established at step 28'. Satellite communication is activated at step 78.

Whenever the communication is on satellite, the communication module will continue to search for RF and cellular connection. As soon as either a local RF network is found, or a cellular network can be connected, the satellite connection is dropped and the communication re-established.

Multi-Band Cellular Communication

If a local RF network is not available for the tracking system or the surgical asset tends to be transported over a wide geographical area, a second communication mode can be made through a commercial cellular network, or wireless digital network, such as CDPD, CDMA, AMPS, GSM, Mobitex, etc. These networks tend to offer extensive coverage, although in most cases no single network offers complete worldwide coverage.

Communication module 14 utilizes an adjustable multi-band radio modem 48 so that it does not rely on any one single network to provide communication capability. A built-in sensor detects the availability of each network and establishes communication with the available network.

Communication module 14 requires a specifically designed integrated circuit board with the following processing capabilities. First, a system-setup mechanism allows the user to input as parameters (1) the frequency range, (2) the protocol, and (3) the priority level for each cellular network to be incorporated at steps 62, 64 as shown in FIG. 7. Such parameters can be transmitted wirelessly through any existing communication channel. If a new protocol is to be added to the existing list of registered networks, the user can either manually enter the parameters through a serial connection or send the parameters to system 10 remotely using any existing channel. Second, when communication module 14 is activated, it always scans from the channel of highest priority level down through the list. Third, when a channel on the priority list is scanned, the frequency is adjusted to the specific range and the protocol is interpreted accordingly. Fourth, at any point, if a channel being scanned is detected and found to be valid, the communication is set at the channel and the scanning mechanism is terminated until the channel becomes invalid at a later time.

Satellite Communication

Commercial cellular communication networks and wireless data networks suffer from their inability to provide complete global coverage. Over vast areas of deserts, forests, and oceans, one can utilize any one of the available long-range radio communication technologies. Among the available long-range radio communication technologies, satellite communications are most reliable and efficient. Communication module 14 is equipped with a satellite communication modem 46 to transmit and receive signals through communication satellites.

The use of satellite communication is required only when no other communication system is available. When detector 52 cannot establish communication through local RF radio networks, cellular networks, or wireless data networks, it activates satellite modem 46 to ensure non-interrupted communication with the central facility. The satellite communication is automatically terminated if another mode of wireless communications is established. In other embodiments, the system attempts to make contact through the use of a pager network.

Power Module

Due to the durability requirements of tracking surgical assets, system 10 is able to function continuously for an extensive period of time. In one particular embodiment, system 10 is able to operate for a minimum of one year without external recharging. Requirements for duration longer than one year can be achieved by enhancing power module 16. To achieve the objective of long durability, power module 16 utilizes an innovative power management mechanism to minimize the use of power while recharging the battery whenever possible. In particular, power module 16 is configured to switch between a sleep mode when the system 10 is stationary and a wakeup mode when the system 10 is moving.

Figure 9:
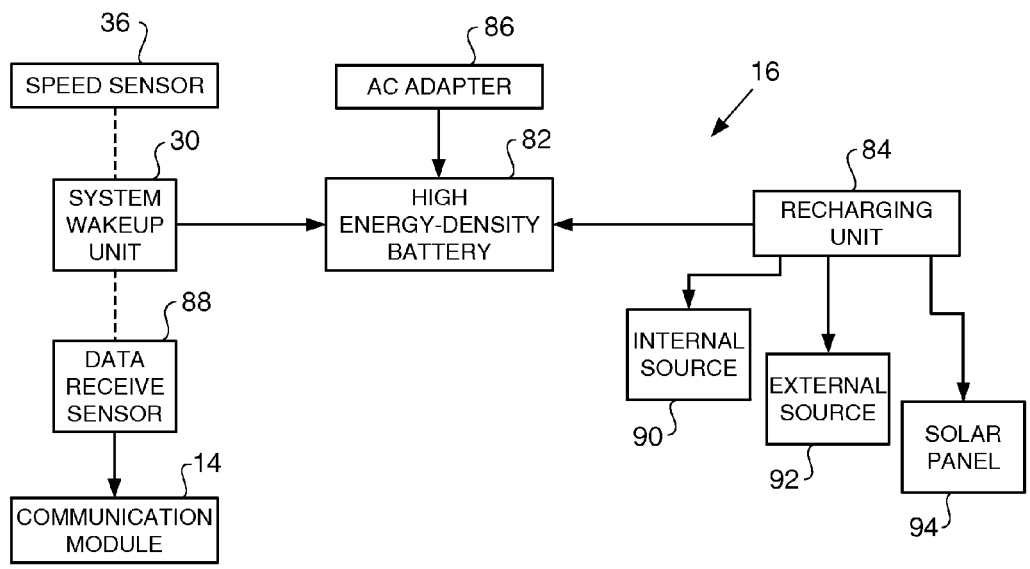
FIG. 9 is a block diagram of a power module.

Power module 16 comprises four components as diagrammatically depicted in FIG. 9, including: (1) an external system wakeup unit 80, (2) a high energy-density battery 82, (3) a self-recharging mechanism 84 using either a mechanical recharging device, a solar panel, or any device that can generate power within system 10, and (4) an external AC adapter 86 which can be used to recharge system 10 whenever any AC power source becomes available

System Wakeup Unit

The system wakeup unit 80 plays an important role in energy conservation. Unit 80 is adapted to maximize the duration of system 10 by minimizing the use of battery power. Unit 80 controls system 10 in such a way that whenever system 10 does not need to stay live, it shuts down all the components of system 10 that need not function and keeps system 10 in a sleep mode. When system 10 is in the sleep mode, only key sensors that consume the minimum amount of energy are kept active.

System wakeup sensor 80 is connected to the speed sensor 36 in the location module 12. When system 10 is not moving, speed sensor 36 remains active. When system 10 starts to move again, speed sensor 36 issues a signal to trigger system wakeup unit 80 to start functioning. In an alternative embodiment, when system 10 stops moving or comes to rest for a short period of time, speed sensor 36 issues a signal to trigger system wakeup unit 80 to start functioning.

In addition to speed sensor 36, system wakeup unit 80 is also equipped with an optional data receive sensor 88 connecting to communication module 14. Data receive sensor 88 is identical to that installed in commercial pagers and it consumes minimum energy when no communication is taking place. Data receive sensor 88 makes it possible for the central facility to activate system 10 remotely for any reason. In principle, system 10 stays dormant if it is not moving, and during the period when system 10 remains dormant, the central facility already has the current location through the last transmission, no matter how long ago it was recorded. Data receive sensor 88 allows the central facility to issue a system wakeup command and receive a current report of the location, just to make sure system 10 remains functional. In most cases, the optional data receive sensor 88 is used for system testing.

High Energy-Density Battery

A non-leaking, high energy-density battery 82, such as a specially designed lithium polymer battery or a more commonly used lithium ion battery, or any other battery that enhances the energy efficiency, may be included in system 10. Given the current battery technology and the system's effective mechanism for minimization of energy use through the control in power module 16, a power unit 82 of compact size can sustain system 10 over an entire year without the need for recharging, if system 10 stays dormant or if the communication between system 10 and the central facility is maintained at a relatively low level. Battery 82 is recharged automatically through an external AC adapter 86 and the built-in recharging unit 84.

Recharging Unit

Recharging unit 84 is implemented with any single or multiple recharging source available, depending on the use of system 10, including an external recharging source 92, an optional internal recharging source 90, and a solar power source 94. With any one or more of the recharging components are implemented, battery 82 is recharged whenever any of such components works.

The external mechanical recharging source 92 allows system 10 to be attached to any external mechanical power source, such as a windmill, a hand crank, or a motion powered piezoelectric generator. For the wind-powered recharging unit 84, the system 10 has four openings on the corners to allow for air to flow through. In each opening, a wind-driven propeller (not shown) rotates whenever air flows through. As the system 10 is attached to the surface of a container, for instance, and as the container moves during shipping, the four propellers automatically recharge power unit 16. The internal mechanical recharging source 90 uses any equipment that generates electricity whenever system 10 moves. For instance, a pendulum pulling a thin-wire spring in the internal recharging source 90 when system 10 moves may recharge battery 82 accordingly with a trickle charge. The solar recharging source connects a charging mechanism to the solar panel 94 on the surface of system 10. If system 10 is installed on the surface and receives sunshine, it automatically generates energy and passes the energy to recharging unit 84. System 10 also may utilize or incorporate an inductive charger.

Recharging unit 84 is designed to prolong the duration of system 10 over an extensive period of time. As long as recharging unit 84 remains functional, the system 10 will continue to operate without limitation.

AC Adapter

The AC adapter 86 is installed for recharging battery 82 whenever an AC power source becomes available. Even though system 10 may be running on battery 82 for an extensive period, any time the chance arises, recharging from the external power source will ensure the maximum recharging of battery 82.

Thus, it can be appreciated that as shown in FIG. 9 power module 16 is built on a high energy-density battery 82 to supply the needed power for processing and transmission of data. Battery 82 is connected to a system wake-up unit 80, an AC adapter 86, and a recharging unit 84. System wake-up unit 80 plays an important role in controlling the use of power and it shuts down the system whenever there is no motion of system 10 over a threshold time period. When system 10 is shut down, only needed sensors are kept active to minimize energy consumption. AC adapter 86 allows battery 82 to be recharged from an AC source whenever possible. Recharging unit 84 contains at least an external recharging source 92 and an internal recharging source 90, and also connects to a solar panel 94 attached to the surface of system 10. The management of power use is depicted in FIG. 10.

Figure 10:
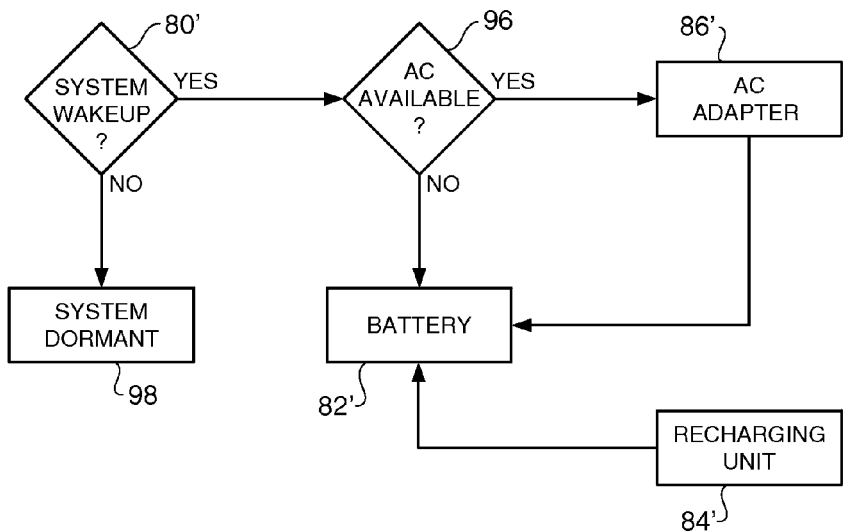
FIG. 10 is a flow chart illustrating the flow of data in the power module.

As diagrammatically depicted in FIG. 10 at step 84', recharging unit 84 in power module 16 constantly recharges battery 82 at all times if the source is available. Neither internal recharging unit 90 nor the external recharging unit 92 are active when system 10 is stationary. If the surface of system 10 is not exposed to the sun, the solar-power recharging unit 94 does not operate either. Because system 10 is not moving, minimal power is consumed and battery 82 can last for an extended long period by lying in a dormant state at step 98. System wake-up unit 80 determines at step 80' if system 10 needs to be kept in the sleep mode. If system 10 is not moving, system wake-up unit 80 shuts down system 10 to conserve energy. If system 10 is up, wake-up unit 80 detects if an AC source is determined to be available at step 96 to recharge system 10. If no AC source is determined to be available at step 96, then system 10 continues to operate under battery power only. If an AC source is available, AC adapter 86 is connected to battery 82 at step 86' and battery 82 is charged at step 82'.

Antenna Module

Figure 11:
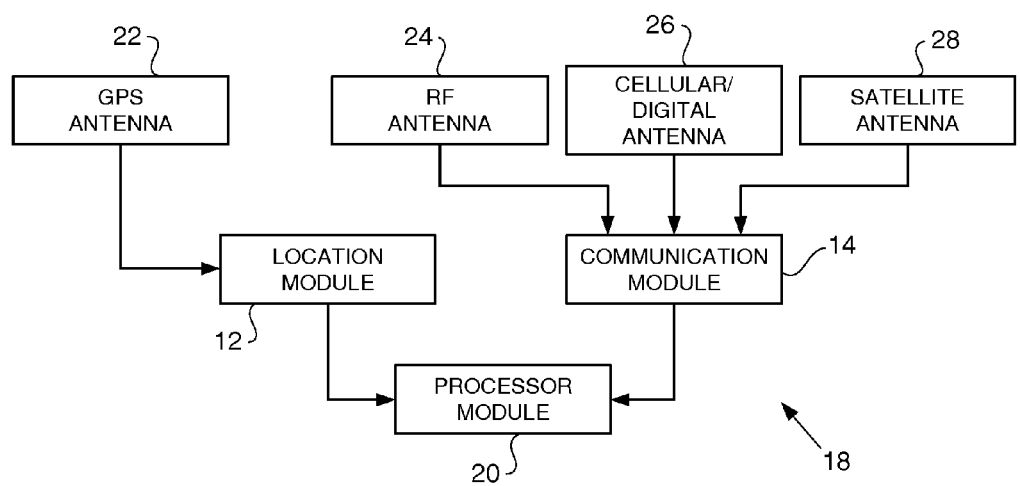
FIG. 11 is a block diagram of an antenna module.

Antenna module 18 as shown in FIG. 11 contains a set of antennas, including the GPS antenna 22, antenna 24 for low frequency RF, antenna(s) 26 for the multi-band terrestrial wireless communication networks, and antenna 28 for satellite communications. Antenna module 18 is equipped with an antenna controller (not shown) that constantly checks the validity of signals from any of the antennas to determine the availability of communications. All the antennas are mounted on the surface of system 10 to maximize effectiveness of reception and transmission.

GPS Antenna

GPS antenna 22 receives satellite signals from the GPS constellation. If GPS signals are strong enough to get the position, the data will be used to update the location of system 10. GPS antenna 22 is usually mounted on the top cover of the shipping container, instrument tray case, or tracked object to maximize its exposure to GPS satellites. If system 10 is mounted on the side, then antenna 22 is moved to the side of the shipping container, instrument tray case, or tracked object wherever most appropriate.

System 10 may be attached to an instrument tray within a vehicle, a container on a ship, stored inside a warehouse, located within a building, or in any enclosed structure where GPS signals cannot be received directly. In such cases, if the vehicle, ship, warehouse, building, or other structure has installed an external GPS and reradiate the GPS signals to any GPS receivers within the structure, the GPS antenna can continue to receive the accurate position and update the location of system 10. This ensures that even when system 10 is not moving by itself, it still can update its location.

RF Antenna

RF antenna 24 can be mounted on the side of system 10 of the shipping container, instrument tray case, or tracked object. Antenna 24 is to be used for communications with the available RF channel. Antenna 24 is adjustable for different frequencies of communication. For instance, when the system is installed in a hospital or other healthcare facility, RF antenna 24 must be adjusted to maximize the communication through the specific channel.

Cellular Antennas

Antennas 26 for the multi-band terrestrial communications through either the commercial cellular networks, or wireless digital networks, can be mounted on the top or any side of system 10 of the shipping container, instrument tray case, or tracked object, depending on how system 10 is to be attached to the surgical asset.

Satellite Antenna

Antenna 28 for satellite communication is also mounted on the top of system 10, depending on how system 10 is to be attached to the asset.

Thus, in summary, it can be appreciated that the surface of the system is covered with four sets of antennas controlled by an integrated circuit board, GPS antenna 22, antenna 24 for local RF, antenna(s) 26 for cellular networks, and antenna 28 for satellite communications. GPS antenna 22 constantly detects and receives GPS signals, both directly from the GPS satellites if the surface is exposed to the sky, and indirectly from reflected signals and re-radiated signals. The received GPS signals are evaluated for validity in the location module 12. Local RF, cellular networks, and satellite antenna are all connected to the communication module 14. The exchange of location information received from GPS antenna 22 and the wireless communications through any of the existing mode takes place in the processor module 20.

Processor Module

Figure 12:
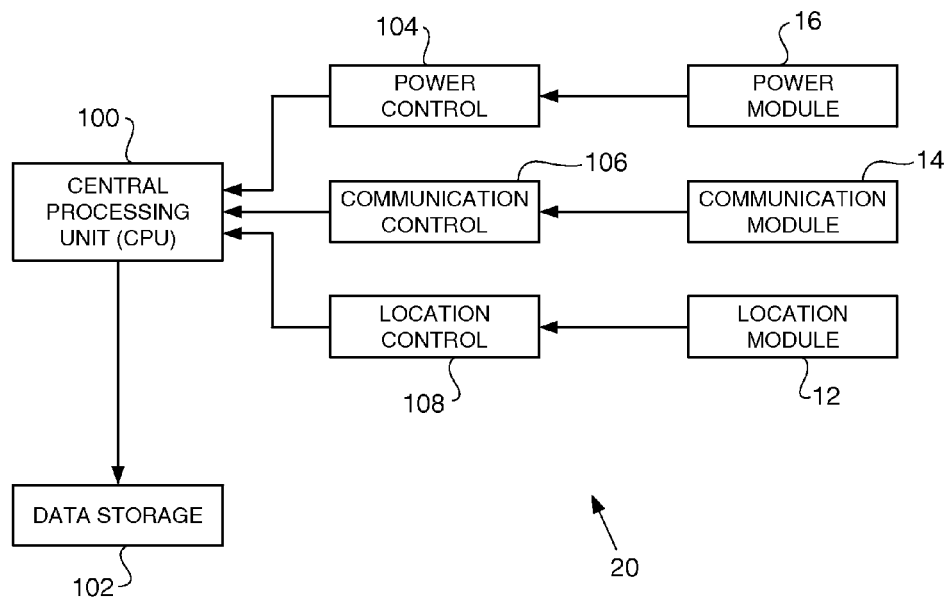
FIG. 12 is a block diagram of a processor module.

Processor module 20 as shown in FIG. 12 is the core of system 10 that controls data input/output, storage, manipulation, and the flow of data between different modules. Processor module 20 comprises a high-grade central processing unit 100 (CPU) with a flash ROM and a data storage device 102 that can be used to store location information over an extensive period. As examples, the data storage device 102 may be a hard drive, a micro hard drive, or a flash storage device. In the embodiment depicted in FIG. 12, data storage 102 is a removable memory card.

Power Control

A power control interface 104 couples CPU 100 with power module 16. When speed sensor 36 indicates no movement of system 10, all the components in system 10 are shut down except for two sensors, speed sensor 36 and system wakeup sensor 80. If speed sensor 36 detects motion of system 10, location module 12 is activated to update the position using either the GPS reading, if GPS is valid, or to receive the current location information that is broadcast through the RF, if such system is available. Otherwise, motion sensor 32 is used to calculate the current location from the three dimensional gyro 34 and speed sensor 36. Whenever the speed drops to zero, the system 10 returns to the dormant stage at step 98, shown in FIG. 10, and leaves on speed sensor 36 and system wakeup sensor 80.

Battery recharging is activated automatically. If the external AC power source is connected, then the battery is recharged automatically. If any other recharging mechanism becomes available, the battery is automatically recharged until either the AC power source is connected or the battery is fully charged.

An option function can be included to issue a warning message to the central facility when the power drops below a pre-determined threshold. In this case, if the recharging sources successfully recharge battery 82 back to an acceptable level, another message will be issued to notify the central facility to erase the low power alert.

Communication Control

A communication control interface 106 couples CPU 100 with communication module 14. When the system 10 is in the dormant mode, no communication is needed. As soon as system 10 is activated by wakeup sensor 80, system 10 starts to establish communication. The function of communication control interface 106 determines the most cost-effective, available mode of communication. If local RF is available, the communication between system 10 and the central facility uses the RF pursuant to control by the processor's 100. Otherwise, system 10 will try to establish communication through any of the multi-band cellular networks or wireless data networks. Only if none of the above communication modes can be successfully made, will system 10 activate the satellite communication channel. While the communication is established at any level, system 10 continues to detect the communication at a lower level, and switch to a lower level if it becomes available pursuant to the processor module 20.

Location Control

A location control interface 108 couples CPU 100 with location module 12. The current location of system 10 is always registered in processor module 20. When system 10 was initialized, the initial location is registered immediately. Whenever a valid location update is received, either from GPS, from RF, or calculated by the built-in motion detector 32, the current location is updated and saved in memory 102. Whenever the system detects a valid GPS signal, the current location is also updated. At any moment, location control keeps the current location to be sent to the central facility upon request.

Thus, it can now be summarized that processor module 20 controls the flow of data throughout system 10, manages the calculation of location, and determines the transmission of data to the available communication mode. Processor module 20 receives input of location information from location module 12 and keeps tracks of the current position, manipulates the input and output of data elements thought the communication mode, and issues commands to control the power use and system shutdown. Processor module 20 saves all the operational parameters in storage memory 102, and retrieves current position from storage 102 upon system requests.

The system 10 employs a combination of long-range and short-range asset location systems, such as a GPS-based system combined with an RF-based system. The short-range system regularly activates itself, or is remotely polled, to determine if the surgical asset is within range of the short-range transceivers, and the long-range system is activated to determine the location of the surgical asset when it is outside the range of the short-range transceivers. In at least some embodiments, the surgical asset is equipped with both RFID and GPS-based receiving equipment. The receiving equipment may be part of a stand alone unit or part of a transceiver. In other embodiments, the surgical asset is equipped with radio-wave transmission equipment and microwave transmission equipment. Again, the transmission equipment may be part of a stand alone unit or part of a transceiver.

One particular embodiment of the system 10 uses multiple wireless technologies (RFID, GPS, CDMA, etc.) in single tag to facilitate asset tracking and locating, and is particularly advantageous in such areas as manufacturing plants, during delivery to healthcare facilities, and while stored within the healthcare facility.

In yet another embodiment, the system 10 includes a medical device readiness module as is explained in greater detail below.

In some embodiments, the system 10 utilizes the real-time location system (RTLS). RTLS does not require line-of-sight (indoor/outdoor) but utilizes RF or RFID tags. These tags may conform to the ANSI 371/INCITS 371 standards, known to those of skill in the art, including transponder tag, antennae, and transceiver with decoder or some other similar standard. This type of system is typically capable of XY location accuracy within 3 to 300 meters. Of course, more readers enable greater accuracy.

In some embodiments, the initial RF tag is attached to the surgical asset during beginning of assembly. Later, the RF tag is integrated into the GPS system on the asset. In this way, the surgical asset is trackable throughout plant grounds (indoor and outdoor), and the system facilitates finding the asset (warehouse, during delivery, at the hospital, etc.) as needed. A locator, such as a handheld PDA, can be used to locate the surgical asset. The same RTLS infrastructure can be used for facility management, surgical planning, warehouse management, distribution, logistics, etc.

The RTLS/RFID tags can be programmed to emit a signal periodically, such as every several hours, as selected by the operator, and when in the presence of a reader would update the database with the asset's location.

Figure 13:
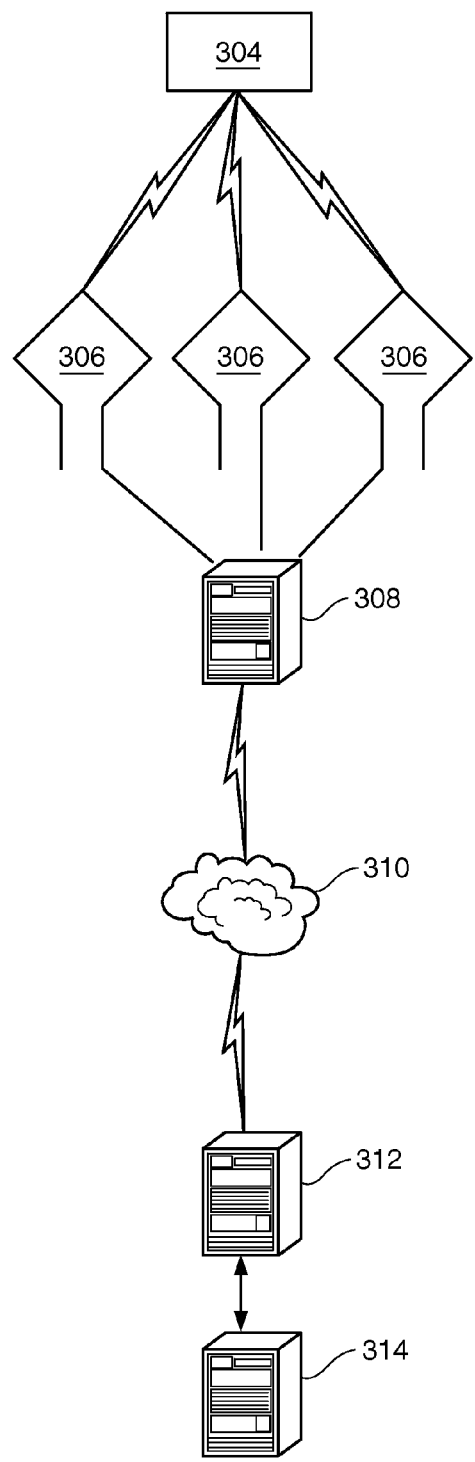
FIG. 13 is a schematic of a real-time location system for tracking medical devices.

FIG. 13 depicts a block diagram of an RTLS system in accordance with one particular embodiment. In this figure, an identifier tag, such as an RFID/RTLS tag, is attached to a surgical asset 304. As examples, the surgical asset may be a sterilization case, an instrument, or an implant, such as an orthopaedic implant. This tag communicates with antennas 306, which are in turn connected to communicate with location application server 308. While three representative antennas 306 are shown, a typical installation includes many antennas, so that an RTLS tag can be located anywhere within the covered property. The tags can be set to broadcast an asset identification number, or other asset identifier, at set intervals (e.g., every 10 minutes, every hour, etc.)

Location application server 308 includes software having a triangulation algorithm, as known to those of skill in the art, for locating the surgical asset 304 within the area served by antennas 306. Location application server 308 communicates over network 310, which can be the Internet or another public or private network, with central location server 312. Typically, there also may be one or more firewalls, not shown, through which the communications are made. Location information may be encrypted and secure at all times during transmission and storage. Central location server 312 includes a database that stores the last known location of each surgical asset. External system 314 is connected to communicate with central location server 312, so that the asset location information can be used for any appropriate purpose.

Additionally, a GPS compliant system is attached to the surgical asset. Assisted GPS utilizes cellular network to reduce GPS search time to seconds versus minutes. Special software, known to those of skill in the art, is required for both transponder and transceiver/decoder. The GPS system is typically capable of XY location accuracy within 5 to 30 meters.

Figure 14:
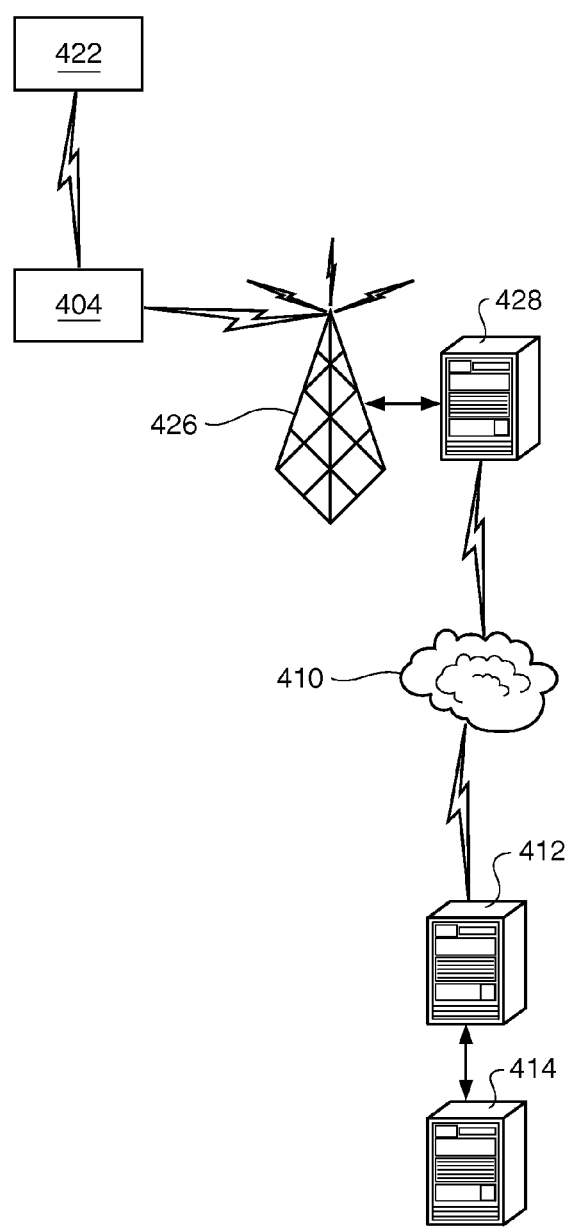
FIG. 14 is a schematic of a real-time location system for tracking medical devices using global positioning sensors.

FIG. 14 depicts a block diagram of the GPS-based system. In this figure, a GPS receiver and transceiver unit, typically a cellular-telephone-based transceiver, is attached to surgical asset 404. The GPS receiver receives location data from satellites 422, and can thereby determine its current location. The transceiver communicates with a local base station 426, by which the location information is transmitted to location application server 428. As is known in GPS-based systems, the transceiver can be remotely activated, using base station 426, and the current location information can be polled from the GPS receiver.

Location application server 428 communicates over network 410, which can be the Internet or another public or private network, with central location server 412. Typically, there also may be one or more firewalls, not shown, through which the communications are made. Location information may be encrypted and secure at all times during transmission and storage. Central location server 412 includes a database that stores the last known location of each surgical asset. External system 414 is connected to communicate with central location server 412, so that the asset location information can be used for any appropriate purpose.

In the GPS-based system, the location application server 428 may perform asset location polling. Unsold surgical assets, unshipped surgical assets or other surgical assets for which up-to-date location information is needed can be polled when their last known location is a selected number of hours old. Asset location polling can be tied to surgical asset event status (build, delivered, sold, particular surgical set required, etc.).

Figure 15:
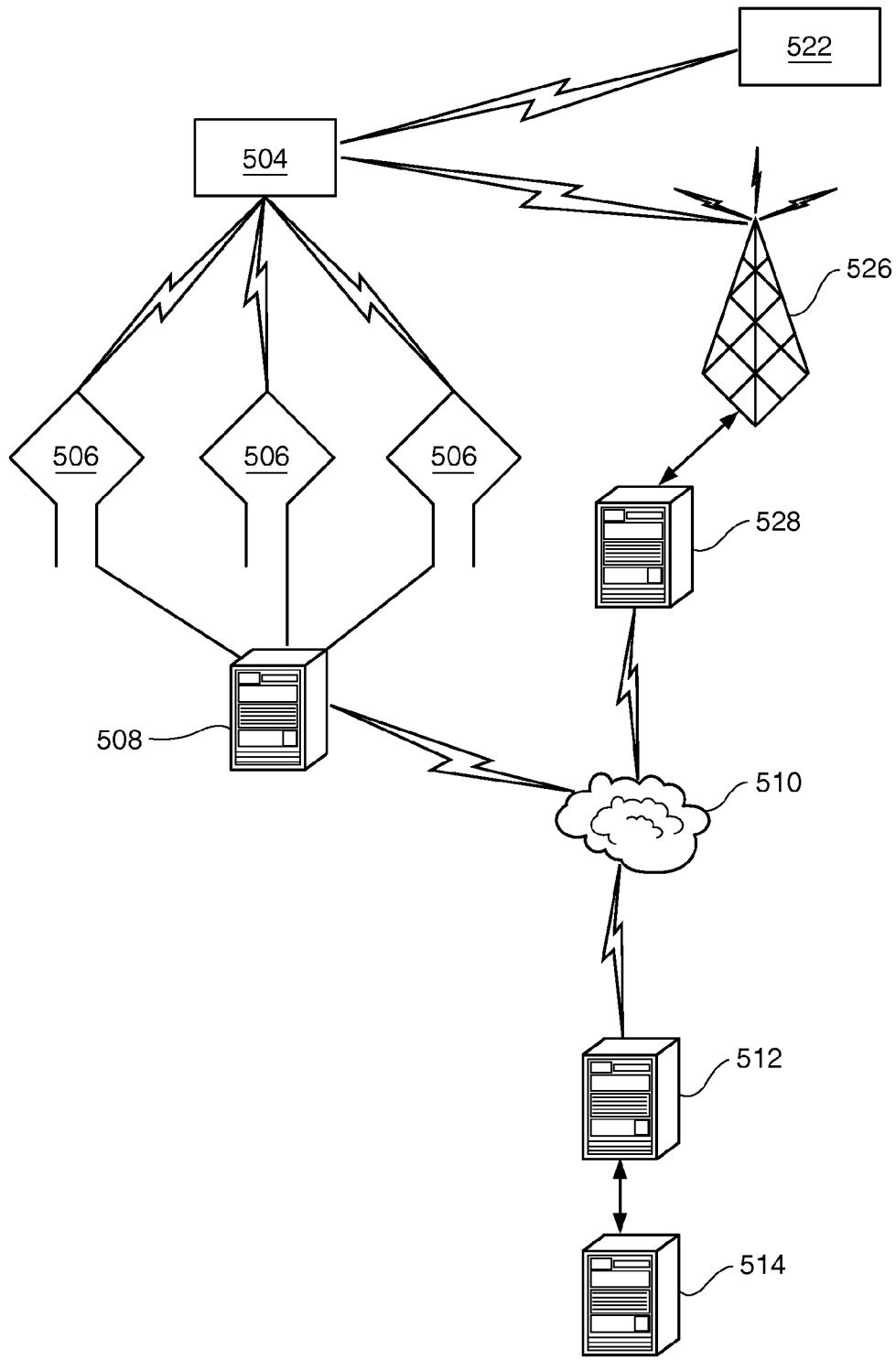
FIG. 15 is a schematic of a real-time location system for tracking medical devices using global positioning sensors and radio frequency identification.

FIG. 15 depicts a block diagram of a combined system, including both RTLS/RFID and GPS-based location systems. In this figure, a GPS receiver and transceiver unit, typically a cellular-telephone-based transceiver is installed in surgical asset 504. The GPS receiver receives location data from satellites 522, and can thereby determine its current location. The transceiver communicates with a local base station 526, by which the location information is transmitted to location application server 528. As is known in GPS-based systems, the transceiver can be remotely activated, using base station 526, and the current location information can be polled from the GPS receiver.

Location application server 528 communicates over network 510, which can be the Internet or another public or private network, with central location server 512. Typically, there also may be one or more firewalls, not shown, through which the communications are made. Location information may be encrypted and secure at all times during transmission and storage. Central location server 512 includes a database that stores the last known location of each surgical asset.

An identifier tag, such as an RFID/RTLS tag, is installed also in surgical asset 504. This tag communicates with antennas 506, which are in turn connected to communicate with location application server 508. While three representative antennas 506 are shown, a typical installation includes one or more antennas, so that an RTLS tag can be located anywhere within the covered property. The tags can be set to broadcast an asset identification number, or other asset identifier, at set intervals (e.g., every 30 minutes, every hour, etc.).

Location application server 508 includes software having a triangulation algorithm, as known to those of skill in the art, for locating the surgical asset 504 within the area served by antennas 506. Location application server 508 communicates over network 510, which can be the Internet or another public or private network, with central location server 512. Typically, there also may be one or more firewalls, not shown, through which the communications are made. Location information may be encrypted and secure at all times during transmission and storage. External system 514 is connected to communicate with central location server 512, so that the asset location information can be used for any appropriate purpose. The asset location server 508 may conduct asset location polling at discrete intervals.

The combination system allows surgical assets to be tracked in transit from the assembly plant to their end destination via GPS. Surgical assets can then be tracked by GPS on a national scale or by RF once they reach suitably-equipped locations, such as a hospital or other healthcare facility, point-of-assembly, warehouse, etc.

Figure 16:
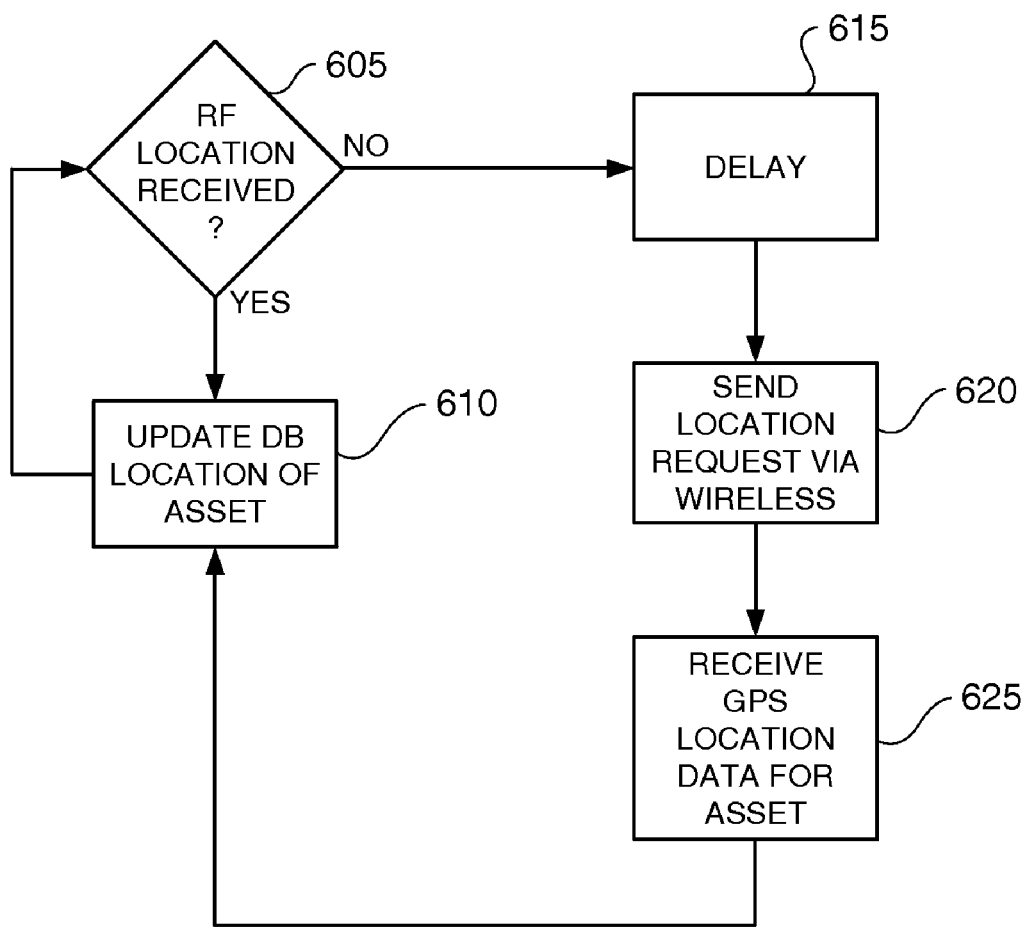
FIG. 16 is a flow chart illustrating database storage of location information.

FIG. 16 depicts a flowchart of a process for updating a location database. Here, the central location server periodically receives updates of the location of a surgical asset, generated by an automatic signal sent by the RTLS tag of the asset. When the RF-generated location information is received (step 605), the asset location database is updated to reflect the current location of the asset (step 610). If no RF-generated location information is received (step 605) after a predetermined delay (step 615), which is typically between one hour and one day, the central location server generates a location request, which is transmitted over the network to be delivered to the asset over a wireless network, typically a wireless telephone network (step 620). The asset receives the request, determines its current location based on the GPS system, and responds via the wireless network. The central location server will receive the GPS-based location information (step 625). When the GPS-based location information is received, the asset location database is updated to reflect the current location of the asset (step 610).

Some specific advantages of a system as described include tying GPS and RTLS together to allow for "smart" connections utilizing the lower cost medium when available. The tag can augment and leverage GPS systems. RTLS can later be expanded to locate instruments, instrument trays, instrument tray cases, etc. at hospitals, surgical centers, and other healthcare facilities.

Figure 17:
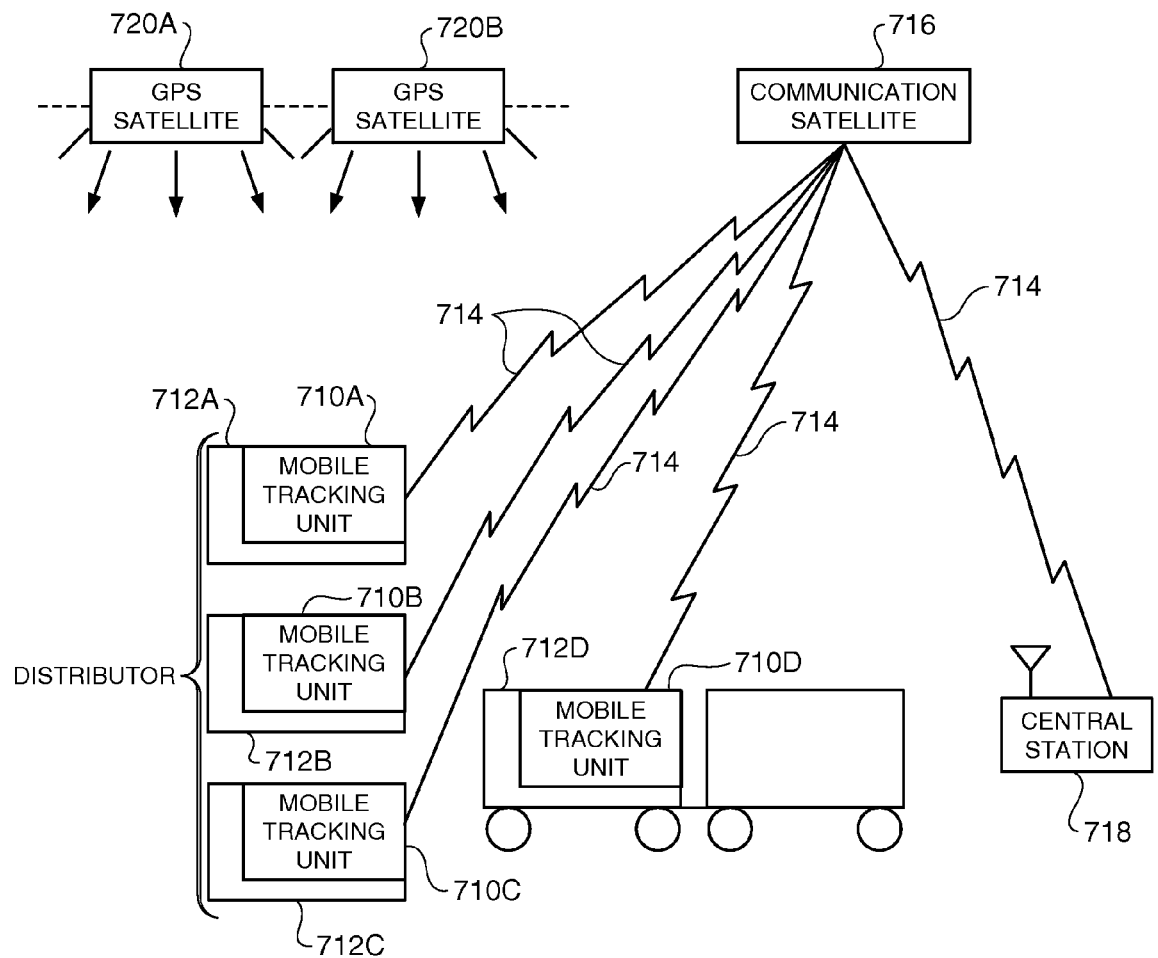
FIG. 17 is a schematic illustrating mobile tracking units that employ navigation signals from a GPS satellite constellation.

FIG. 17 illustrates mobile surgical assets that employ navigation signals from a GPS satellite constellation although, as suggested above, other navigation systems can be used in lieu of GPS. A set of mobile surgical assets 710A-710D are installed in respective mobile units 712A-712D. A communication link 714, such as a satellite communication link through a communication satellite 716, can be provided between each mobile surgical asset (hereinafter collectively designated 710) and a remote central station 718 manned by one or more operators and having suitable display devices and the like for displaying location and status information for each surgical asset. Communication link 714 can be conveniently used for transmitting asset conditions or events measured with suitable sensing elements. Communication link 714 may be one-way (from mobile surgical assets to remote central station) or two-way. In a two-way communication link, messages and commands can be sent to the surgical assets, thereby further enhancing reliability of the communication. A constellation of GPS satellites, such as GPS satellites 720A and 720B, provides highly accurate navigation signals that can be used to determine asset location and velocity when the signals are acquired by a suitable GPS receiver.

Figure 18:
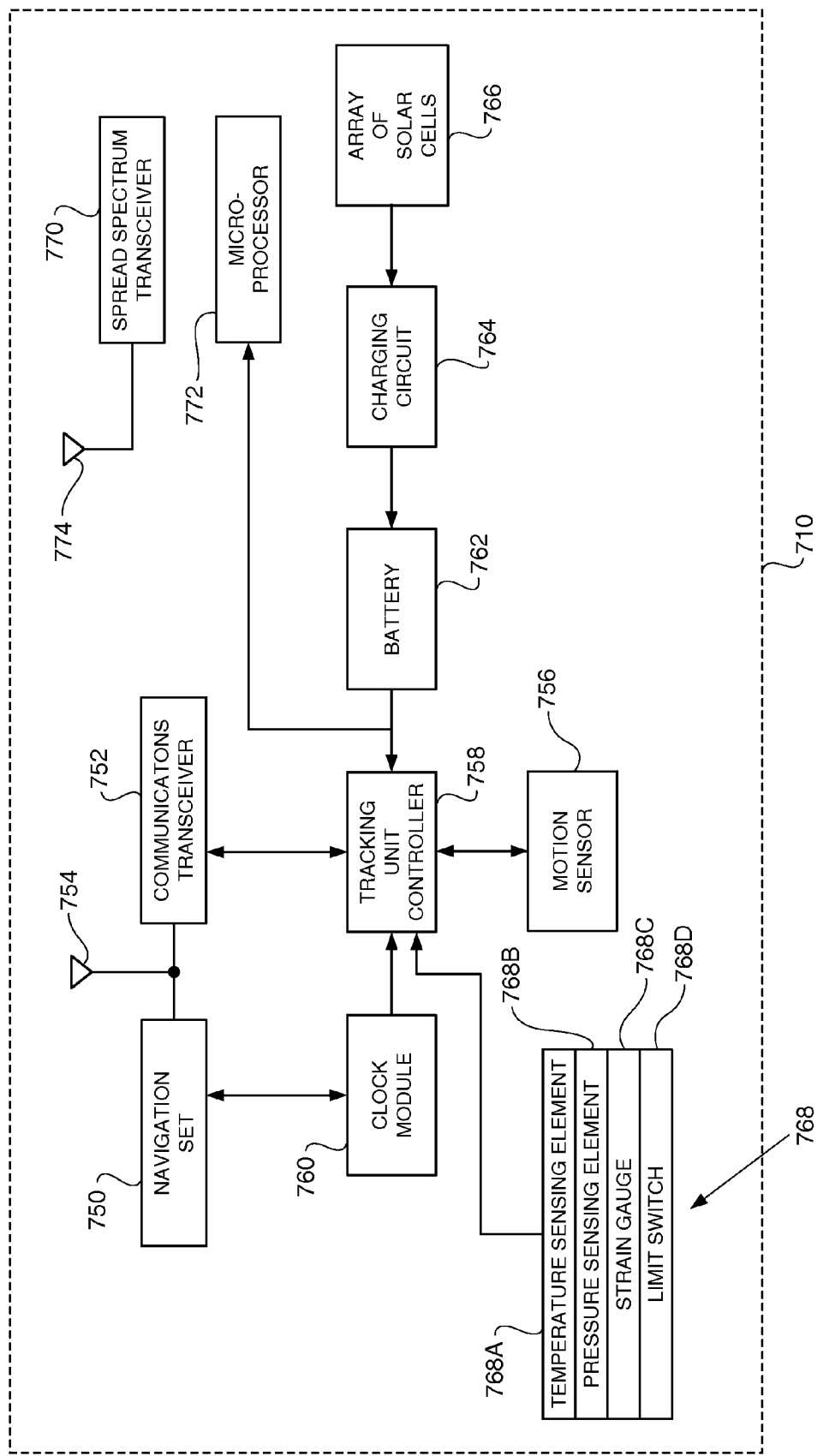
FIG. 18 is block diagram illustrating a mobile tracking unit that includes a navigation set capable of generating data substantially corresponding to the asset location.

FIG. 18 shows a mobile surgical asset 710 that includes a navigation set 750 capable of generating data substantially corresponding to the asset location. Choice of navigation set depends on the particular navigation system used for supplying navigation signals to the mobile surgical asset. In one particular embodiment, the navigation set is a GPS receiver such as a multi-channel receiver; however, other receivers designed for acquiring signals from a corresponding navigation system may alternatively be employed. For example, depending on the asset location accuracy measurements, the navigation set may comprise a Loran-C receiver or other such navigation receiver. Further, the navigation set may conveniently comprise a transceiver that inherently provides two-way communication with the central station and avoids the need for separately operating an additional component to implement such two-way communication. Briefly, such transceiver would allow for implementation of satellite range measurement techniques whereby location of the asset is simply determined at the central station by range measurements to the asset and the central station from two satellites whose position in space is known. In each case, the power consumed by the navigation set imposes a severe constraint for reliable and economical operation of the mobile surgical asset in assets which do not have power supplies, such as shipping containers, railcars used for carrying cargo and the like. For example, typical present-day GPS receivers generally require as much as two watts of electrical power. In order for the GPS receiver to provide a location fix, the GPS receiver must be energized for some minimum period of time in order to acquire sufficient signal information from a given set of GPS satellites to generate a navigation solution. A key advantage of the present invention is the ability to substantially reduce the energy required by the mobile surgical asset by selectively reducing the activation or usage rate for the navigation set and other components of the mobile surgical asset. In particular if, during times when the vehicle is stationary, the activation rate for the navigation set is reduced, then the energy requirement of the mobile surgical asset can be substantially reduced, for example, by a factor of at least about one hundred.

Mobile surgical asset 710 also includes a communications transceiver 752 functionally independent from navigation set 750. If the navigation set comprises a transceiver, then the function of transceiver 752 can be performed by the transceiver of navigation set 750. Both, transceiver 752 and navigation set 750 are activated by a controller 758 which, in turn, is responsive to signals from a clock module 760. Transceiver 752 is capable of transmitting the asset location data by way of communication link 714 (FIG. 17) to the central station and receiving commands from the central station by way of the same link. If a GPS receiver is used, the GPS receiver and the transceiver can be conveniently integrated as a single unit for maximizing efficiency of installation and operation. One example of an integrated unit is the Galaxy Inmarsat C/GPS integrated unit, which is available from Trimble Navigation Limited, Sunnyvale, Calif., and is conveniently designed for data communication and position reporting between the central station and the mobile surgical asset. A single, low profile antenna 754 can be conveniently used for both GPS signal acquisition and satellite communication.

A low power, short distance radio link permits joining the nearby mobile surgical assets in a network to conserve power and maintain high reliability and functionality of such network. The surgical asset 710 may include one or more power sources 762 (which may be charged from an array of solar cells 766 through a charging circuit 764), GPS receivers 750, communications transceivers 752, and various surgical asset sensors 768A-768D. As examples, the surgical asset sensor 768 may be a temperature sensor, pressure sensor, strain gauge, limit switch, or instrument readiness circuit or switch, which will be explained in greater detail below. Each surgical asset includes a low power local transceiver 770 and a microprocessor 772. Microprocessor 772 is interfaced to all of the other elements of the surgical asset and has control over them. Transceiver 770 may be a commercially available spread spectrum transceiver such as those currently utilized in wireless local area networks. Spread spectrum transceiver 770 is equipped with its own low profile antenna 774.

Forward and reverse (surgical asset to central station) channels are used for communication between the surgical assets and the central station. In the protocol depicted below, flags that occur in the data are not used. This is ensured by using bit stuffing (or bit escaping). This increases the traffic load by a factor of approximately 63/62. An exemplary protocol for the forward channel frame structure is as follows:

| F | ADDR | FC/C | C | DATA | CHNL | EC | F |
|---|------|------|---|------|------|----|----|

In the above frame structure, F is an 8-bit flag. ADDR is an identification number of an addressed unit comprising 20 bits, 19 for the address with one bit reserved. FC/C is a frame counter for forward control link. A first bit denotes presence of the counter. A zero indicates no counter is present, while a one indicates that the next twenty bits are the counter bits. C is a control field which specifies the message type; e.g., a zero specifies a polling message and it is understood that no control field bits follow a zero, while a one specifies another type message specified in the next three bits.

DATA specifies the future time for the addressed unit to start its response transmission. This could be keyed to GPS time or it could be keyed in another way, such as to a counter based on the end flag epoch of a correctly received forward control frame. CHNL is the narrow band channel on which the addressed unit will respond. The channel field contains eight bits. Bits 1-7 are used to specify the channel number. Bit 8 is reserved. It is normally zero. If the system is to expand beyond 128 channels, then bit eight can be set to a one and the field interpreted as extended by a present number of bits. EC is an error detection code formed over the ADDR through CHNL fields.

As a quick check on the feasibility of such control system, assume that there are A assets, that the forward channel is running in just the sequential polling mode, that the FC/C counter is not used, that the DATA field is twenty bits, that the CHNL field is eight bits, and that the error checking field is sixteen bits long. The time in minutes, T, to complete a sequential polling, is then approximately:

$$T = 63/62 \times (82 \times A)/(6 \times 10^5)$$

assuming that ten kilobits per second can be passed over the forward control link. If A is on the order of 100,000, then T is on the order of fifteen minutes.

The surgical asset receivers need not continuously monitor the forward control link; rather, they can extrapolate to the next minimum time to the repeat of interrogation and listen at just before that epoch. If there has been much traffic other than polling, the surgical asset receiver can determine, from what the polling number is, whether to stay on or go back into standby or "sleep" mode until just before the minimum time to poll from that point.

An exemplary protocol for the return channel has the following frame structure:

| SYNC | ID | C | DATA | FEC | EC | F |
|------|----|----|------|-----|----|----|

In the above frame structure, SYNC is a synchronization preamble to establish carrier synchronization, symbol boundaries, and epoch via a unique word of low autocorrelation sidelobes. ID is the asset tracker identification field. C is the control field which designates message: type. If the first bit is zero, then the message is conveying length in response to a polling message on the forward link. The length of the message is coded in binary from MSB to LSB (most significant bit to least significant bit). The number of bits need not be fixed as the number can be determined by counting backwards from the ending flag. FEC is an optional forward error correcting field. It is not present if the first bit is zero. EC is an error detection code formed over the ID field through the FEC field.

Figure 19:
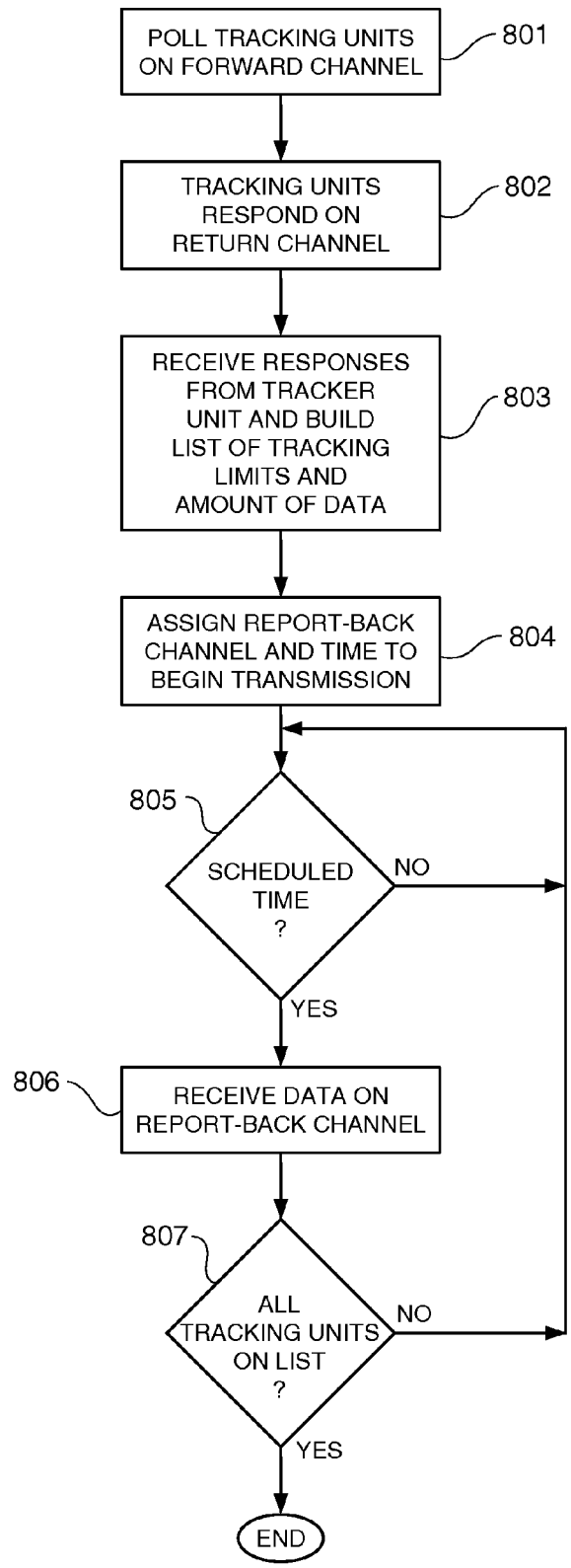
FIG. 19 is a flow chart for tracking mobile units.

The protocol functions as illustrated in the flow diagram of FIG. 19, to which reference is now made. The forward control channel is run ahead of the reporting surgical assets. The forward control channel determines, from responses received, which asset is prepared to transmit and how much that asset will transmit. This could be a wide range. For example, the mutter control master unit might transmit all the data for all of its constituent surgical assets when it is itself polled. This would save re-synchronizing.

The process begins by the central station polling the surgical assets in the narrow band forward channel at step 801. The surgical assets answer on the narrow band return or service channel in fixed frame format at their assigned slot at step 802. The central station receives the responses from the surgical assets at step 803 and determines which of the surgical assets is prepared to transmit data and how much data those surgical assets will transmit. Based on the list generated at step 803 regarding the amount of data to be sent and by which surgical assets, the central station assigns a report-back channel and a time to begin transmission. The scheduled time and report-back channel are transmitted to the surgical assets on the forward channel at step 804. There may be a plurality of narrow band report-back channels that may be appropriately multiplexed among the surgical assets transmitting data to the central station to conserve frequency spectra. When a scheduled time for report-back by a surgical asset occurs as determined at decision step 805, the central station monitors the assigned report-back channel at step 806. If the central station must pause or wait before proceeding with scheduling, it may send repeated flags on the forward channel as an accepted inter-frame flag-fill mode. After each surgical asset in the list reports, a check is made at decision step 807 to determine if all the surgical assets which are on the list to report have reported and, if not, the process loops back to decision step 805. When all data to be sent have been received, the process ends.

FIG. 20 illustrates data flow of location data for surgical assets. FIG. 20 illustrates a database 910, a warehouse 920, a hospital 930, a distributor 940, and a communications network 950. While only one database is shown in FIG. 20, those having ordinary skill in the art would understand that greater or fewer databases may be used. The hospital includes a central supply 932, an operating room 934, and an operating room staging area 936. In the depicted embodiment, the surgical assets originate at the same location as database 910 but they could equally originate at other locations. From the point of origin, the surgical assets may be transported to the warehouse, provided to the sales representative, or transferred to the hospital 980. From each of these locations, location data can flow along the communications network 950 back to the database for storage of surgical asset location information. In some embodiments, the surgical asset location information can identify discrete locations, such as the central supply 932, the operating room 934, or the operating room staging area 936.

Figure 22:
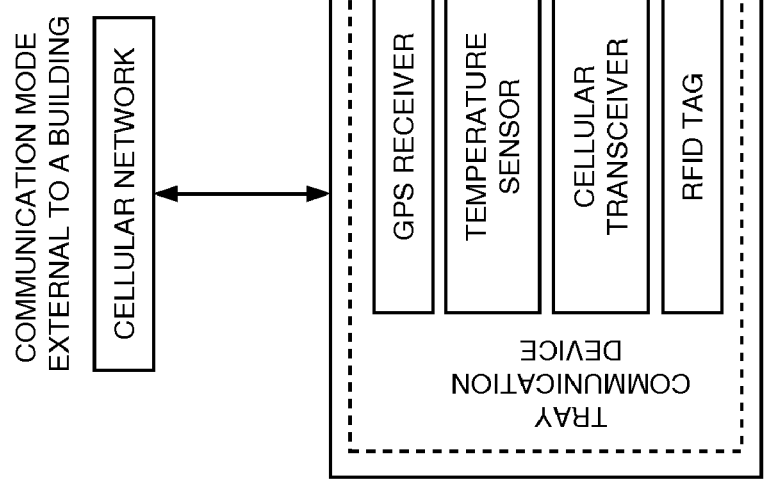
FIG. 22 is a block diagram illustrating a second mode of data flow.
Figure 21:
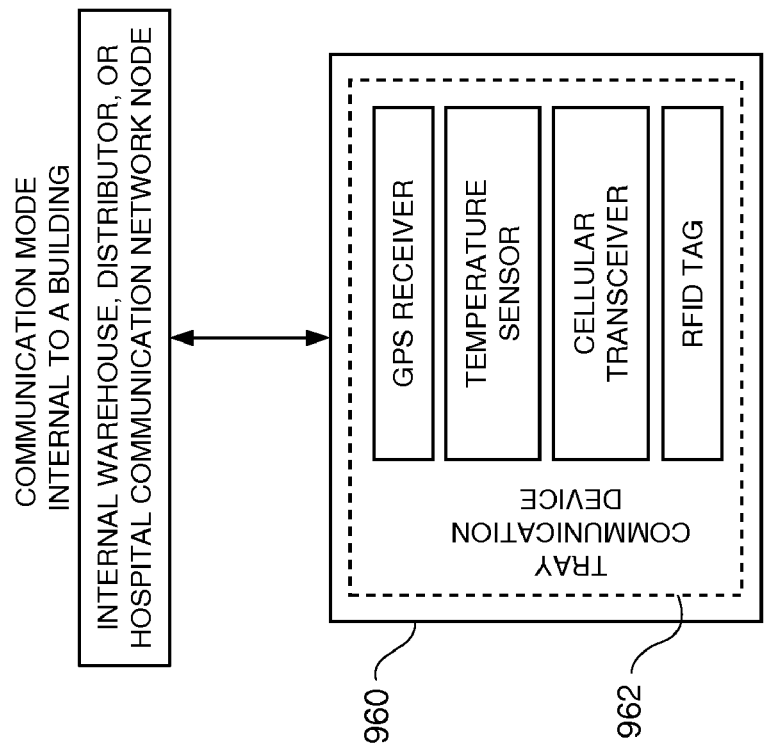
FIG. 21 is a block diagram illustrating a first mode of data flow.

FIGS. 21 and 22 illustrate a surgical asset 960 having a tray communication device 962. The surgical asset 960 and the tray communication device 962 form a portion of a system for tracking surgical assets. In the depicted embodiments, the surgical asset 960 is a sterilization case. The tray communication device 962 may include a GPS receiver, a temperature sensor, a cellular transceiver, and an RFID tag. The tray communication device 962 also may include a module or circuit to gauge surgical asset readiness.

FIG. 21 illustrates a first mode of data flow. In the first mode, data is communicated internally within a building, such as the hospital 930 or warehouse 920. The data is communicated from the tray communication device 962 to a database for storing location information. The database may be located within the building such that data travels directly from the tray communication device 962 to the database. Otherwise, data is communicated from the tray communication device 962 to a node point connected to the building and from the node point to the database via a communications network.

In contrast, FIG. 22 illustrates a second mode of data flow. In this second mode, data is communicated externally from a building, such as the hospital 930 or warehouse 920. The data is communicated from the tray communication device 962 to a database for storing location information. The tray communication device 962 wirelessly contacts the communications network 950, such as a cellular telephone network, to transmit location information to the database.

Figure 23:
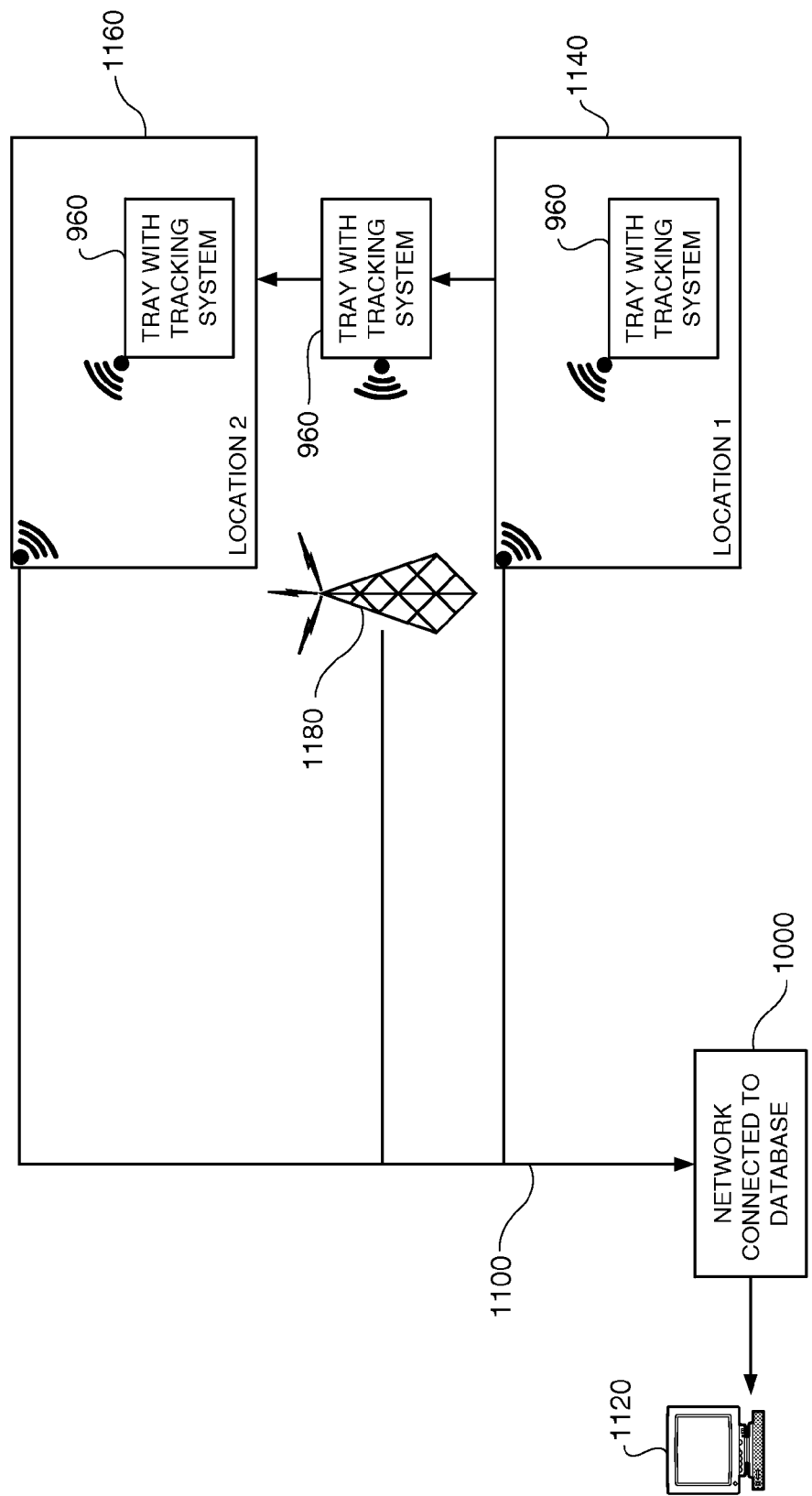
FIG. 23 is a schematic illustrating data flow of location information of an instrument tray.

FIG. 23 illustrates data flow of location information for the surgical asset 960. FIG. 23 illustrates a database 1000, a network 1100, a user interface 1120, a first location 1140, a second location 1160, and a node 1180. The surgical asset 960 begins at the first location 1140. In one embodiment, a reader interrogates the surgical asset 960 and sends data to the database 1000 via the network 1100. In alternative embodiments, the surgical asset 960 periodically broadcasts location information or is periodically polled for location information. The data is stored in the database as the current location. Thereafter, the surgical asset 960 is in transit and sends data to the node 1180. The node 1180 retransmits the data to the database 1000. The data from the node 1180 is then stored as the current location. The surgical asset 960 arrives at the second location 1160. After arrival, the surgical asset 960 sends updated data to the database 1000 via the network 1100. As before, the surgical asset may broadcast information, be interrogated for information, or polled for location information. The location data is updated in the database as the current location. The user interface 1120 may be used at any time to review the database and look-up the current location information of the tray 960.

Figure 24:
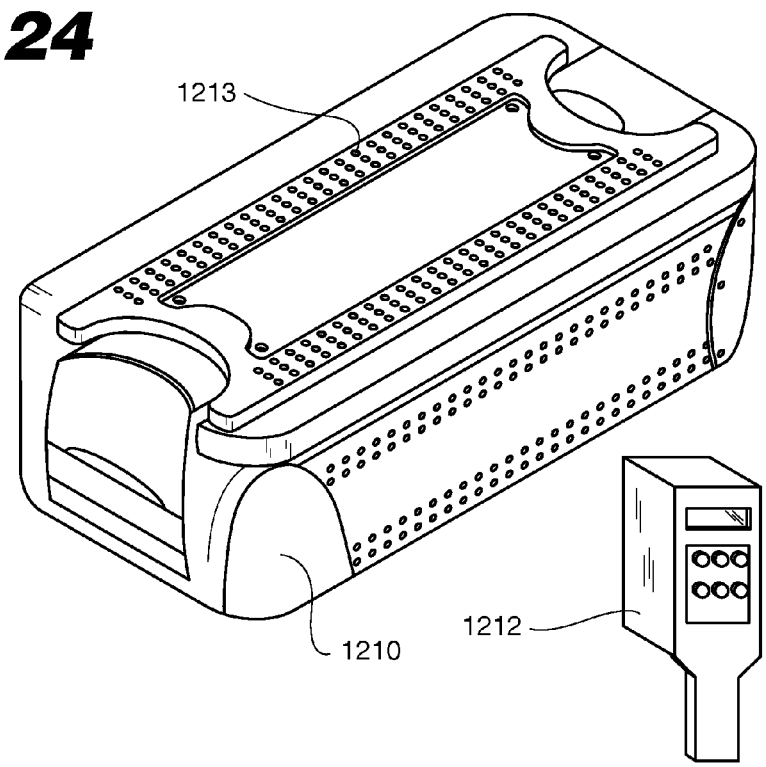
FIG. 24 is a perspective view illustrating a sterilization case and an RFID tag reader.
Figure 27:
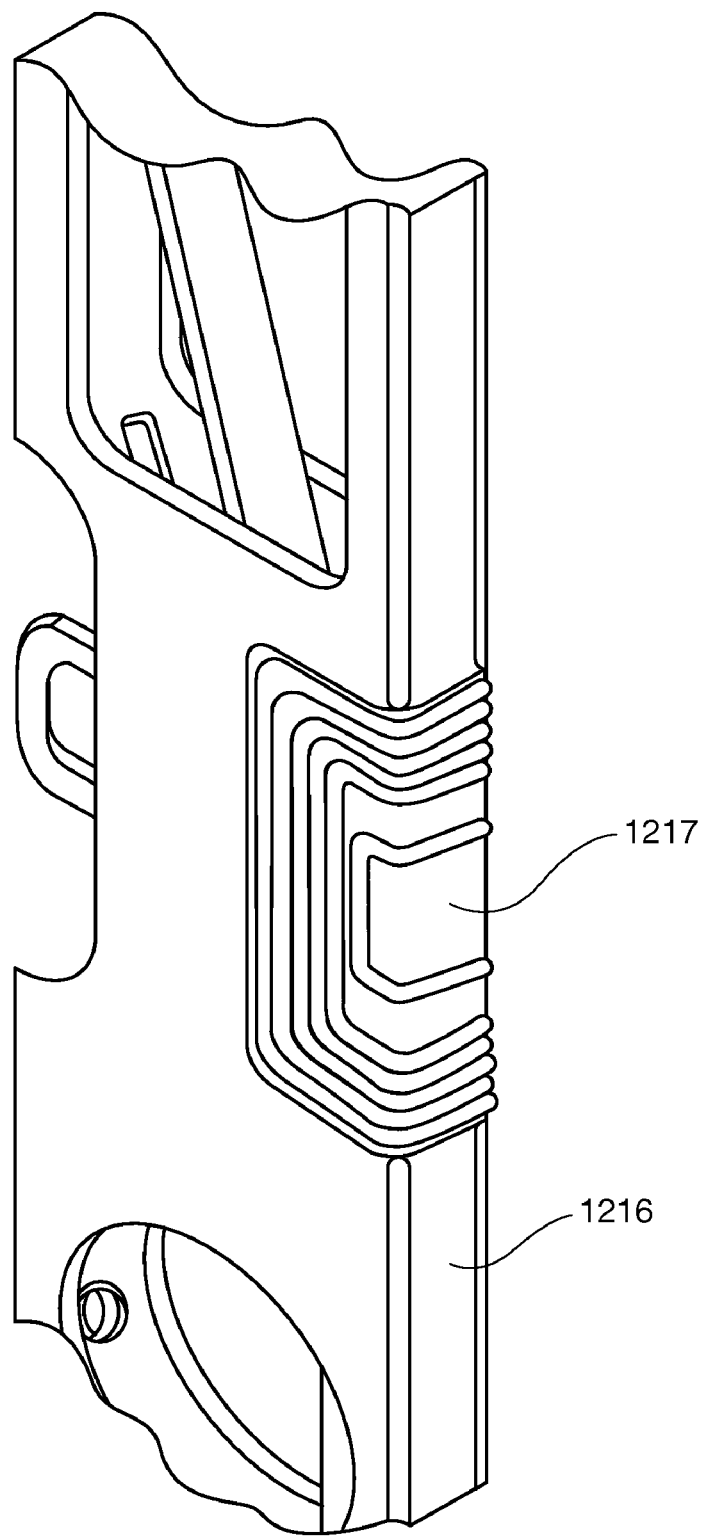
FIG. 27 is a perspective view illustrating a medical instrument with an RFID tag located on the outside surface of the instrument.
Figure 28:
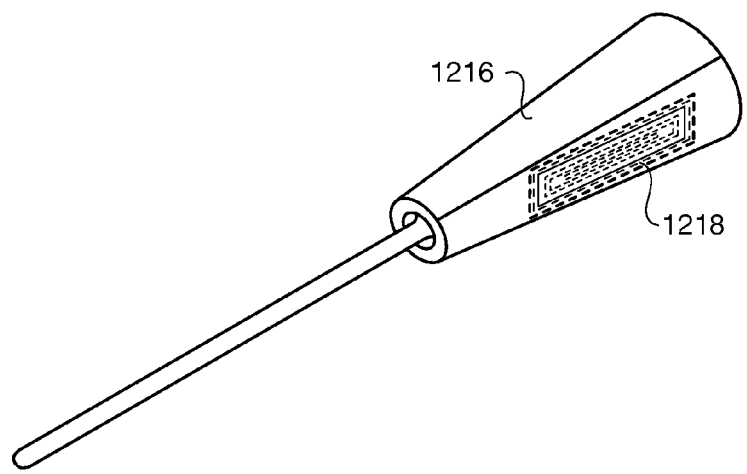
FIG. 28 is a perspective view illustrating a medical instrument with an RFID tag embedded in the instrument.

Referring initially to FIG. 24, illustrated is a system for identifying surgical assets. The system may form a portion of the system for tracking surgical assets. Included in the depicted embodiment is a sterilization case 1210 and an RFID reader 1212 configured to communicate with RFID tags. The sterilization case 1210 may also be known as an instrument tray case. The sterilization case 1210 may contain various medical instruments, such as medical instruments 1216 shown in FIGS. 27 and 28, medical implants, and RFID tags, such as RFID tags 1217 and 1218 shown in FIGS. 27 and 28. It should be understood that other types of medical instruments and RFID tag configurations may be used with the several embodiments of the present invention. RFID tags 1217 and 1218 are attached to, associated with, or embedded in the medical instruments 1216. FIG. 27 shows one embodiment of the invention where an RFID tag 1217 is associated or attached to medical instrument 1216. FIG. 28 shows another embodiment of the invention where an RFID tag 1218 is embedded in the medical instrument 1216.

In some embodiments, RFID tags 1217 and 1218 are attached to the medical instruments 1216 by an adhesive substance such as glue, paste, gum, epoxy resin, tape, bonding agent, or any other type of adhesive that will attach the RFID tags 1217 and 1218 to the medical instrument 1216. In other embodiments, RFID tags 1217 and 1218 are attached to the medical instruments 1216 by a mechanical device such as a clip, fastener, clasp, pin, screw, or any other device that will mechanically associate an RFID tag to a medical instrument. In other embodiments, RFID tags 1217 and 1218 may be attached to the medical instruments 1216 by molding or otherwise, including during manufacture of medical instruments 6 or otherwise.

Referring again to FIG. 24, in some embodiments, the sterilization case 1210 may be made from steel, aluminum, titanium, plastic or any other appropriate material that will provide containment for sterilization purposes. In some embodiments, the sterilization case 1210 includes at least one side with at least one opening 1213, such as holes, slits, or any other type and size of opening or openings in at least one side of the sterilization case shaped and sized to allow RFID tags 1217 and 1218 in the sterilization case 1210 to respond to a reader 1212. In other embodiments, at least one side of the sterilization case 1210 may be made from materials such as plastic, paper products, wood, cloth, vinyl, leather, or any other appropriate material that allows radio frequency signals to enter and leave the case. As examples, the sterilization case lid, a portion of the side, or the end portions may be made of plastic.

Figure 25:
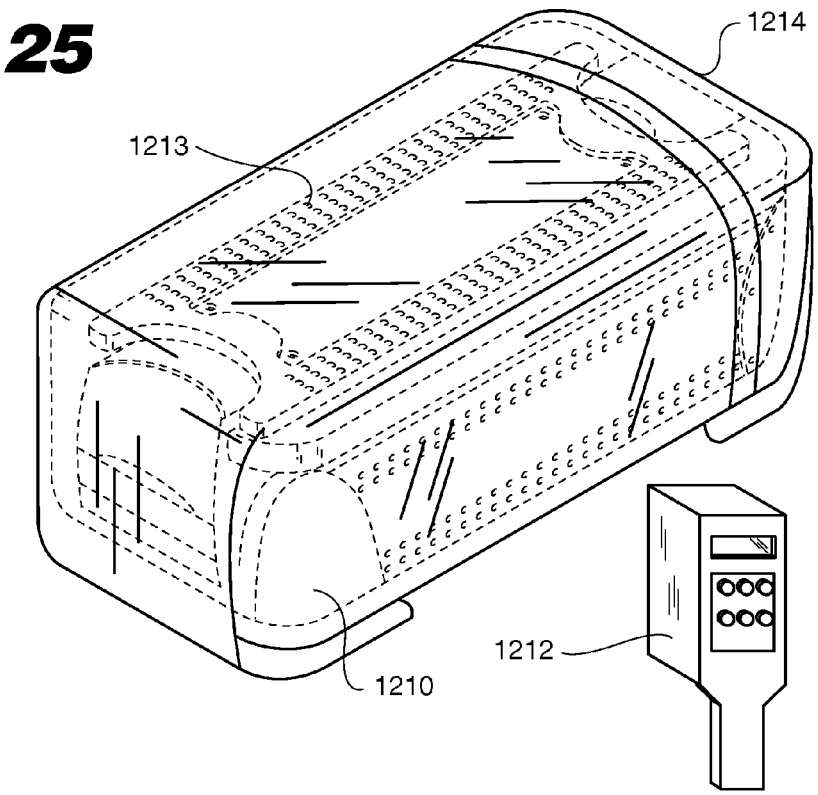
FIG. 25 is perspective view illustrating a sealed wrap over a sterilization case and RFID tag reader.

Referring now to FIG. 25, illustrated is another alternative embodiment of the system for identifying surgical assets. Included in this embodiment is a reader 1212 and a sealed wrap 1214 surrounding a sterilization case 1210 with at least one opening 1213. The sealed wrap 1214 may be composed of assorted materials such as various combinations of plastic, paper, polyethylene film, polyester film, foil, laminate material, polypropylene, polyolefin, polymusum, or any other material that may be used to wrap the sterilization case for sterilization purposes.

RFID tags 1217 and 1218 of certain embodiments of the invention, associated with medical instruments 1216 and located inside the sterilization case 1210, have the capability of transmitting or responding with encoded data or a signature when they are interrogated by a reader 1212. In some embodiments, the RFID tags are passive, in that they do not contain an independent energy source but must depend on the radio frequency signal from the reader to provide its response or signature. An alternative embodiment includes active RFID tags that contain an independent energy source, such as a battery or other energy sources, so that the RFID tag can actively transmit a signal or information.

The reader 1212 is shown as a handheld device capable of transmitting a signal via radio frequency to the RFID tags 1217 and 1218 and receiving encoded data or RFID tag signatures via radio frequency from the RFID tags 1217 and 1218. The reader 1212 also has the capability of outputting the received data onto a viewable interface or to a computer via electrical or wireless connection. It should be understood by those with skill in the art that the reader 1212 may take any stationary or movable form with the function of reading RFID tags. For example, in an alternative embodiment the reader 1212 is a mat and the sterilization case 1210 containing the medical instruments 1216, may be placed on the mat. The reader 1212 then reads the RFID tags attached to the medical devices.

When the sterilization case 1210 is made from steel, aluminum, titanium, or any type of metal, radio frequency communication between an RFID tag 1217 and 1218 and a reader 1216 may be greatly attenuated and the presence of metal may prevent all communication. The sterilization case, however, may be modified to allow radio frequency communication between the RFID tags 1217 and 1218 and reader 1212. Modifications to the sterilization case may include openings 12133 such as holes, slits, or any other type and size of opening in at least one side of the sterilization case. In other embodiments the sterilization case 1210 may be made from a material, such as plastic, paper products, wood, cloth, vinyl, metal or leather, that allows radio frequency signals to enter and leave the case. In still other embodiments, a master RFID tag or reader may be attached to the outside of the sterilization case to collect information from inside the case and communicate the information to an external reader.

Figure 26:
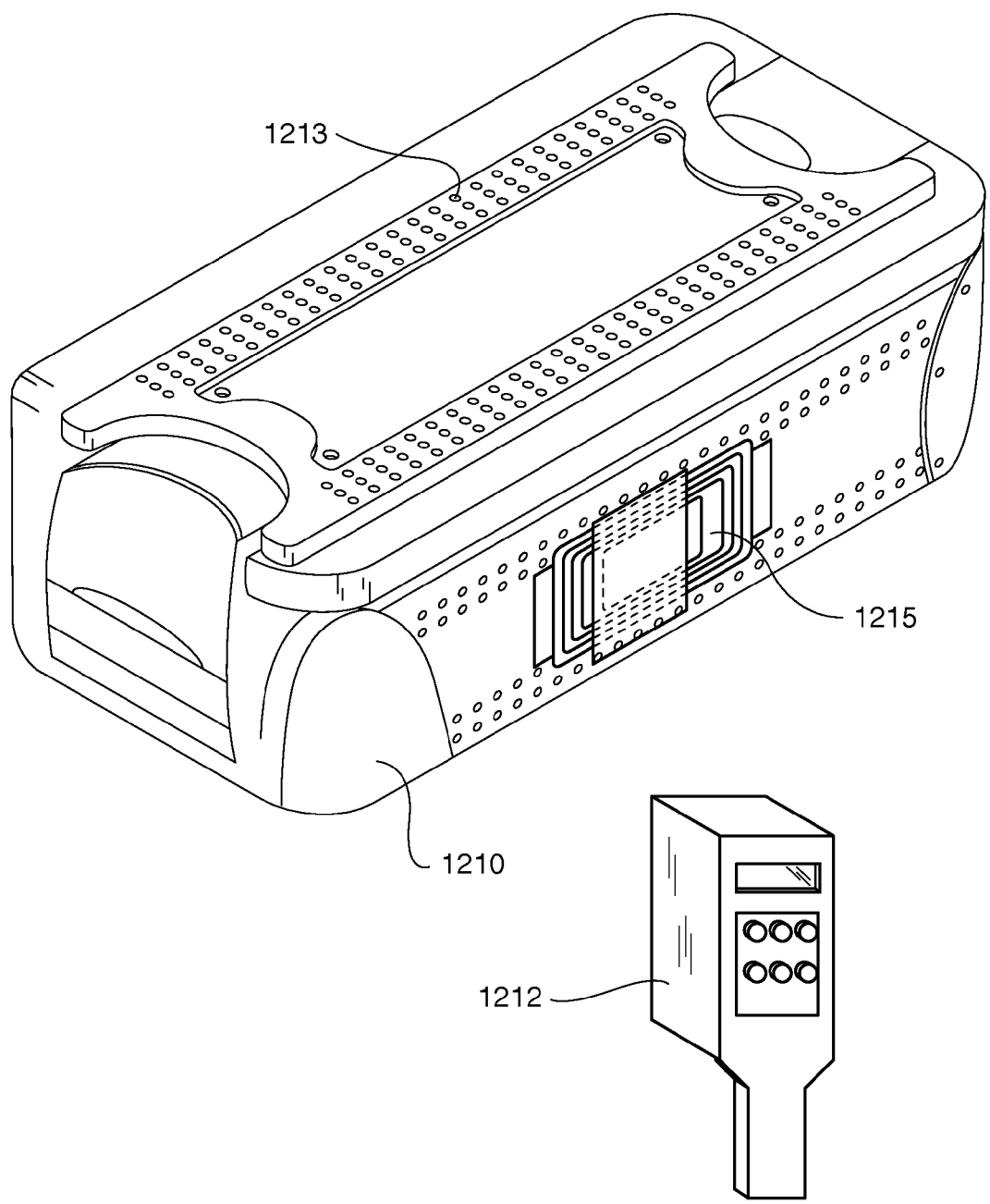
FIG. 26 is a perspective view illustrating a second medical instrument packet and RFID tag reader.

Referring now to FIG. 26, illustrated is another alternative embodiment of the present invention. Included in this embodiment is a sterilization case 1210 and RFID tag reader 1212. The sterilization case 1210 contains RFID tags attached to medical instruments and/or medical implants. The sterilization case 1210 also contains a case RFID tag 1215 attached on the outside of at least one of the sterilization case's surfaces. In some embodiments, the case RFID tag 1215 has the capability of receiving a signal from the reader 1212 and then transmitting or responding with encoded data or identifying information to the reader 1212. In other embodiments, the case RFID tag 1215 may communicate through radio frequency signals to the RFID tags associated with the medical instruments located inside the sterilization case 1210. The case RFID tag 1215 then communicates the information received from the RFID tags inside the case to the reader 1212.

In certain embodiments, the type of data transmitted by the RFID tags 1217 and 1218 and case RFID tag 1215 to the reader 1212 may include the identification of the medical instruments 1216 to which the RFID tags 1217 and 1218 are attached, the contents of the entire sterilization case 1210, the surgical technique associated with a particular medical instrument 1216 or group of medical instruments contained within the sterilization case 1210, surgical implants with which the instrument 1216 is to be used, the manufacturing history of a particular medical instrument 1216, how many times the instrument 1216 has been sterilized, or any other relevant data associated with the instruments, group of instruments, or case. Alternatively, the RFID tags 1217 and 1218 may respond with a signal or signature that keys or correlates to such information in a database in the computer system or on a network such as the Internet or a local network. One may see that a number of different types of data may be conveyed with or keyed to information conveyed using RFID tags 1217 and 1218 and case RFID tag 1215. In the embodiments depicted in FIGS. 27 and 28, the RFID tags 1217 and 1218 transmit or respond with data that corresponds to the identification of a particular medical instrument 1216 and the case RFID tag 1215 transmits data corresponding to the identification and contents of a particular sterilization case 1210.

Referring now to FIG. 27, illustrated is the RFID tag 1217 attached to a medical instrument 1216. The RFID tag 1217 is attached on the outside surface of the medical instrument 1216. Various methods may be utilized to attach the RFID tag 1217 on the outside surface of the medical instrument 1216. For example, the RFID tag 1217 may be attached on the outside surface of the medical instrument 1216 through any adhesive or mechanical device. In some embodiments, the adhesive substance may be glue, paste, gum, epoxy resin, tape, bonding agent, or any other type of adhesive that will attach an RFID tag 1217 to a medical instrument 1216. In other embodiments, RFID tags 1217 are associated to the medical instrument 1216 by a mechanical device. The mechanical device may be a clip, fastener, clasp, pin, screw, or any other device that will mechanically associate an RFID tag to a medical instrument.

Referring now to FIG. 28, illustrated is one embodiment of a RFID tag 1218 attached to a medical instrument 1216. In this particular embodiment, the RFID tag 1218 is embedded inside the medical instrument 1216 and is not viewable from the surface of the medical instrument 1216. Various procedures may be utilized to embed the RFID tag 1218 into medical instrument 1216 such as removing a portion of the medical instrument and replacing the portion with an RFID tag 1218. Other procedures apparent to those of ordinary skill in the art may be utilized to embed the RFID tag 1218.

Referring again to FIG. 25, to inventory and manage medical instruments while they are in a sealed wrap 1214, the user begins by waving the reader 1212 in proximity to the sealed and wrapped sterilization case 1210. This distance between the reader 1212 and sterilization case 1210 may be as little as 5 millimeters to as much as several feet or more. In an alternative embodiment, the reader 1212 may be stationary while the user locates the sealed and wrapped sterilization case 1210 in proximity to a stationary reader 1212. The reader 1212 transmits a radio frequency signal interrogating the RFID tags associated with medical instruments inside the sterilization case 1210. The RFID tags respond to the interrogation by transmitting a radio frequency signal or responding with a signature containing encoded or indicative data. The reader 1212 receives these signals and sends them to a computer and/or correlates them to a database contained within the reader 1212 or elsewhere such as on a network.

Figure 29:
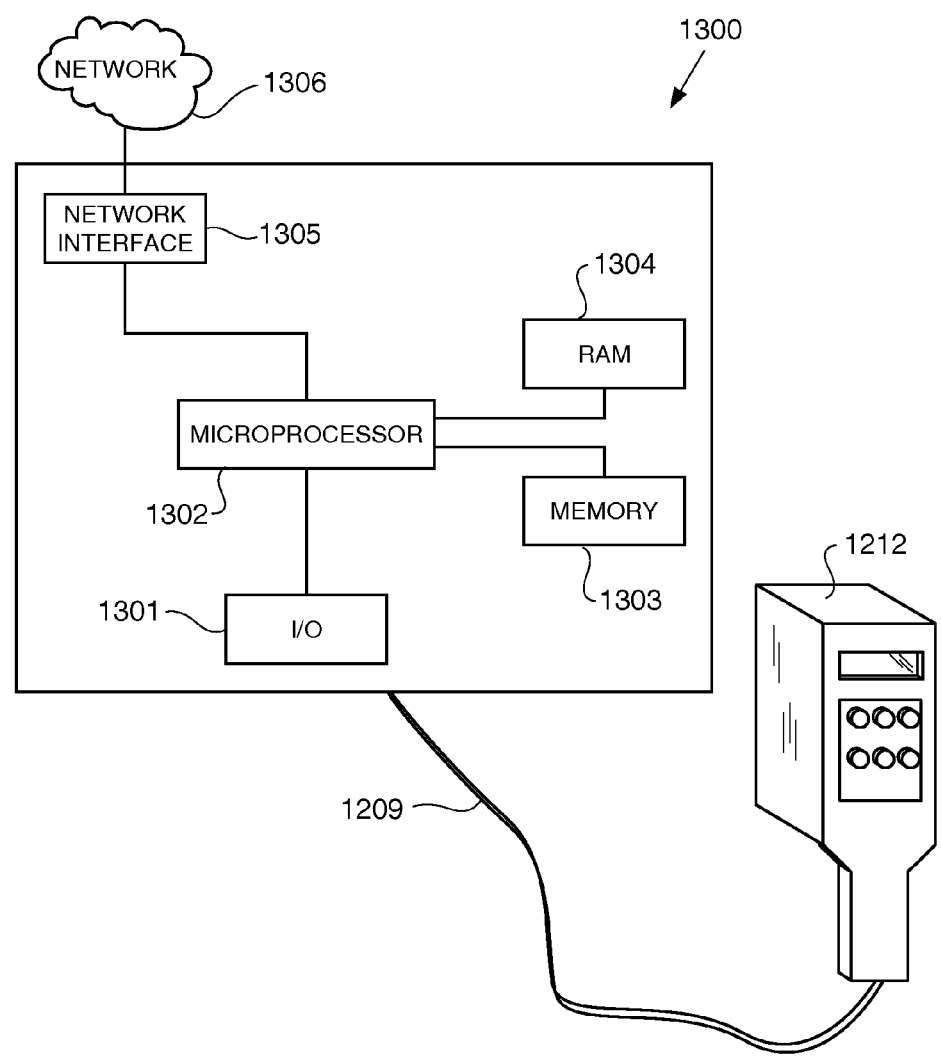
FIG. 29 is a schematic illustrating a reader electrically connected to a computer system.

Referring now to FIG. 29, the reader 1212 sends the encoded or indicative data to a computer system 1300 via electrical signals along a cable 1209. In an alternate embodiment, the reader 1212 communicates the encoded or indicative data received from the RFID tags via wireless connection to a computer system 1300. In some embodiments, the computer system 1300 includes an input/output 1301, microprocessor 1302, memory device 1303, random access memory 1304, and network interface 1305. The input/output 1301 takes in the information from the reader and sends the information to the microprocessor 1302. The microprocessor 1302 compares the information with a database in the memory 1303 and/or random access memory 1304. The microprocessor 1302 then displays the results onto an interface, such as a monitor, that may be viewed by a user, sends the information in the memory 1303 for storage, and/or sends the results to a network interface 1305 that is in communication with a network 1306. The network 1306 may include a plurality of computer systems, an Internet, a local area network, or any type of network systems capable of processing or transferring data.

In an alternative embodiment, the reader 1212 includes a database and viewable interface. The reader 1212 compares the encoded data with the database and the results are viewable on the interface.

Figure 30:
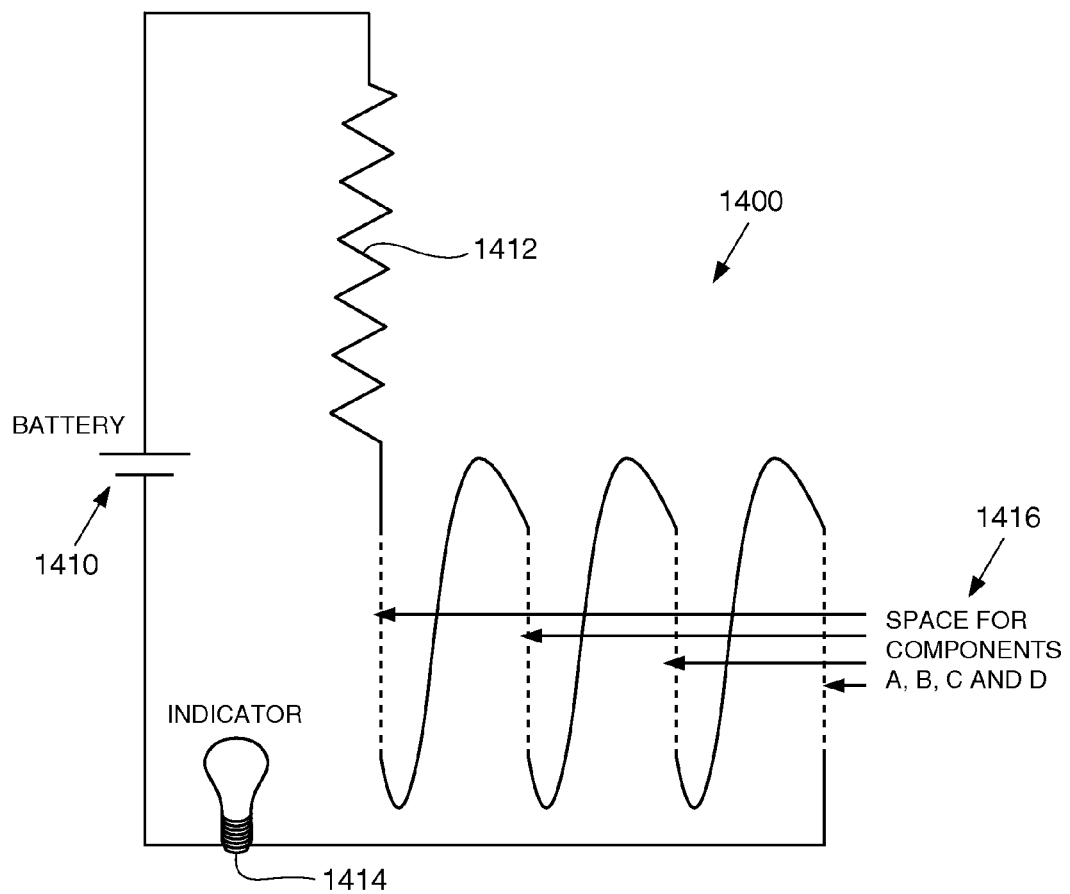
FIG. 30 is a schematic illustrating a smart electronic instrument tray.

FIG. 30 illustrates a smart electronic sterilization case or instrument tray 1400. The sterilization case 1400 includes a battery 1410, a resistor 1412 and an indicator bulb 1414. In the depicted embodiment, the components are all in series. The tray 1400 includes spaces 1416 to receive instruments or implants (not shown). The circuit is completed by the current being able to flow through the outer packaging of the tray component (i.e., the instrument or implant) or the component itself. The bulb 1414 lights when all instrument components are present.

Figure 31:
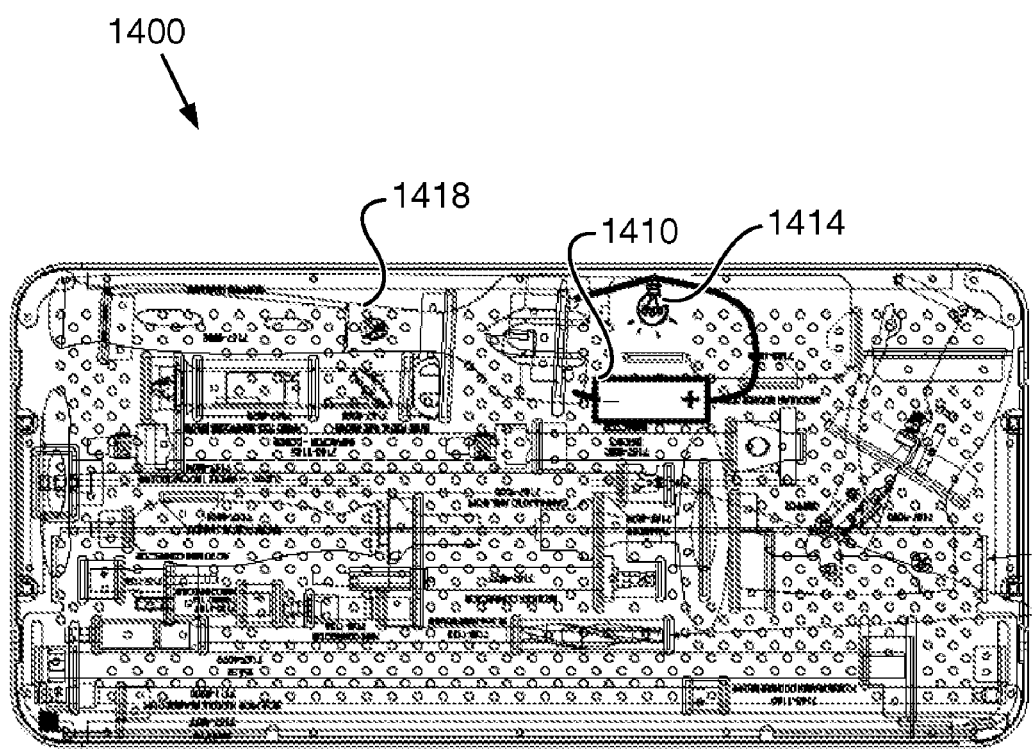
FIG. 31 is a top view illustrating the smart electronic instrument tray.

A schematic representation of the sterilization case 1400 is shown in FIG. 31. In this figure, one individual instrument 1418 is electrically connected to the case. In the depicted embodiment, the individual instrument 1418 is a slot hammer but those of ordinary skill in the art would understand that other instruments or implants may be used. The removal of this particular item from the tray 1400 results in a break in the circuit alerting the clinician via the indicator bulb 1414, a hand held PDA, computer, or a specialized device, that the instrument 1418 has been removed.

Figure 32:
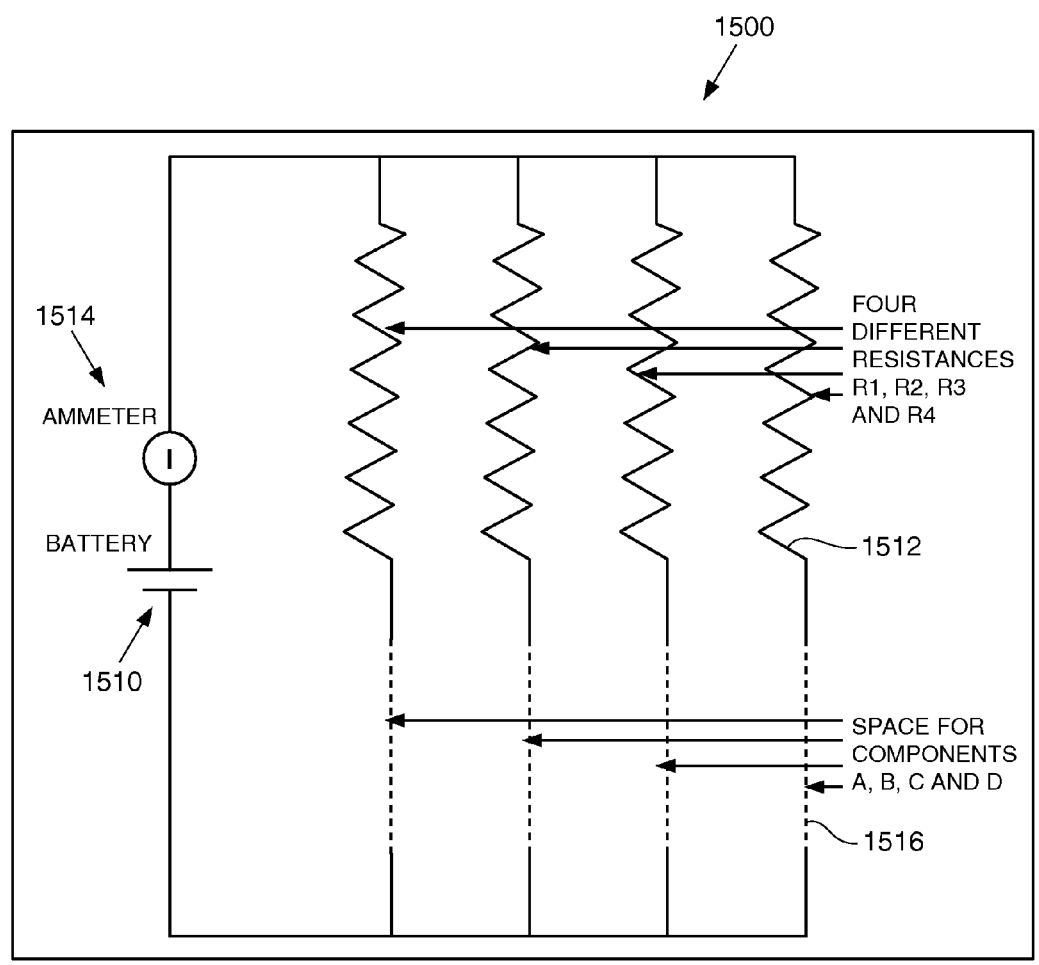
FIG. 32 is a schematic illustrating an alternative embodiment of a smart electronic instrument tray.

FIG. 32 illustrates an alternative embodiment of the sterilization case, indicated by numeral reference 1500. The tray 1500 includes a battery 1510, one or more resistors 1512 and an ammeter 1514. In this particular embodiment, the specific component that is missing can be identified. The components are now in parallel, and each component, such as an instrument or an implant, is in series with a different resistor 1512. The indicator bulb of the previous embodiment has been replaced by the ammeter 1514 as it is necessary to know the current flowing within the circuit. The sterilization case 1500 includes spaces 1516 to receive instruments or implants (not shown). In this configuration, the identity of each of the instrument components can be obtained from a unique resistance measurement. In the depicted embodiment, there are four spaces 1516 but those having ordinary skill in the art would understand that a greater or lesser number of spaces may be used.

Figure 33:
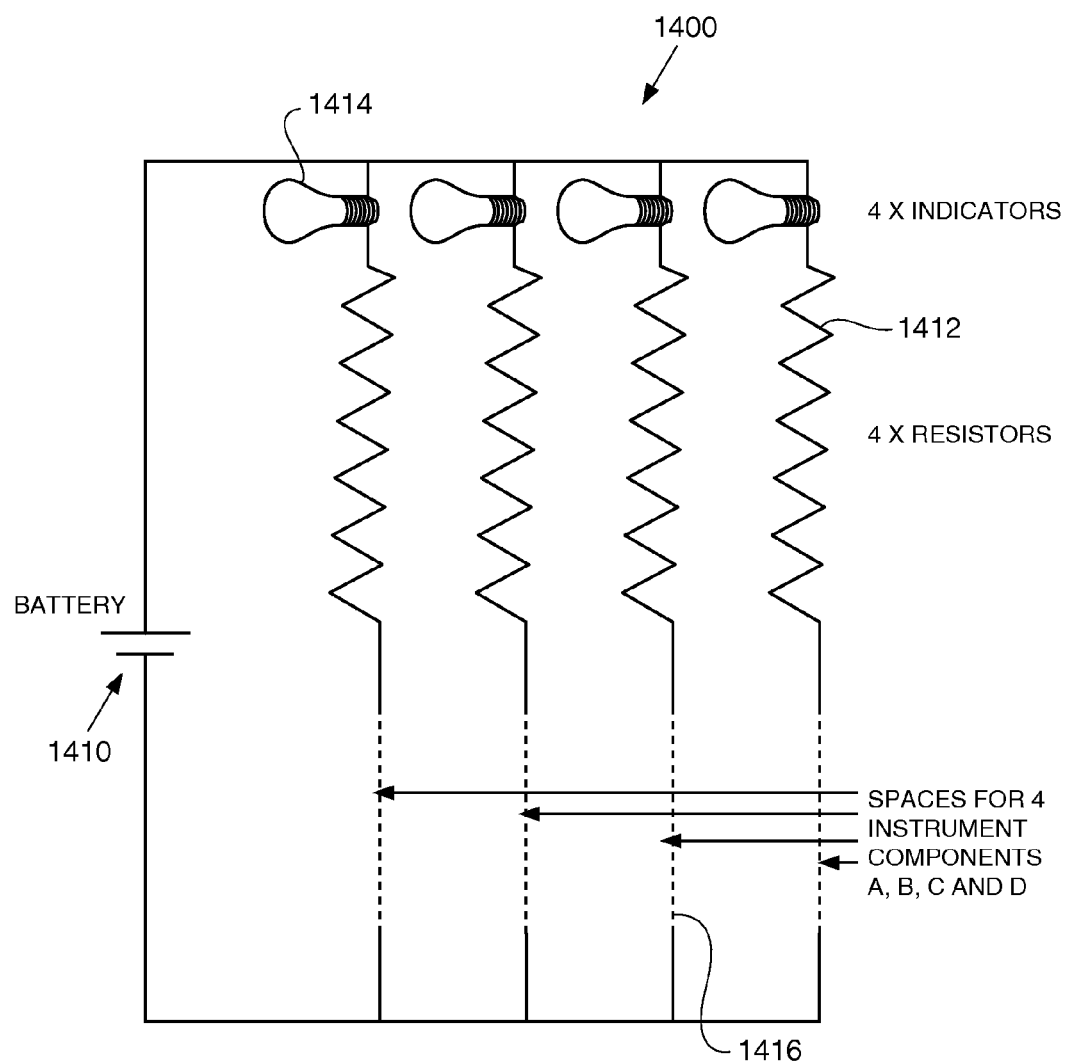
FIG. 33 is a schematic illustrating the smart electronic instrument tray with four medical devices.

FIG. 33 illustrates how each instrument can be identified by its own unique resistor and indicator bulb which are connected to their respective housing and arranged in parallel in an electrical circuit. The parallel arrangement informs the user if the particular item is either present or absent in the tray.

The identification of which component is in the sterilization case is dependent upon knowing the equation for the total resistance of several resistors in parallel. For two resistors, R1 and R2 in parallel, the total resistance is:

$$R = R1 \times R2 / (R1 + R2) \qquad \text{Equation 1}$$

For three resistors, R1, R2 and R3 in parallel, the total resistance is (omitting the multiplication signs for clarity):

$$R = R1 \times R2 \times R3 / (R1\,R2 + R1\,R3 + R2\,R3) \qquad \text{Equation 2}$$

The general equation for n resistors in parallel is:

$$1/R = 1/R1 + 1/R2 + 1/R3 \ldots + 1/Rn-1 + 1/Rn \qquad \text{Equation 3}$$

By a careful choice of R1, R2, etc., the knowledge of R will uniquely identify which components are in the tray. Let the resistors R1 to R4 in FIG. 32 have the values 1, 2, 4 and 8 Ohms respectively. A full sterilization case will have a resistance of 8/15 Ohms. The four possible resistances if just one component is missing are 8/7, 8/11, 8/13 and 4/7 Ohms. Other resistances are possible if two or three components are missing. The resistance is infinite if all components are missing.

The wires in the electrical circuit go through the holders for each of the components, whether the holders are foam or something more rigid. If the battery and indicator were also in the foam or equivalent material, the sterilization case itself would not have to be altered in any way. However, it may be beneficial to fix the battery and/or indicator to the sterilization case.

Figure 34:
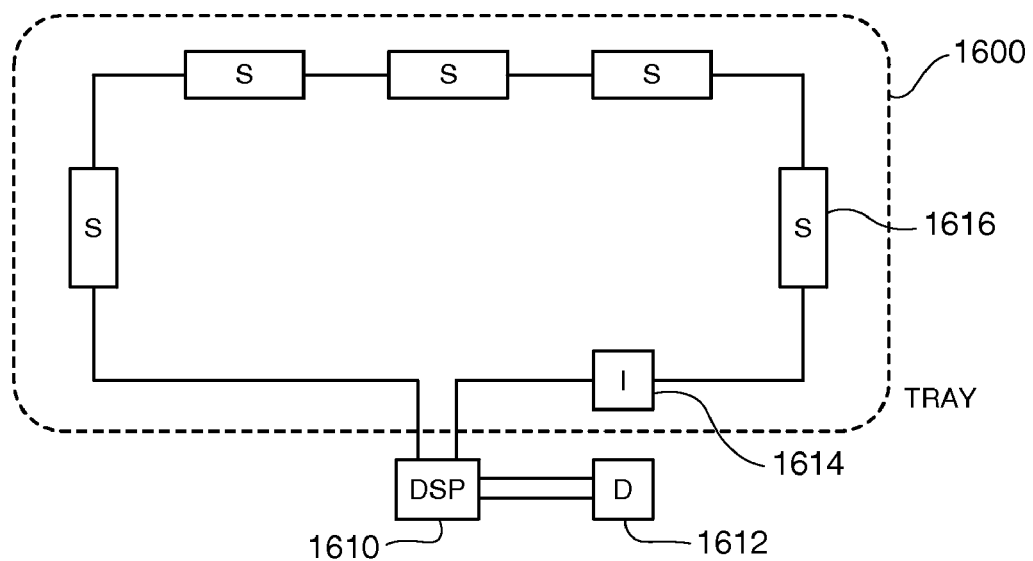
FIG. 34 is a schematic circuit diagram highlighting instruments arranged in series.

More complex variations of the technology for identifying medical instruments in a sealed sterilization case are described below in FIGS. 34-38. These particular examples incorporate digital signal processing (DSP) and capacitors to cope with instrument trays containing multiple instruments. FIG. 34 is a schematic circuit diagram highlighting instruments arranged in series. The sterilization case 1600 includes a digital signal processor 1610, a display 1612, an indicator 1614, and one or more sockets 1616. The sockets 1616 may receive implants or instruments. In some embodiments, the display 1612 or the indicator 1614 may be omitted.

Figure 35:
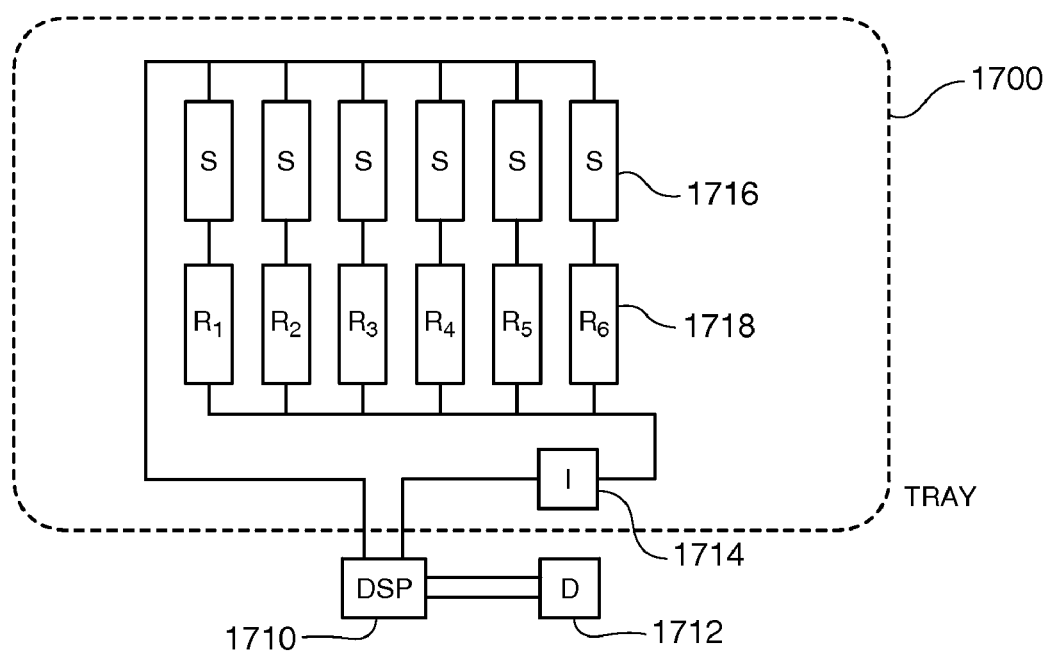
FIG. 35 is a schematic circuit diagram highlighting instruments arranged in parallel.

FIG. 35 is a schematic circuit diagram highlighting instruments arranged in parallel. The instrument tray 1700 includes a digital signal processor 1710, a display 1712, an indicator 1714, one or more sockets 1716, and a corresponding number of resistors 1718. The sockets 1716 may receive implants or instruments.

Figure 36:
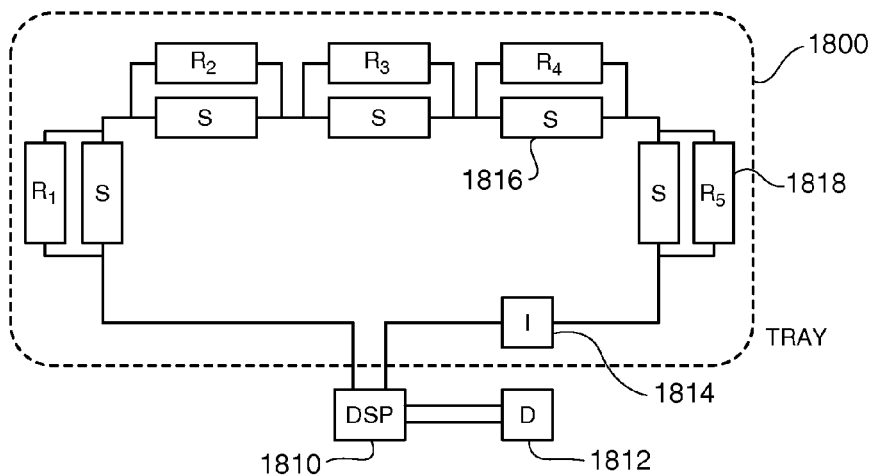
FIG. 36 is a schematic circuit diagram highlighting instruments arranged in series with parallel resistors.

FIG. 36 is a schematic circuit diagram highlighting instruments arranged in series with parallel resistors. The instrument tray 1800 includes a digital signal processor 1810, a display 1812, an indicator 1814, one or more sockets 1816, and a corresponding number of resistors 1818. The sockets 1816 may receive implants or instruments.

Figure 37:
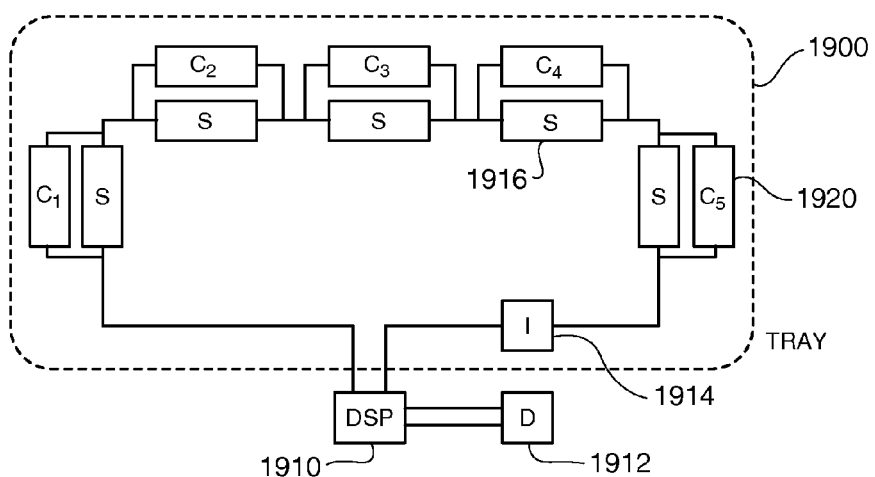
FIG. 37 is a schematic circuit diagram highlighting instruments arranged in series with parallel capacitors.

FIG. 37 is a schematic circuit diagram highlighting instruments arranged in series with parallel capacitors. The sterilization case 1900 includes a digital signal processor 1910, a display 1912, an indicator 1914, one or more sockets 1916, and a corresponding number of capacitors 1920. The sockets 1916 may receive implants or instruments.

Figure 38:
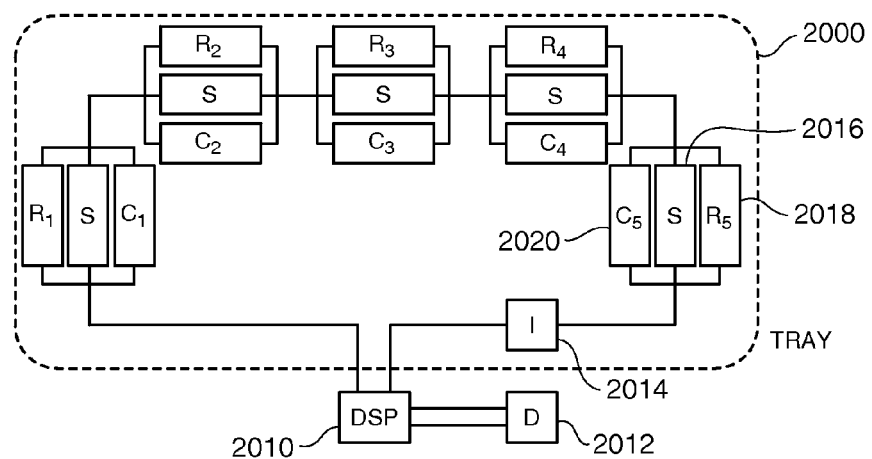
FIG. 38 is a schematic circuit diagram highlighting instruments arranged in series with parallel capacitors and resistors.

FIG. 38 is a schematic circuit diagram highlighting instruments arranged in series with parallel capacitors and resistors. The sterilization case 2000 includes a digital signal processor 2010, a display 2012, an indicator 2014, one or more sockets 2016, a corresponding number of resistors 2018, and a corresponding number of capacitors 2020. The sockets 2016 may receive implants or instruments.

Alternatively, the circuit may be a complex circuit that has a "yes/no" indicator showing whether the case is correctly filled. If "no," then a handheld device containing a DSP is plugged into the case (via a socket on the outside) to carry out a more involved analysis to determine why the case is not correctly filled. It is a bit like the warning light in a car coming on, so the owner drives to the garage where a computer does a series of diagnostic tests. In principle, one handheld device could contain diagnostic software for all instrument cases, and also contact the medical device manufacturer with the relevant information.

The electronic sterilization case may be powered using an internal sterilizable battery or an external battery which could be attached to the outside of the case when the contents of the sterilization case need to be read. The main constraint to powering the system using this approach is that the user would have to read through the wrapping after the set had been sterilized. Alternatively, it is possible to inductively power the circuit in the same way that passive RFID tags are powered. In this situation, no battery is required. It is also possible that the output from the indicator is saved on an active RFID tag on the outside of the tray. Thus, it is possible for the circuit to tell the tag what is in the tray, and for the tag to tell the RFID reader, and therefore the outside world, what is in the tray. This gets around the problem associated with some RFID systems of not being about to detect through or very close to metals.

Figure 39:
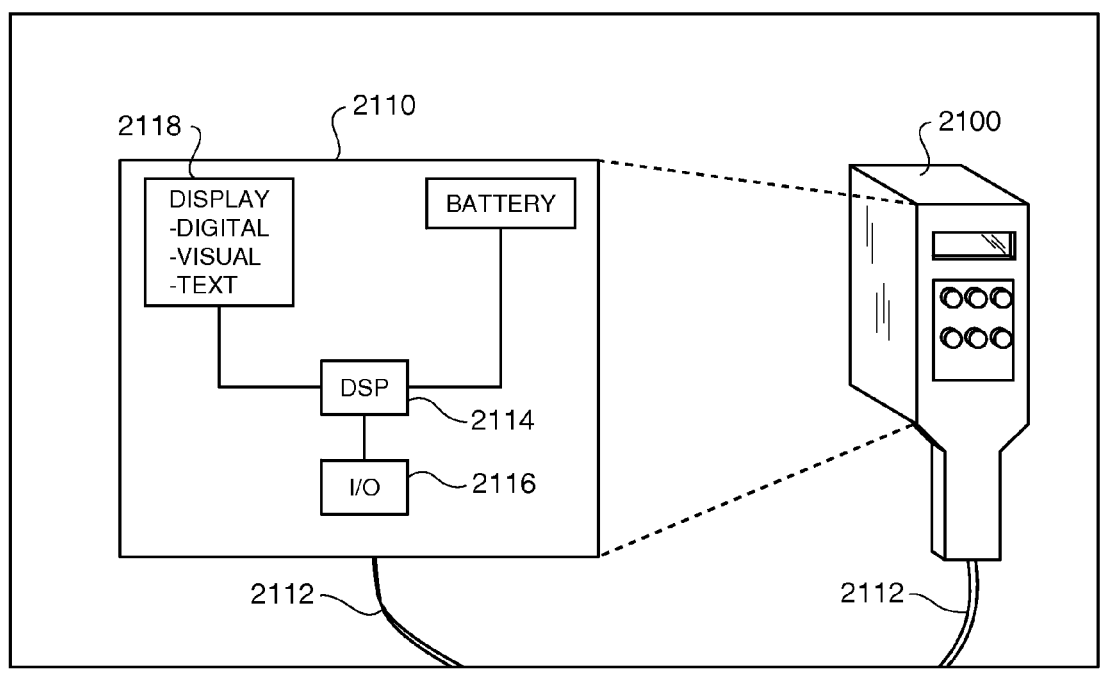
FIG. 39 is a schematic illustrating a reader electrically coupled to an instrument tray prior to a surgical procedure using a hard wire connection.

The electronic sterilization case can be connected to a reader 2100 via a plug-in or a wireless connection. In the embodiment depicted in FIG. 39, the reader 2100 is electrically coupled to an instrument tray 2110 prior to the surgical procedure using a hard wire connection 2112. The instrument tray 2110 is configured to allow electrical energy to enter and leave the sterilization case via the electrical cable 2112 which is located through either a hole, slit or any other opening in at least one side of the instrument tray case specifically designed in size and/or shape to allow electrical signals to pass through. Ideally, the tray and inserts used to house the instruments are made from conducting and insulative materials respectively for effective transmission of the electrical signal through the circuit.

The reader 2100 powers the sterilization case using an on-board battery and is electrically linked via the input/output (I/O) connection 2116. A digital signal processor (DSP) 2114 located in the reader processes the electrical signal received from the source (sterilization case) into a format that can be easily interpreted by the end user. The information is then displayed on a screen 2118 in three formats (a) digital, (b) visual or (c) text, which is then selected by the end user. The reader interrogates the tray to determine whether there are either missing instruments or incorrectly placed instruments. This information is displayed on the screen of a personal device assistant (PDA) which can be used by a member of the hospital staff. The current data set generated is compared to a set of signals stored in a database, which are either contained in the reader or a remote computer system. A software program informs the user if the contents of the case are present, enabling them to proceed with the autoclaving of the sterilization case. The user can verify this information by repeating the task. In the event where the displayed results indicate that some instruments are missing, the software could alert the hospital staff to search for other cases which could be quickly selected and read to determine if they contain all the necessary instruments for a particular surgical procedure. In this situation, an appropriate sterilization case can be selected and its sealed wrap broken for a particular procedure.

Figure 40:
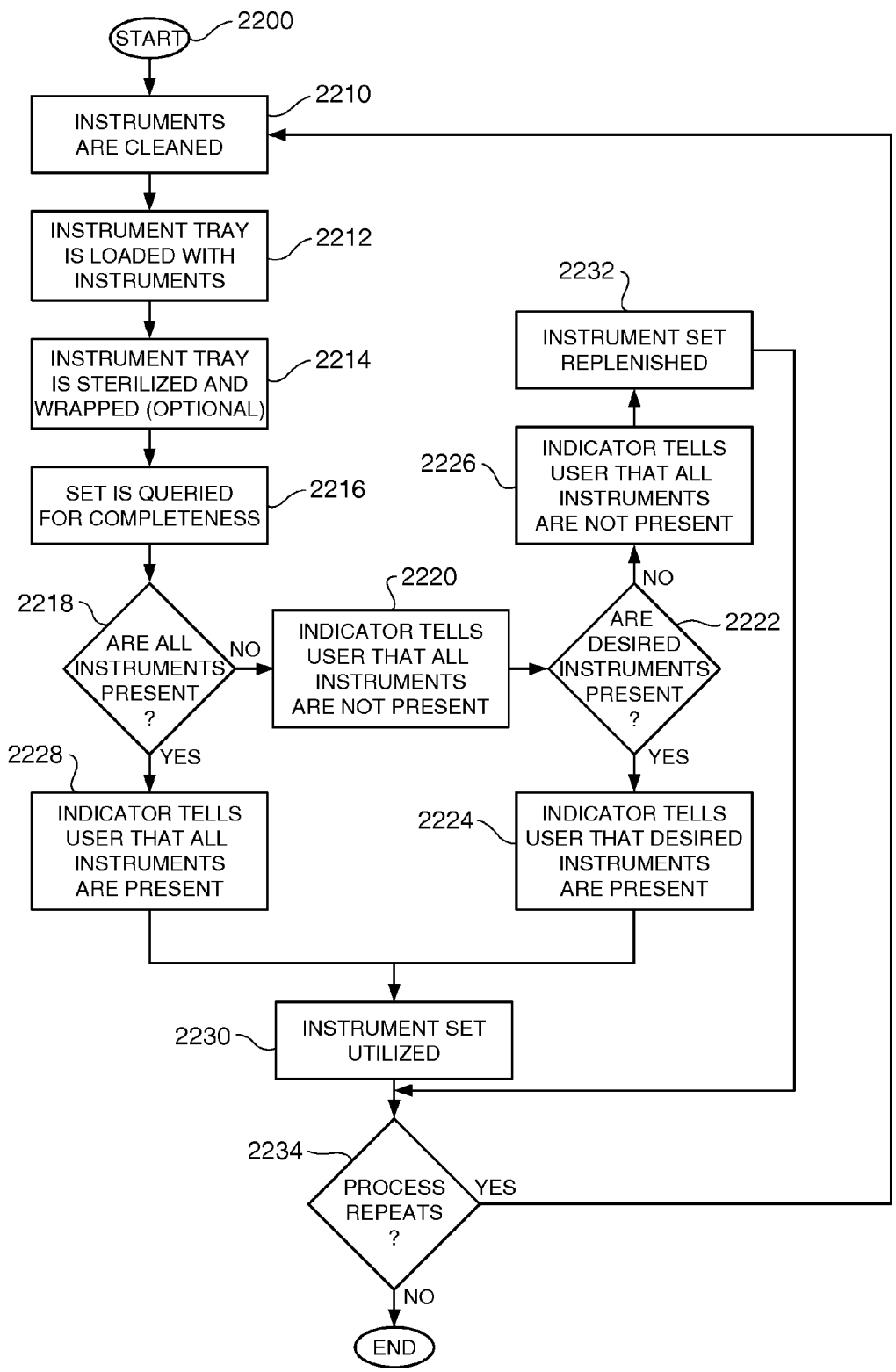
FIG. 40 is a highlighting the decision making process algorithm.

FIG. 40 illustrates a flow chart highlighting the decision making process algorithm. The process begins at step 2200. In step 2210, instruments are cleaned. A sterilization case is loaded with instruments and/or implants in step 2212. In an optional step 2214, the instrument tray is sterilized and wrapped. The instrument tray is queried for completeness in step 2216. In step 2218, a decision is made whether all of the medical devices, such as instruments or implants, are present. If not, an indicator indicates to the user that not all of the medical devices are present in step 2220. In step 2222, a decision is made whether the desired instruments are present. If so, the indicator indicates to the user in step 2224 that the desired instruments are present. If not, the indicator indicates to the user that the desired instruments are not present in step 2226. Referring once again to step 2218, if all of the instruments are present, then the indicator indicates to the user in step 2228 that all of the instruments are present. After step 2228 or step 2224, the process proceeds to step 2230 wherein the instrument set is utilized. In some embodiments, the instrument set is completed in step 2232 if it is indicated that the desired instruments are not present in step 2226. After step 2230, a decision is made whether to reuse or retire the instrument set in step 2234. If the instrument set is to be reused, the process returns to step 2210. Otherwise, the process ends at step 2240.

The user may utilize the results displayed on the interface to determine whether all necessary instruments for a particular surgical procedure are contained within the packet, if some necessary instruments are missing to locate them in another instrument packet, or to locate a packet that contains all necessary instruments.

Figure 41:
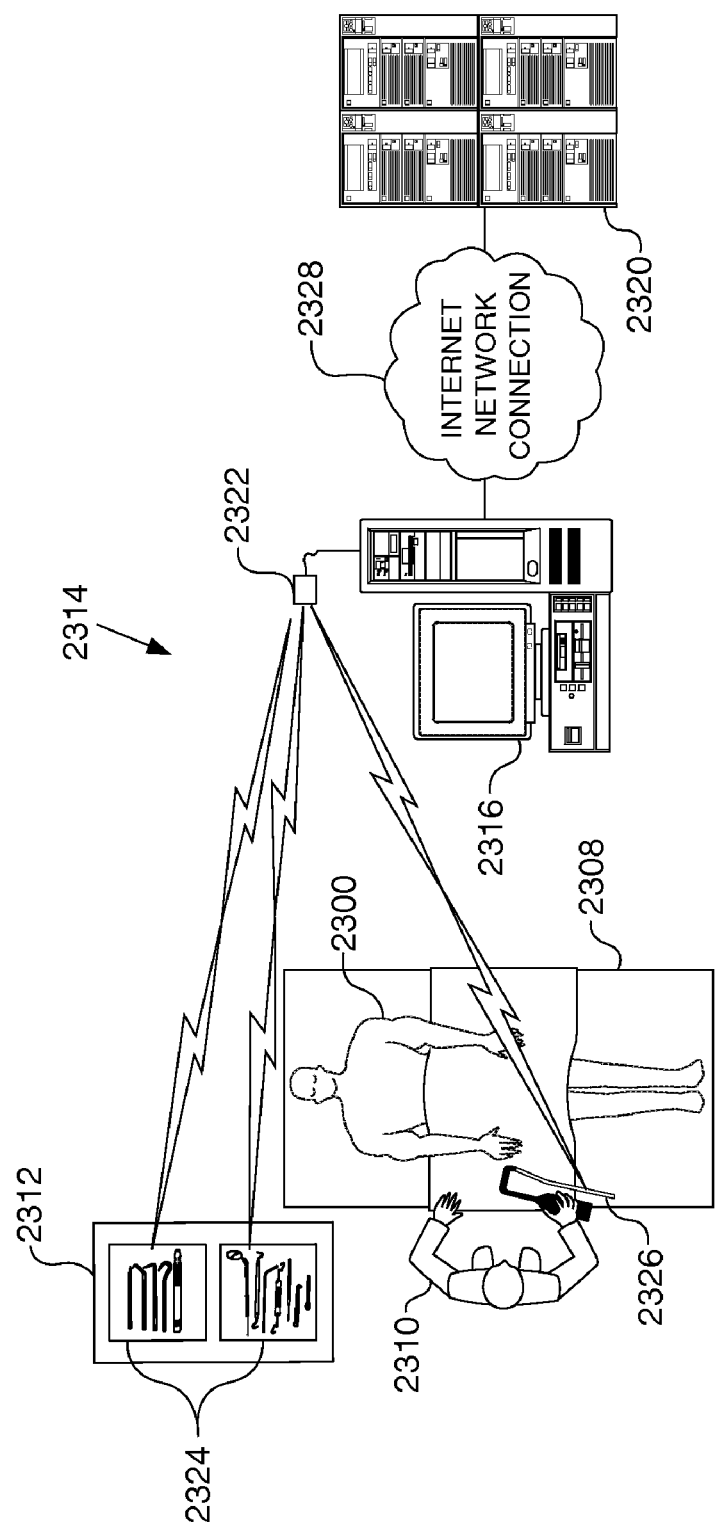
FIG. 41 is a schematic illustrating a system for retrieving surgical information.

FIG. 41 illustrates a system 2314 for retrieving surgical information. FIG. 41 illustrates a patient 2300 on a table 2308, a health professional 2310, and a back table 2312. The health professional 2310 may be a doctor, nurse, physician's assistant, nurse practitioner, surgeon, orthopaedic surgeon, sales representative, surgical technician, or other person. The system 2314 includes a computing device 2316, a reader 2322, one or more sterilization cases 2324, and one or more medical devices 2326. As examples, the reader 2322 may be an optical reader, an infrared sensor, or a radio frequency identification reader. The reader 2322 is connected to the computing device 2316. The medical device 2326 may be an instrument or an implant. Optionally, the system 2314 may include a network connection 2328 and one or more servers 2320. If so, the computing device 2316 may be connected to the network connection 2328 and/or may be networked to the server 2320. The computing device 2316 may be a desktop computer, a laptop computer, a personal data assistant, a multimedia player, cellular telephone, or computer assisted surgery system. In the embodiment depicted in FIG. 41, the computing device 2316 is a desktop computer. Further, there are two sterilization cases 2324 shown in FIG. 41 but a greater or lesser number may be used.

The reader 2322 may sense the instrument tray and/or medical device to read a component specific alphanumeric string of characters which identifies the instrument tray or medical device. The character string is passed on to the computing device 2316, and the computing device 2316 then retrieves one or more files relating to the character string. Thus, the computing device 2316 retrieves files related to the particular tray or device. The file may be any type of media file, such as a video, audio, or text file. For example, the retrieved file may be a surgical technique that instructs the user on the steps for performing a particular surgery. Thereafter, the computing device 2316 executes the files, which may include displaying a video, displaying text, playing an audio, or some combination thereof.

In the case of an RFID reader, the RFID reader reads a unique alphanumeric string of characters from the RFID chip on the instrument tray or medical device. This character string is associated with a specific implant system. The computing device then accesses its hard drive memory files or the server to retrieve stored files associated with the character string.

In one particular embodiment, there is an area around the patient 2300 that defines a surgical field. The surgical field may be defined by placing emitters (not shown) in strategic locations around the table 2308. As examples, the emitters may be optical emitters or radiation emitters. In this embodiment, the reader 2322 can sense when instrument trays and/or medical devices enter the surgical field. Thus, as the particular instrument tray or medical device enters the surgical field, the reader 2322 senses the item and sends the character string to the computing device 2316. The computing device 2316 automatically retrieves the relevant file and executes the file. Of course, the computing device may retrieve multiple files relating to one particular surgical implant system or repeat the process for individual components. This embodiment is particularly useful for orthopaedic surgery as the surgeon may be presented with relevant information contemporaneously with the surgical step being performed.

FIG. 42 illustrates a process for retrieving surgical information. The process starts at step 2400. In step 2410, an instrument tray is brought into the operating room. The medical device tag is read in step 2412. In step 2414, a decision is made whether input is required from a user. For example, if the instrument tray may be used in multiple types of surgeries, the computing device can prompt the user to identify the particular surgery being performed for the retrieval of the most relevant information. The computing device retrieves one or more relevant files in step 2416. In some embodiments, this is done all at once for a particular surgical procedure. Otherwise, file retrieval is piecemeal and dependent upon the selected instrument tray or medical device. The relevant files may be retrieved from local memory or from a remote device over a network. In optional step 2418, the computing device identifies medical devices within the surgical field. The computing device executes the relevant file in step 2420. Thereafter, the process ends.

One example in accordance with the present invention is as follows. In preparation for a surgical procedure, such as a total knee replacement, members of medical device central processing sterilize the medical instruments to be used. A variety of medical instruments may be sterilized, such as a cutting block, fin stem punch, femoral trial, and patella clamp.

Prior to sterilization, a passive RFID tag, such as those manufactured or supplied by Danby, TTP, QinetiQ, or Precimed may be attached to each medical instrument. In some embodiments, the tag may be a combined RFID/GPS tag available from QinetiQ. The RFID tag is preferably attached by an instrument management company to the medical instruments with an epoxy adhesive, but may be attached immediately prior to sterilization by a clip or some other mechanical method.

The medical instruments, with an RFID tag attached to each one, are placed inside a sterilization case, such as model number 7112-9401/9402/9400 manufactured by Smith & Nephew, Inc. The sterilization case is wrapped in a plastic wrap, such as Kimberly-Clark 600 sterilization pouch or sterilization wrapper, and the wrap is then sealed.

The sealed sterilization case containing the medical instruments is placed in the sterilization pouch and the pouch is sealed. The completed assembly is then placed into an autoclave and subjected to a medical autoclave sterilization process. The sterilization case is removed then from the autoclave and placed on a shelf.

The wrapped instrument cases are taken to a central storage location. When the case is scheduled, they are taken to a staging area or up to the operating room. Just prior to surgery, a medical instrument sales representative, hospital employee, or nurse scans the instrument packets in central processing, a staging area, or in the operating room with an RFID reader. The reader is preferably a handheld reader, but may also be a mat reader, a stationary reader, or any other reader disclosed herein. In a particularly preferred embodiment, the reader is handheld and is scanned over the wrapped sterilization case prior to the sealed outer wrap being broken.

The information obtained from the RFID tag is sent, through wireless or wired connection, to a computer or handheld computing device, such as a Hewlet-Packard iPAQ or a network. In an alternative embodiment, the information is displaced on a screen located on the reader. The output may show, for example, a sterilization case list, the contents of the case, the part numbers necessary for a procedure, which instruments are missing, or any information relevant to medical instrument inventory and management. If the interface indicates that all instruments necessary for the procedure are present, then the sealed plastic wrap is broken, the instruments are removed from the sterilization case, and laid on a tray table in the operating room. If the interface indicates that all instruments necessary for the procedure are present, then the person scanning would notify someone assisting in the surgery that the packet is not complete and that another packet is read to supplement or replace the first packet.

There are multiple users of this system. They include but are not limited to hospital staff (nurses, doctors, sterilization techs, etc.), sales representatives (associates), distributors, and manufacturers. The invention provides the users with a system that allows them to locate certain items as well as obtain additional information. Types of items can include instruments, instrument sets, implants, implant sets, and capital equipment. Types of information that can be retrieved include but are not limited to history of use, item sterilization status, who handled the item last, whether an instrument is missing from a set, and whether inventory of a particular item is low.

The tracking system operates by communicating between devices, such as instruments and trays or a tray and the system tracker. To track the location of an instrument, implant or other inventory device, a user must interface with a computer system. The system is then able to identify the location of the device and can provide additional information about the device. This additional information is data that is stored on the RF tag as well as exits in a history file managed by the tracking system which the user can review.

To determine if a set is ready for surgery the user can view the display on the set which when prompted identifies whether the set contains the pertinent devices to perform the surgery or not. If not, the display can show what devices are missing. This can be achieved by having an exciter housed in the set, and when prompted by the user it sends a signal out that will generate a response from all devices within the set. The exciter is part of a computer system that also contains a receiver that will read these responses. From these responses, the system can determine if all of the required devices are currently housed in the set or not.

The invention for providing the surgeon with the surgical technique also uses RFID recognition. An RFID tag is rigidly affixed to the instruments, implants, and devices. Located in the operating room is a computer system that is integrated with an exciter and a receiver. When prompted by the user, the computer sends a signal via the exciter that will generate a response signal. This response signal is then received by the receiver and read into the computer. This signal identifies the particular instrument or implant. This information allows the computer to pull up a written or video technique showing how to use the instrument or implant. It also can show the user information on how to perform the entire surgical technique using the system.

A read/writeable RF tag is permanently affixed to instruments, implants, and devices. These tags can be either passive or active. Both tag types can contain multiple types of information such as manufacturer data, instrument name, quality control number, instructions for use, expiration date, last date used, last sterilization method and date, and the last person to handle the device.

An exciter is used when information is needed to be obtained from an instrument, implant, or device that contains a passive tag. The passive tags when excited by an exciter signal will emit an RF response signal. These exciters are used in conjunction with a receiver and a computer that controls the exciter's activities as well as processes the received signals. These computers can be connected to an area network. These exciter/receiver systems may be located in various areas such that they can communicate with the desired instrument, implant, or device. An example would be in an OR, a central supply facility, manufacturing facility, or on an instrument case.

A global and local system is set-up to allow users such as manufacturers, vendors, sales representatives, surgical techs, or surgeons to determine information about a particular device, instrument set, or implant set.

One example includes a local user attempting to locate a specific instrument set within a hospital. This person can access a computer system that using RF communication as previously described can determine the exact location of the instrument set within the hospital as well as provide other pertinent information (sterility status, expiration date, user instructions, etc.). This computer system could be an integrated desktop, laptop, or PDA.

An alternate embodiment of this invention would be a handheld device that will project a light source onto the device which the user is attempting to locate. This would be helpful when one is standing a room full of instrument sets and is trying to find a needle in the haystack.

Instrument tracking can also occur at a larger level. This includes distributors trying to locate where a specific instrument set is in the world. This concept is similar to the tracking done by shipping companies except that it is not tracking at ports only, but rather provides real-time location information. Another use is that of representatives or manufacturers attempting to determine the usage or activity of a set. The system can detect movement of the set and will track and store this information which can be accessed by the user for analysis.

Another facet of the invention allows the user(s) to determine if an instrument set is ready for use in surgery. The set itself would contain an exciter/receiver computer system that would verify that all needed instruments, implants, or devices are in the set by reading and evaluating all response emissions. The user can control what criteria is used to determine what are "needed". This information can be displayed directly on a display screen affixed to the set and/or can be displayed using a separate computer system. An example would be a display screen showing a green box signifying that the set is ready for use in surgery as well as showing the date of the last sterilization procedure the set has undergone. Or the display could show a red box signifying that it is not ready for surgery and provide a list of instruments that are missing from the set.

This invention also allows for a user to access the surgical technique for an instrument, implant, device, or an entire system using a computer. This is accomplished by having a computer system that is integrated with an exciter and receiver. This system can communicate with a device that contains an RFID tag. The tag will contain information regarding the surgical technique and this information will be displayed on the screen. Another embodiment would be that the product information read from the instrument would be used by the computer to access the technique material and then display it. This could include a video and/or the written surgical technique. This is a useful tool when operating with a new instrument/implant or one seldom used.

This invention includes the ability for a hospital or an account manager to track and manage the inventory of a hospital. By tracking instruments, implants, and other devices, the automated system can determine if the inventory level for any item has reached a level where the item stock needs to be replenished. This would include for example the system noticing that a hospital has only two implants of a certain size left. This would automatically prompt the system to send out a replenishment order request. This benefits the hospital by never running out of a needed instrument or implant, as well as to the rep who no longer has to spend time managing inventory.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A system for tracking a surgical asset, the system comprising:
   a. a tag operatively connected to the surgical asset, the tag being configured to provide localized location information to a transceiver when the surgical asset is located in a first area associated with the transceiver, the first area corresponding to an interior of a building;
   b. a readiness module operatively connected to the surgical asset, the readiness module being configured to determine readiness information associated with the surgical asset and provide the readiness information to the transceiver; the readiness information comprising an indication of whether the surgical asset comprises a set of components needed for a selected medical procedure;
   c. the transceiver configured to provide the localized location information and the readiness information to an application server;
   d. a global positioning satellite reader operatively connected to the surgical asset, the global positioning satellite reader adapted to:
      determine localized location information for the surgical asset based on location data received from at least one satellite when the surgical asset is located in a second area associated with the at least one satellite; and
      provide the localized location information to the application server; and
   e. the application server configured to:
      determine a location of the surgical asset using at least one of a triangulation algorithm on the localized location information received from the transceiver or using the localized location information received from the global positioning satellite reader; and
      determine a readiness of the surgical asset using the readiness information.

2. The system according to claim 1, wherein the surgical asset is a sealed sterilization case adapted to allow radio frequency signals to pass through at least one side of the case, the system further comprising:
   a. at least one radio frequency identification tag;
   b. at least one medical instrument contained in the sealed sterilization case and attached to the radio frequency identification tag; and
   c. a reader adapted to obtain information, via radio frequency, from said radio frequency identification tag.

3. The system according to claim 2, further comprising at least one surface that has at least one opening adapted in size or shape to allow radio frequency signals to enter and leave the case.

4. The system according to claim 2, composed of a material that is configured to allow radio frequency signals to enter and leave the case.

5. The system according to claim 2, wherein the radio frequency identification tag associated with the at least one medical instrument is embedded inside the at least one medical instrument.

6. The system according to claim 2, wherein the radio frequency identification tag associated with the at least one medical instrument is attached on the outside surface of the at least one medical instrument.

7. The system according to claim 2, wherein each of the radio frequency identification tags is a passive device.

8. The system according to claim 2, wherein each of the radio frequency identification tags is an active device.

9. The system according to claim 2, wherein the reader is electrically connected to a microprocessor.

10. The system according to claim 2, wherein the reader is in wireless communication with a microprocessor.

11. The system according to claim 2, wherein the information includes at least one of the following:
    a. the identification of the at least one medical instrument to which the radio frequency identification tag is associated with;
    b. the surgical technique associated with the at least one medical instrument to which the radio frequency identification tag is associated with; and
    c. the manufacturing history of the at least one medical instrument to which the radio frequency identification tag is associated with.

12. The system according to claim 2, further comprising a case radio frequency identification tag attached or associated with the outside of the sterilization case.

13. The system according to claim 12, wherein the case radio frequency identification tag obtains information, via radio frequency, from the radio frequency tags associated with the medical instruments and communicates the information via radio frequency to the reader.

14. The system of claim 2, wherein the reader is the transceiver.

15. The system of claim 1, wherein the application server is configured to send a request for localized location information to at least one of the transceiver or the global positioning satellite reader.

16. The system of claim 1, wherein the surgical asset is selected from the group consisting of a sterilization case, a medical instrument tray, a medical instrument, and a medical implant.

17. The system of claim 1, wherein the transceiver is configured to utilize radio frequency transmission.

18. The system of claim 17, wherein the transceiver is configured to communicate with the application server through a wireless telephone network or a wireless pager network.

19. The system of claim 1, wherein the set of components needed for the selected medical procedure comprises at least one of: a medical instrument; a medical implant; or a medical device.

20. The system of claim 1, wherein the tag is associated with a real-time location system.

21. The system of claim 1, wherein the readiness information further comprises information representing whether at least one of the components of the set has been sterilized.

22. A method of tracking a surgical asset, comprising:
  a. sending a request for location information via wireless transmission;
  b. receiving GPS localized location information from a global positioning satellite reader operatively connected to the surgical asset within a first area in which the surgical asset is being transported;
  c. determining a transport location of the surgical asset using the GPS localized location information, the transport location being within the first area;
  d. receiving node localized location information from a transceiver associated with a second area of a node, the localized location information corresponding to a tag associated with the surgical asset within the second area, the node being associated with a building;
  e. determining a node location of the surgical asset using a triangulation algorithm and the node localized location information, the node location being within the second area of the node;
  f. receiving readiness information for the surgical asset within the second area from the transceiver; the readiness information comprising an indication of whether the surgical asset comprises a set of components needed for a selected medical procedure;
  g. determining the readiness of the surgical asset using the readiness information; and
  h. outputting the node location of the surgical asset and an indicator corresponding to the readiness of the surgical asset.

23. The method of claim 22, wherein sending the request for localized location information via wireless transmission comprises sending the request periodically.

24. The method of claim 22, wherein determining the first location of the surgical asset using the GPS localized location information comprises:
  periodically receiving GPS localized location information during transport of the surgical asset; and
  periodically determining the transport location of the surgical asset during transport of the surgical asset.

25. The method of claim 22, wherein receiving node localized location information from the transceiver associated with a second area of a node comprises receiving node localized location information over a wireless telephone network or a wireless pager network.

26. The system of claim 22, wherein the set of components needed for the selected medical procedure comprises at least one of: a medical instrument; a medical implant; or a medical device.

27. The method of claim 26, wherein the surgical procedure is scheduled to occur in the building, wherein the building is a hospital.

28. The method of claim 22, wherein the surgical asset comprises a plurality of surgical assets, the method further comprising:
  transmitting a request for location information for each of the plurality of surgical assets; and
  determining a location for each of the plurality of surgical assets using at least one of GPS localized location information or node localized location information.

29. The system of claim 22, wherein the readiness information further comprises a date of a most recent sterilization procedure for at least one of the components of the set.

* * * * *